US010751094B2

(12) United States Patent
Green et al.

(10) Patent No.: US 10,751,094 B2
(45) Date of Patent: Aug. 25, 2020

(54) ADJUSTABLE SPINAL IMPLANT

(71) Applicant: NuVasive Specialized Orthopedics, Inc., San Diego, CA (US)

(72) Inventors: Stuart A. Green, Long Beach, CA (US); Blair Walker, Mission Viejo, CA (US); Thomas B. Buford, Laguna Beach, CA (US); Urs Weber, Irvine, CA (US)

(73) Assignee: NuVasive Specialized Orthopedics, Inc., San Diego, CA (US)

( * ) Notice: Subject to any disclaimer, the term of this patent is extended or adjusted under 35 U.S.C. 154(b) by 0 days.

(21) Appl. No.: 14/511,084

(22) Filed: Oct. 9, 2014

(65) Prior Publication Data

US 2015/0105826 A1 Apr. 16, 2015

Related U.S. Application Data

(60) Provisional application No. 61/889,496, filed on Oct. 10, 2013.

(51) Int. Cl.
*A61B 17/70* (2006.01)

(52) U.S. Cl.
CPC ........ *A61B 17/7053* (2013.01); *A61B 17/707* (2013.01); *A61B 17/7055* (2013.01); *A61B 17/7016* (2013.01)

(58) Field of Classification Search
CPC ................. A61B 17/025; A61B 17/66; A61B 17/7047–7058; A61B 17/7062–7071; A61B 2017/0256
See application file for complete search history.

(56) References Cited

U.S. PATENT DOCUMENTS 1,599,538 A 9/1926 Ludger
3,111,945 A 11/1963 Von
(Continued)

FOREIGN PATENT DOCUMENTS

AU 20068468 3/2001
CN 101040807 9/2007
(Continued)

OTHER PUBLICATIONS

US 9,161,784 B2, 10/2015, Buttermann (withdrawn)
(Continued)

*Primary Examiner* — Nicholas J Plionis
*Assistant Examiner* — Steven J Cotroneo
(74) *Attorney, Agent, or Firm* — NuVasive, Inc.

(57) ABSTRACT

In one embodiment, a non-invasively adjustable spinal system for treatment of a subject having spondylolisthesis includes a first implantable actuator having at least one anchoring structure, the anchoring structure configured to facilitate securement of the first implantable actuator to a portion of the sacrum of the subject. The non-invasively adjustable spinal system can further include an adjustment element, configured to be coupled to the first implantable actuator, the adjustment element having an engagement structure configured to engage at least one transverse process of a lumbar vertebra of the subject. The non-invasively adjustable spinal system can further include a driving element, wherein remote activation of the driving element causes movement of the adjustment element in relation to the first implantable actuator.

14 Claims, 18 Drawing Sheets

(56) References Cited

U.S. PATENT DOCUMENTS

| | | |
|---|---|---|
| 3,372,476 A | 3/1968 | Richard et al. |
| 3,377,576 A | 4/1968 | Edwin et al. |
| 3,397,928 A | 8/1968 | Galle |
| 3,512,901 A | 5/1970 | Law |
| 3,527,220 A | 9/1970 | Summers |
| 3,597,781 A | 8/1971 | Eibes et al. |
| 3,726,279 A | 4/1973 | Barefoot et al. |
| 3,749,098 A | 7/1973 | De Bennetot |
| 3,750,194 A | 8/1973 | Summers |
| 3,810,259 A | 5/1974 | Summers |
| 3,840,018 A | 10/1974 | Heifetz |
| 3,866,510 A | 2/1975 | Eibes et al. |
| 3,900,025 A | 8/1975 | Barnes, Jr. |
| 3,915,151 A | 10/1975 | Kraus |
| RE28,907 E | 7/1976 | Eibes et al. |
| 3,976,060 A | 8/1976 | Hildebrandt et al. |
| 4,010,758 A | 3/1977 | Rockland et al. |
| 4,056,743 A | 11/1977 | Clifford et al. |
| 4,068,821 A | 1/1978 | Morrison |
| 4,078,559 A | 3/1978 | Nissinen |
| 4,118,805 A | 10/1978 | Reimels |
| 4,204,541 A | 5/1980 | Kapitanov |
| 4,222,374 A | 9/1980 | Sampson et al. |
| 4,235,246 A | 11/1980 | Weiss |
| 4,256,094 A | 3/1981 | Kapp et al. |
| 4,286,584 A | 9/1981 | Sampson et al. |
| 4,300,223 A | 11/1981 | Maire |
| 4,357,946 A | 11/1982 | Dutcher et al. |
| 4,386,603 A | 6/1983 | Mayfield |
| 4,395,259 A | 7/1983 | Prestele et al. |
| 4,448,191 A | 5/1984 | Rodnyansky et al. |
| 4,486,176 A | 12/1984 | Tardieu et al. |
| 4,501,266 A | 2/1985 | McDaniel |
| 4,522,501 A | 6/1985 | Shannon |
| 4,537,520 A | 8/1985 | Ochiai et al. |
| 4,550,279 A | 10/1985 | Klein |
| 4,561,798 A | 12/1985 | Elcrin et al. |
| 4,573,454 A | 3/1986 | Hoffman |
| 4,592,339 A | 6/1986 | Kuzmak et al. |
| 4,592,355 A | 6/1986 | Antebi |
| 4,595,007 A | 6/1986 | Mericle |
| 4,642,257 A | 2/1987 | Chase |
| 4,658,809 A | 4/1987 | Ulrich et al. |
| 4,696,288 A | 9/1987 | Kuzmak et al. |
| 4,700,091 A | 10/1987 | Wuthrich |
| 4,747,832 A | 5/1988 | Buffet |
| 4,760,837 A | 8/1988 | Petit |
| 4,854,304 A | 8/1989 | Zielke |
| 4,872,515 A | 10/1989 | Lundell |
| 4,904,861 A | 2/1990 | Epstein et al. |
| 4,931,055 A | 6/1990 | Bumpus et al. |
| 4,940,467 A | 7/1990 | Tronzo |
| 4,957,495 A | 9/1990 | Kluger |
| 4,973,331 A | 11/1990 | Pursley et al. |
| 4,978,323 A | 12/1990 | Freedman |
| 4,998,013 A | 3/1991 | Epstein et al. |
| 5,010,879 A | 4/1991 | Moriya et al. |
| 5,030,235 A | 7/1991 | Campbell, Jr. |
| 5,041,112 A | 8/1991 | Mingozzi et al. |
| 5,053,047 A | 10/1991 | Yoon |
| 5,064,004 A | 11/1991 | Lundell |
| 5,074,868 A | 12/1991 | Kuzmak |
| 5,074,882 A | 12/1991 | Grammont et al. |
| 5,092,889 A | 3/1992 | Campbell, Jr. |
| 5,133,716 A | 7/1992 | Plaza |
| 5,142,407 A | 8/1992 | Varaprasad et al. |
| 5,152,770 A | 10/1992 | Bengmark et al. |
| 5,156,605 A | 10/1992 | Pursley et al. |
| 5,176,618 A | 1/1993 | Freedman |
| 5,180,380 A | 1/1993 | Pursley et al. |
| 5,222,976 A | 6/1993 | Yoon |
| 5,226,429 A | 7/1993 | Kuzmak |
| 5,261,908 A | 11/1993 | Campbell, Jr. |
| 5,263,955 A | 11/1993 | Baumgart et al. |
| 5,290,289 A | 3/1994 | Sanders et al. |
| 5,306,275 A | 4/1994 | Bryan |
| 5,330,503 A | 7/1994 | Yoon |
| 5,334,202 A | 8/1994 | Carter |
| 5,336,223 A | 8/1994 | Rogers |
| 5,356,411 A | 10/1994 | Spievack |
| 5,356,424 A | 10/1994 | Buzerak et al. |
| 5,360,407 A | 11/1994 | Leonard et al. |
| 5,364,396 A | 11/1994 | Robinson et al. |
| 5,381,943 A | 1/1995 | Allen et al. |
| 5,399,168 A | 3/1995 | Wadsworth, Jr. et al. |
| 5,403,322 A | 4/1995 | Herzenberg et al. |
| 5,429,638 A | 7/1995 | Muschler et al. |
| 5,433,721 A | 7/1995 | Hooven et al. |
| 5,437,266 A | 8/1995 | McPherson et al. |
| 5,449,368 A | 9/1995 | Kuzmak |
| 5,466,261 A | 11/1995 | Richelsoph |
| 5,468,030 A | 11/1995 | Walling |
| 5,480,437 A | 1/1996 | Draenert |
| 5,498,262 A | 3/1996 | Bryan |
| 5,509,888 A | 4/1996 | Miller |
| 5,516,335 A | 5/1996 | Kummer et al. |
| 5,527,309 A | 6/1996 | Shelton |
| 5,536,269 A | 7/1996 | Spievack |
| 5,536,296 A | 7/1996 | Ten Eyck et al. |
| 5,549,610 A | 8/1996 | Russell et al. |
| 5,573,496 A | 11/1996 | McPherson et al. |
| 5,575,790 A | 11/1996 | Chen et al. |
| 5,582,616 A | 12/1996 | Bolduc et al. |
| 5,601,224 A | 2/1997 | Bishop et al. |
| 5,620,445 A | 4/1997 | Brosnahan et al. |
| 5,620,449 A | 4/1997 | Faccioli et al. |
| 5,626,579 A | 5/1997 | Muschler et al. |
| 5,626,613 A | 5/1997 | Schmieding |
| 5,628,888 A | 5/1997 | Bakhir et al. |
| 5,632,744 A | 5/1997 | Campbell, Jr. |
| 5,659,217 A | 8/1997 | Petersen |
| 5,662,683 A | 9/1997 | Kay |
| 5,672,175 A | 9/1997 | Martin |
| 5,672,177 A | 9/1997 | Seldin |
| 5,676,162 A | 10/1997 | Larson, Jr. et al. |
| 5,693,091 A | 12/1997 | Larson, Jr. et al. |
| 5,700,263 A | 12/1997 | Schendel |
| 5,702,430 A | 12/1997 | Larson, Jr. et al. |
| 5,704,893 A | 1/1998 | Timm |
| 5,704,938 A | 1/1998 | Staehlin et al. |
| 5,704,939 A | 1/1998 | Justin |
| 5,720,746 A | 2/1998 | Soubeiran |
| 5,722,429 A | 3/1998 | Larson, Jr. et al. |
| 5,722,930 A | 3/1998 | Larson, Jr. et al. |
| 5,743,910 A | 4/1998 | Bays et al. |
| 5,758,666 A | 6/1998 | Larson, Jr. et al. |
| 5,762,599 A | 6/1998 | Sohn |
| 5,766,208 A | 6/1998 | McEwan |
| 5,771,903 A | 6/1998 | Jakobsson |
| 5,800,434 A | 9/1998 | Campbell, Jr. |
| 5,810,815 A | 9/1998 | Morales |
| 5,824,008 A | 10/1998 | Bolduc et al. |
| 5,827,286 A | 10/1998 | Incavo et al. |
| 5,829,662 A | 11/1998 | Allen et al. |
| 5,830,221 A | 11/1998 | Stein et al. |
| 5,843,129 A | 12/1998 | Larson, Jr. et al. |
| 5,874,796 A | 2/1999 | Petersen |
| 5,879,375 A | 3/1999 | Larson, Jr. et al. |
| 5,902,304 A | 5/1999 | Walker et al. |
| 5,935,127 A | 8/1999 | Border |
| 5,938,669 A | 8/1999 | Klaiber et al. |
| 5,945,762 A | 8/1999 | Chen et al. |
| 5,954,915 A | 9/1999 | Voorhees et al. |
| 5,961,553 A | 10/1999 | Coty et al. |
| 5,964,763 A | 10/1999 | Incavo et al. |
| 5,976,138 A | 11/1999 | Baumgart et al. |
| 5,979,456 A | 11/1999 | Magovern |
| 5,985,110 A | 11/1999 | Bakhir et al. |
| 5,997,490 A | 12/1999 | McLeod et al. |
| 6,009,837 A | 1/2000 | McClasky |
| 6,022,349 A | 2/2000 | McLeod et al. |
| 6,033,412 A | 3/2000 | Losken et al. |
| 6,034,296 A | 3/2000 | Elvin et al. |
| 6,067,991 A | 5/2000 | Forsell |

(56) References Cited

U.S. PATENT DOCUMENTS

| | | |
|---|---|---|
| 6,074,341 A | 6/2000 | Anderson et al. |
| 6,074,882 A | 6/2000 | Eckardt |
| 6,092,531 A | 7/2000 | Chen et al. |
| 6,102,922 A | 8/2000 | Jakobsson et al. |
| 6,106,525 A | 8/2000 | Sachse |
| 6,126,660 A | 10/2000 | Dietz |
| 6,126,661 A | 10/2000 | Faccioli et al. |
| 6,138,681 A | 10/2000 | Chen et al. |
| 6,139,316 A | 10/2000 | Sachdeva et al. |
| 6,162,223 A | 12/2000 | Orsak et al. |
| 6,183,476 B1 | 2/2001 | Gerhardt et al. |
| 6,200,317 B1 | 3/2001 | Aalsma et al. |
| 6,210,347 B1 | 4/2001 | Forsell |
| 6,217,847 B1 | 4/2001 | Contag et al. |
| 6,221,074 B1 | 4/2001 | Cole et al. |
| 6,234,299 B1 | 5/2001 | Voorhees et al. |
| 6,234,956 B1 | 5/2001 | He et al. |
| 6,241,730 B1 | 6/2001 | Alby |
| 6,245,075 B1 | 6/2001 | Betz et al. |
| 6,283,156 B1 | 9/2001 | Motley |
| 6,296,643 B1 | 10/2001 | Hopf et al. |
| 6,296,656 B1 | 10/2001 | Bolduc et al. |
| 6,299,613 B1 | 10/2001 | Ogilvie et al. |
| 6,315,784 B1 | 11/2001 | Djurovic |
| 6,319,255 B1 | 11/2001 | Grundei et al. |
| 6,321,106 B1 | 11/2001 | Lemelson |
| 6,325,805 B1 | 12/2001 | Ogilvie et al. |
| 6,327,492 B1 | 12/2001 | Lemelson |
| 6,331,744 B1 | 12/2001 | Chen et al. |
| 6,336,929 B1 | 1/2002 | Justin |
| 6,343,568 B1 | 2/2002 | McClasky |
| 6,358,283 B1 | 3/2002 | Hogfors et al. |
| 6,375,682 B1 | 4/2002 | Fleischmann et al. |
| 6,386,083 B1 | 5/2002 | Hwang |
| 6,389,187 B1 | 5/2002 | Greenaway et al. |
| 6,400,980 B1 | 6/2002 | Lemelson |
| 6,402,753 B1 | 6/2002 | Cole et al. |
| 6,409,175 B1 | 6/2002 | Evans et al. |
| 6,416,516 B1 | 7/2002 | Stauch et al. |
| 6,417,750 B1 | 7/2002 | Sohn |
| 6,423,061 B1 | 7/2002 | Bryant |
| 6,432,040 B1 | 8/2002 | Meah |
| 6,450,173 B1 | 9/2002 | Forsell |
| 6,450,946 B1 | 9/2002 | Forsell |
| 6,453,907 B1 | 9/2002 | Forsell |
| 6,454,698 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,460,543 B1 | 10/2002 | Forsell |
| 6,461,292 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,471,635 B1 | 10/2002 | Forsell |
| 6,475,136 B1 | 11/2002 | Forsell |
| 6,482,145 B1 | 11/2002 | Forsell |
| 6,494,879 B2 | 12/2002 | Lennox et al. |
| 6,499,907 B1 | 12/2002 | Baur |
| 6,500,110 B1 | 12/2002 | Davey et al. |
| 6,503,189 B1 | 1/2003 | Forsell |
| 6,508,820 B2 | 1/2003 | Bales |
| 6,510,345 B1 | 1/2003 | Van Bentem |
| 6,511,490 B2 | 1/2003 | Robert |
| 6,527,701 B1 | 3/2003 | Sayet et al. |
| 6,527,702 B2 | 3/2003 | Whalen et al. |
| 6,536,499 B2 | 3/2003 | Voorhees et al. |
| 6,537,196 B1 | 3/2003 | Creighton, IV et al. |
| 6,547,801 B1 | 4/2003 | Dargent et al. |
| 6,554,831 B1 | 4/2003 | Rivard et al. |
| 6,558,400 B2 | 5/2003 | Deem et al. |
| 6,562,051 B1 | 5/2003 | Bolduc et al. |
| 6,565,573 B1 | 5/2003 | Ferrante et al. |
| 6,565,576 B1 | 5/2003 | Stauch et al. |
| 6,573,706 B2 | 6/2003 | Mendes et al. |
| 6,582,313 B2 | 6/2003 | Perrow |
| 6,583,630 B2 | 6/2003 | Mendes et al. |
| 6,587,719 B1 | 7/2003 | Barrett et al. |
| 6,595,912 B2 | 7/2003 | Lau et al. |
| 6,602,184 B2 | 8/2003 | Lau et al. |
| 6,604,529 B2 | 8/2003 | Kim |
| 6,607,363 B1 | 8/2003 | Domroese |
| 6,609,025 B2 | 8/2003 | Barrett et al. |
| 6,612,978 B2 | 9/2003 | Lau et al. |
| 6,612,979 B2 | 9/2003 | Lau et al. |
| 6,616,669 B2 | 9/2003 | Ogilvie et al. |
| 6,621,956 B2 | 9/2003 | Greenaway et al. |
| 6,626,899 B2 | 9/2003 | Houser et al. |
| 6,626,917 B1 | 9/2003 | Craig |
| 6,627,206 B2 | 9/2003 | Lloyd |
| 6,649,143 B1 | 11/2003 | Contag et al. |
| 6,656,135 B2 | 12/2003 | Zogbi et al. |
| 6,656,194 B1 | 12/2003 | Gannoe et al. |
| 6,657,351 B2 | 12/2003 | Chen et al. |
| 6,667,725 B1 | 12/2003 | Simons et al. |
| 6,669,687 B1 | 12/2003 | Saadat |
| 6,673,079 B1 | 1/2004 | Kane |
| 6,676,674 B1 | 1/2004 | Dudai |
| 6,682,474 B2 | 1/2004 | Lau et al. |
| 6,689,046 B2 | 2/2004 | Sayet et al. |
| 6,702,732 B1 | 3/2004 | Lau et al. |
| 6,702,816 B2 | 3/2004 | Buhler |
| 6,706,042 B2 | 3/2004 | Taylor |
| 6,709,293 B2 | 3/2004 | Mori et al. |
| 6,709,385 B2 | 3/2004 | Forsell |
| 6,730,087 B1 | 5/2004 | Butsch |
| 6,749,556 B2 | 6/2004 | Banik |
| 6,752,754 B1 | 6/2004 | Feng et al. |
| 6,761,503 B2 | 7/2004 | Breese |
| 6,765,330 B2 | 7/2004 | Baur |
| 6,769,499 B2 | 8/2004 | Cargill et al. |
| 6,773,437 B2 | 8/2004 | Ogilvie et al. |
| 6,774,624 B2 | 8/2004 | Anderson et al. |
| 6,789,442 B2 | 9/2004 | Forch |
| 6,796,984 B2 | 9/2004 | Soubeiran |
| 6,802,844 B2 | 10/2004 | Ferree |
| 6,802,847 B1 | 10/2004 | Carson et al. |
| 6,809,434 B1 | 10/2004 | Duncan et al. |
| 6,835,183 B2 | 12/2004 | Lennox et al. |
| 6,835,207 B2 | 12/2004 | Zacouto et al. |
| 6,849,076 B2 | 2/2005 | Blunn et al. |
| 6,852,113 B2 | 2/2005 | Nathanson et al. |
| 6,864,647 B2 | 3/2005 | Duncan et al. |
| 6,884,248 B2 | 4/2005 | Bolduc et al. |
| 6,890,515 B2 | 5/2005 | Contag et al. |
| 6,908,605 B2 | 6/2005 | Contag et al. |
| 6,915,165 B2 | 7/2005 | Forsell |
| 6,916,462 B2 | 7/2005 | Contag et al. |
| 6,918,838 B2 | 7/2005 | Schwarzler et al. |
| 6,918,910 B2 | 7/2005 | Smith et al. |
| 6,921,360 B2 | 7/2005 | Banik |
| 6,921,400 B2 | 7/2005 | Sohngen |
| 6,923,951 B2 | 8/2005 | Contag et al. |
| 6,926,719 B2 | 8/2005 | Sohngen et al. |
| 6,939,533 B2 | 9/2005 | Contag et al. |
| 6,953,429 B2 | 10/2005 | Forsell |
| 6,961,553 B2 | 11/2005 | Zhao et al. |
| 6,971,143 B2 | 12/2005 | Domroese |
| 6,980,921 B2 | 12/2005 | Anderson et al. |
| 6,997,952 B2 | 2/2006 | Furukawa et al. |
| 7,001,327 B2 | 2/2006 | Whalen et al. |
| 7,001,346 B2 | 2/2006 | White |
| 7,008,425 B2 | 3/2006 | Phillips |
| 7,011,621 B2 | 3/2006 | Sayet et al. |
| 7,011,658 B2 | 3/2006 | Young |
| 7,011,682 B2 | 3/2006 | Lashinski et al. |
| 7,018,380 B2 | 3/2006 | Cole |
| 7,029,475 B2 | 4/2006 | Panjabi |
| 7,041,105 B2 | 5/2006 | Michelson |
| 7,060,075 B2 | 6/2006 | Govari et al. |
| 7,060,080 B2 | 6/2006 | Bachmann |
| 7,063,706 B2 | 6/2006 | Wittenstein |
| 7,077,802 B2 | 7/2006 | Lau et al. |

(56) References Cited

U.S. PATENT DOCUMENTS

| | | |
|---|---|---|
| 7,081,086 B2 | 7/2006 | Lau et al. |
| 7,083,629 B2 | 8/2006 | Weller et al. |
| 7,096,148 B2 | 8/2006 | Anderson et al. |
| 7,097,611 B2 | 8/2006 | Lau et al. |
| 7,105,029 B2 | 9/2006 | Doubler et al. |
| 7,105,968 B2 | 9/2006 | Nissen |
| 7,114,501 B2 | 10/2006 | Johnson et al. |
| 7,115,129 B2 | 10/2006 | Heggeness |
| 7,115,130 B2 | 10/2006 | Michelson |
| 7,124,493 B2 | 10/2006 | Lau et al. |
| 7,128,707 B2 | 10/2006 | Banik |
| 7,135,022 B2 | 11/2006 | Kosashvili et al. |
| 7,160,312 B2 | 1/2007 | Saadat |
| 7,163,538 B2 | 1/2007 | Altarac et al. |
| 7,172,607 B2 | 2/2007 | Hofle et al. |
| 7,175,589 B2 | 2/2007 | Deem et al. |
| 7,175,660 B2 | 2/2007 | Cartledge et al. |
| 7,186,262 B2 | 3/2007 | Saadat |
| 7,188,627 B2 | 3/2007 | Nelson et al. |
| 7,189,005 B2 | 3/2007 | Ward |
| 7,189,202 B2 | 3/2007 | Lau et al. |
| 7,189,251 B2 | 3/2007 | Kay |
| 7,191,007 B2 | 3/2007 | Desai et al. |
| 7,194,297 B2 | 3/2007 | Talpade et al. |
| 7,195,608 B2 | 3/2007 | Burnett |
| 7,198,774 B2 | 4/2007 | Contag et al. |
| 7,211,094 B2 | 5/2007 | Gannoe et al. |
| 7,216,648 B2 | 5/2007 | Nelson et al. |
| 7,217,284 B2 | 5/2007 | Houser et al. |
| 7,218,232 B2 | 5/2007 | DiSilvestro et al. |
| 7,232,449 B2 | 6/2007 | Sharkawy et al. |
| 7,234,468 B2 | 6/2007 | Johnson et al. |
| 7,234,544 B2 | 6/2007 | Kent |
| 7,238,152 B2 | 7/2007 | Lau et al. |
| 7,238,191 B2 | 7/2007 | Bachmann |
| 7,241,300 B2 | 7/2007 | Sharkawy et al. |
| 7,243,719 B2 | 7/2007 | Baron et al. |
| 7,255,682 B1 | 8/2007 | Bartol, Jr. et al. |
| 7,255,714 B2 | 8/2007 | Malek |
| 7,255,851 B2 | 8/2007 | Contag et al. |
| 7,276,022 B2 | 10/2007 | Lau et al. |
| 7,282,023 B2 | 10/2007 | Frering |
| 7,285,087 B2 | 10/2007 | Moaddeb et al. |
| 7,288,064 B2 | 10/2007 | Boustani et al. |
| 7,288,099 B2 | 10/2007 | Deem et al. |
| 7,288,101 B2 | 10/2007 | Deem et al. |
| 7,296,577 B2 | 11/2007 | Lashinski et al. |
| 7,297,150 B2 | 11/2007 | Cartledge et al. |
| 7,299,091 B2 | 11/2007 | Barrett et al. |
| 7,302,858 B2 | 12/2007 | Walsh et al. |
| 7,306,614 B2 | 12/2007 | Weller et al. |
| 7,311,690 B2 | 12/2007 | Burnett |
| 7,314,372 B2 | 1/2008 | Belfor et al. |
| 7,314,443 B2 | 1/2008 | Jordan et al. |
| 7,320,706 B2 | 1/2008 | Al-Najjar |
| 7,331,995 B2 | 2/2008 | Eisermann et al. |
| 7,333,013 B2 | 2/2008 | Berger |
| 7,338,433 B2 | 3/2008 | Coe |
| 7,340,306 B2 | 3/2008 | Barrett et al. |
| 7,351,198 B2 | 4/2008 | Byrum et al. |
| 7,351,240 B2 | 4/2008 | Hassler, Jr. et al. |
| 7,353,747 B2 | 4/2008 | Swayze et al. |
| 7,357,037 B2 | 4/2008 | Hnat et al. |
| 7,357,635 B2 | 4/2008 | Belfor et al. |
| 7,360,542 B2 | 4/2008 | Nelson et al. |
| 7,361,192 B2 | 4/2008 | Doty |
| 7,364,542 B2 | 4/2008 | Jambor et al. |
| 7,364,589 B2 | 4/2008 | Eisermann |
| 7,367,340 B2 | 5/2008 | Nelson et al. |
| 7,367,937 B2 | 5/2008 | Jambor et al. |
| 7,367,938 B2 | 5/2008 | Forsell |
| 7,371,244 B2 | 5/2008 | Chatlynne et al. |
| 7,374,557 B2 | 5/2008 | Conlon et al. |
| 7,390,007 B2 | 6/2008 | Helms et al. |
| 7,390,294 B2 | 6/2008 | Hassler, Jr. |
| 7,400,926 B2 | 7/2008 | Forsell |
| 7,402,134 B2 | 7/2008 | Moaddeb et al. |
| 7,402,176 B2 | 7/2008 | Malek |
| 7,410,461 B2 | 8/2008 | Lau et al. |
| 7,416,528 B2 | 8/2008 | Crawford et al. |
| 7,422,566 B2 | 9/2008 | Miethke |
| 7,429,259 B2 | 9/2008 | Cadeddu et al. |
| 7,431,692 B2 | 10/2008 | Zollinger et al. |
| 7,441,559 B2 | 10/2008 | Nelson et al. |
| 7,442,196 B2 | 10/2008 | Fisher et al. |
| 7,445,010 B2 | 11/2008 | Kugler et al. |
| 7,455,690 B2 | 11/2008 | Cartledge et al. |
| 7,458,981 B2 | 12/2008 | Fielding et al. |
| 7,468,060 B2 | 12/2008 | Utley et al. |
| 7,476,195 B2 | 1/2009 | Sayet et al. |
| 7,476,238 B2 | 1/2009 | Panjabi |
| 7,481,224 B2 | 1/2009 | Nelson et al. |
| 7,481,763 B2 | 1/2009 | Hassler, Jr. et al. |
| 7,481,841 B2 | 1/2009 | Hazebrouck et al. |
| 7,485,149 B1 | 2/2009 | White |
| 7,489,495 B2 | 2/2009 | Stevenson |
| 7,494,459 B2 | 2/2009 | Anstadt et al. |
| 7,500,484 B2 | 3/2009 | Nelson et al. |
| 7,503,922 B2 | 3/2009 | Deem et al. |
| 7,503,934 B2 | 3/2009 | Eisermann et al. |
| 7,507,252 B2 | 3/2009 | Lashinski et al. |
| 7,510,559 B2 | 3/2009 | Deem et al. |
| 7,530,981 B2 | 5/2009 | Kutsenko |
| 7,531,002 B2 | 5/2009 | Sutton et al. |
| 7,547,291 B2 | 6/2009 | Lennox et al. |
| 7,553,298 B2 | 6/2009 | Hunt et al. |
| 7,559,951 B2 | 7/2009 | DiSilvestro et al. |
| 7,561,916 B2 | 7/2009 | Hunt et al. |
| 7,562,660 B2 | 7/2009 | Saadat |
| 7,566,297 B2 | 7/2009 | Banik |
| 7,569,057 B2 | 8/2009 | Liu et al. |
| 7,578,821 B2 | 8/2009 | Fisher et al. |
| 7,584,788 B2 | 9/2009 | Baron et al. |
| 7,594,887 B2 | 9/2009 | Moaddeb et al. |
| 7,601,156 B2 | 10/2009 | Robinson |
| 7,601,162 B2 | 10/2009 | Hassler, Jr. et al. |
| 7,601,171 B2 | 10/2009 | Ainsworth et al. |
| 7,611,526 B2 | 11/2009 | Carl et al. |
| 7,615,001 B2 | 11/2009 | Jambor et al. |
| 7,615,068 B2 | 11/2009 | Timm et al. |
| 7,618,435 B2 | 11/2009 | Opolski |
| 7,621,886 B2 | 11/2009 | Burnett |
| 7,635,379 B2 | 12/2009 | Callahan et al. |
| 7,651,483 B2 | 1/2010 | Byrum et al. |
| 7,658,753 B2 | 2/2010 | Carl et al. |
| 7,666,132 B2 | 2/2010 | Forsell |
| 7,666,184 B2 | 2/2010 | Stauch |
| 7,666,210 B2 | 2/2010 | Franck et al. |
| 7,678,136 B2 | 3/2010 | Doubler et al. |
| 7,678,139 B2 | 3/2010 | Garamszegi et al. |
| 7,691,144 B2 | 4/2010 | Chang et al. |
| 7,695,512 B2 | 4/2010 | Lashinski et al. |
| 7,704,279 B2 | 4/2010 | Moskowitz et al. |
| 7,704,282 B2 | 4/2010 | Disilvestro et al. |
| 7,708,737 B2 | 5/2010 | Kraft et al. |
| 7,708,762 B2 | 5/2010 | McCarthy et al. |
| 7,708,765 B2 | 5/2010 | Carl et al. |
| 7,708,779 B2 | 5/2010 | Edie et al. |
| 7,713,287 B2 | 5/2010 | Timm et al. |
| 7,717,959 B2 | 5/2010 | William et al. |
| 7,727,141 B2 | 6/2010 | Hassler, Jr. et al. |
| 7,727,143 B2 | 6/2010 | Birk et al. |
| 7,749,224 B2 | 7/2010 | Cresina et al. |
| 7,753,913 B2 | 7/2010 | Szakelyhidi, Jr. et al. |
| 7,753,915 B1 | 7/2010 | Eksler et al. |
| 7,757,552 B2 | 7/2010 | Bogath et al. |
| 7,762,998 B2 | 7/2010 | Birk et al. |
| 7,763,053 B2 | 7/2010 | Gordon |
| 7,763,080 B2 | 7/2010 | Southworth |
| 7,766,815 B2 | 8/2010 | Ortiz |
| 7,775,099 B2 | 8/2010 | Bogath et al. |
| 7,775,215 B2 | 8/2010 | Hassler, Jr. et al. |
| 7,776,061 B2 | 8/2010 | Garner et al. |
| 7,776,068 B2 | 8/2010 | Ainsworth et al. |

(56) References Cited

U.S. PATENT DOCUMENTS

| | | |
|---|---|---|
| 7,776,075 B2 | 8/2010 | Bruneau et al. |
| 7,776,091 B2 | 8/2010 | Mastrorio et al. |
| 7,780,590 B2 | 8/2010 | Birk et al. |
| 7,787,958 B2 | 8/2010 | Stevenson |
| 7,789,912 B2 | 9/2010 | Manzi et al. |
| 7,793,583 B2 | 9/2010 | Radinger et al. |
| 7,794,447 B2 | 9/2010 | Dann et al. |
| 7,794,476 B2 | 9/2010 | Wisnewski |
| 7,798,954 B2 | 9/2010 | Birk et al. |
| 7,799,080 B2 | 9/2010 | Doty |
| 7,803,106 B2 | 9/2010 | Whalen et al. |
| 7,803,157 B2 | 9/2010 | Michelson |
| 7,811,275 B2 | 10/2010 | Birk et al. |
| 7,811,298 B2 | 10/2010 | Birk |
| 7,811,328 B2 | 10/2010 | Molz, IV et al. |
| 7,815,643 B2 | 10/2010 | Johnson et al. |
| 7,828,714 B2 | 11/2010 | Feng et al. |
| 7,828,813 B2 | 11/2010 | Mouton |
| 7,833,228 B1 | 11/2010 | Hershberger |
| 7,835,779 B2 | 11/2010 | Anderson et al. |
| 7,837,669 B2 | 11/2010 | Dann et al. |
| 7,837,691 B2 | 11/2010 | Cordes et al. |
| 7,842,036 B2 | 11/2010 | Phillips |
| 7,845,356 B2 | 12/2010 | Paraschac et al. |
| 7,846,188 B2 | 12/2010 | Moskowitz et al. |
| 7,850,660 B2 | 12/2010 | Uth et al. |
| 7,850,735 B2 | 12/2010 | Eisermann et al. |
| 7,854,769 B2 | 12/2010 | Hershberger |
| 7,862,546 B2 | 1/2011 | Conlon et al. |
| 7,862,574 B2 | 1/2011 | Deem et al. |
| 7,862,586 B2 | 1/2011 | Malek |
| 7,867,235 B2 | 1/2011 | Fell et al. |
| 7,871,368 B2 | 1/2011 | Zollinger et al. |
| 7,875,033 B2 | 1/2011 | Richter et al. |
| 7,887,566 B2 | 2/2011 | Hynes |
| 7,901,381 B2 | 3/2011 | Birk et al. |
| 7,901,419 B2 | 3/2011 | Bachmann et al. |
| 7,909,790 B2 | 3/2011 | Burnett |
| 7,909,838 B2 | 3/2011 | Deem et al. |
| 7,909,839 B2 | 3/2011 | Fields |
| 7,909,852 B2 | 3/2011 | Boomer et al. |
| 7,918,844 B2 | 4/2011 | Byrum et al. |
| 7,921,850 B2 | 4/2011 | Nelson et al. |
| 7,922,765 B2 | 4/2011 | Reiley |
| 7,927,354 B2 | 4/2011 | Edidin et al. |
| 7,927,357 B2 | 4/2011 | Sacher et al. |
| 7,931,679 B2 | 4/2011 | Heggeness |
| 7,932,825 B2 | 4/2011 | Berger |
| 7,938,836 B2 | 5/2011 | Ainsworth et al. |
| 7,938,841 B2 | 5/2011 | Sharkawy et al. |
| 7,942,903 B2 | 5/2011 | Moskowitz et al. |
| 7,942,908 B2 | 5/2011 | Sacher et al. |
| 7,947,011 B2 | 5/2011 | Birk et al. |
| 7,951,067 B2 | 5/2011 | Byrum et al. |
| 7,951,180 B2 | 5/2011 | Moskowitz et al. |
| 7,958,895 B2 | 6/2011 | Nelson et al. |
| 7,958,896 B2 | 6/2011 | Nelson et al. |
| 7,959,552 B2 | 6/2011 | Jordan et al. |
| 7,972,315 B2 | 7/2011 | Birk et al. |
| 7,972,346 B2 | 7/2011 | Bachmann et al. |
| 7,972,363 B2 | 7/2011 | Moskowitz et al. |
| 7,976,545 B2 | 7/2011 | Hershberger et al. |
| 7,983,763 B2 | 7/2011 | Stevenson et al. |
| 7,985,256 B2 | 7/2011 | Grotz et al. |
| 7,987,241 B2 | 7/2011 | St Jacques, Jr. et al. |
| 7,988,707 B2 | 8/2011 | Panjabi |
| 7,988,709 B2 | 8/2011 | Clark et al. |
| 7,993,342 B2 | 8/2011 | Malandain et al. |
| 7,993,397 B2 | 8/2011 | Lashinski et al. |
| 7,998,174 B2 | 8/2011 | Malandain et al. |
| 7,998,208 B2 | 8/2011 | Kohm et al. |
| 8,002,801 B2 | 8/2011 | Carl et al. |
| 8,002,809 B2 | 8/2011 | Baynham |
| 8,007,458 B2 | 8/2011 | Lennox et al. |
| 8,007,474 B2 | 8/2011 | Uth et al. |
| 8,007,479 B2 | 8/2011 | Birk et al. |
| 8,011,308 B2 | 9/2011 | Picchio |
| 8,012,162 B2 | 9/2011 | Bachmann |
| 8,016,745 B2 | 9/2011 | Hassler, Jr. et al. |
| 8,016,837 B2 * | 9/2011 | Giger ................ A61B 17/8076 606/105 |
| 8,016,860 B2 | 9/2011 | Carl et al. |
| 8,026,729 B2 | 9/2011 | Kroh et al. |
| 8,029,477 B2 | 10/2011 | Byrum et al. |
| 8,029,567 B2 | 10/2011 | Edidin et al. |
| 8,034,080 B2 | 10/2011 | Malandain et al. |
| 8,037,871 B2 | 10/2011 | McClendon |
| 8,038,680 B2 | 10/2011 | Ainsworth et al. |
| 8,038,698 B2 | 10/2011 | Edidin et al. |
| 8,043,206 B2 | 10/2011 | Birk |
| 8,043,290 B2 | 10/2011 | Harrison et al. |
| 8,043,299 B2 | 10/2011 | Conway |
| 8,043,338 B2 | 10/2011 | Dant |
| 8,043,345 B2 | 10/2011 | Carl et al. |
| 8,048,169 B2 | 11/2011 | Burnett et al. |
| 8,057,473 B2 | 11/2011 | Orsak et al. |
| 8,057,513 B2 | 11/2011 | Kohm et al. |
| 8,066,650 B2 | 11/2011 | Lee et al. |
| 8,070,670 B2 | 12/2011 | Deem et al. |
| 8,070,671 B2 | 12/2011 | Deem et al. |
| 8,070,695 B2 | 12/2011 | Gupta et al. |
| 8,070,813 B2 | 12/2011 | Grotz et al. |
| 8,074,654 B2 | 12/2011 | Paraschac et al. |
| 8,075,577 B2 | 12/2011 | Deem et al. |
| 8,079,974 B2 | 12/2011 | Stergiopulos |
| 8,079,989 B2 | 12/2011 | Birk et al. |
| 8,080,022 B2 | 12/2011 | Deem et al. |
| 8,080,025 B2 | 12/2011 | Deem et al. |
| 8,088,166 B2 | 1/2012 | Makower et al. |
| 8,092,459 B2 | 1/2012 | Malandain |
| 8,092,499 B1 | 1/2012 | Roth |
| 8,095,317 B2 | 1/2012 | Ekseth et al. |
| 8,096,302 B2 | 1/2012 | Nelson et al. |
| 8,096,938 B2 | 1/2012 | Forsell |
| 8,096,995 B2 | 1/2012 | Kohm et al. |
| 8,097,018 B2 | 1/2012 | Malandain et al. |
| 8,097,038 B2 | 1/2012 | Malek |
| 8,100,819 B2 | 1/2012 | Banik |
| 8,100,943 B2 | 1/2012 | Malandain et al. |
| 8,100,967 B2 | 1/2012 | Makower et al. |
| 8,105,360 B1 | 1/2012 | Connor |
| 8,105,363 B2 | 1/2012 | Fielding et al. |
| 8,105,364 B2 | 1/2012 | McCarthy et al. |
| 8,109,974 B2 | 2/2012 | Boomer et al. |
| 8,114,158 B2 | 2/2012 | Carl et al. |
| 8,123,765 B2 | 2/2012 | Deem et al. |
| 8,123,805 B2 | 2/2012 | Makower et al. |
| 8,128,628 B2 | 3/2012 | Freid et al. |
| 8,133,280 B2 | 3/2012 | Voellmicke et al. |
| 8,137,349 B2 | 3/2012 | Soubeiran |
| 8,137,366 B2 | 3/2012 | Deem et al. |
| 8,137,367 B2 | 3/2012 | Deem et al. |
| 8,142,454 B2 | 3/2012 | Harrison et al. |
| 8,142,494 B2 | 3/2012 | Rahdert et al. |
| 8,147,517 B2 | 4/2012 | Trieu et al. |
| 8,147,549 B2 | 4/2012 | Metcalf, Jr. et al. |
| 8,157,841 B2 | 4/2012 | Malandain et al. |
| 8,162,897 B2 | 4/2012 | Byrum |
| 8,162,979 B2 | 4/2012 | Sachs et al. |
| 8,163,013 B2 | 4/2012 | Machold et al. |
| 8,177,789 B2 | 5/2012 | Magill et al. |
| 8,182,411 B2 | 5/2012 | Dlugos |
| 8,187,324 B2 | 5/2012 | Webler et al. |
| 8,197,544 B1 | 6/2012 | Manzi et al. |
| 8,202,305 B2 | 6/2012 | Reiley |
| 8,211,127 B2 | 7/2012 | Uth et al. |
| 8,211,149 B2 | 7/2012 | Justis |
| 8,211,151 B2 | 7/2012 | Schwab et al. |
| 8,211,179 B2 | 7/2012 | Molz, IV et al. |
| 8,216,275 B2 | 7/2012 | Fielding et al. |
| 8,221,420 B2 | 7/2012 | Keller |
| 8,226,690 B2 | 7/2012 | Altarac et al. |
| 8,236,002 B2 | 8/2012 | Fortin et al. |
| 8,241,292 B2 | 8/2012 | Collazo |

(56) References Cited

U.S. PATENT DOCUMENTS

| | | |
|---|---|---|
| 8,241,293 B2 | 8/2012 | Stone et al. |
| 8,241,331 B2 | 8/2012 | Arnin |
| 8,246,630 B2 | 8/2012 | Manzi et al. |
| 8,251,888 B2 | 8/2012 | Roslin et al. |
| 8,252,063 B2 | 8/2012 | Stauch |
| 8,257,370 B2 | 9/2012 | Moskowitz et al. |
| 8,257,442 B2 | 9/2012 | Edie et al. |
| 8,263,024 B2 | 9/2012 | Wan et al. |
| 8,267,969 B2 | 9/2012 | Altarac et al. |
| 8,273,112 B2 | 9/2012 | Garamszegi et al. |
| 8,278,941 B2 | 10/2012 | Kroh et al. |
| 8,282,671 B2 * | 10/2012 | Connor ............. A61B 17/7016 606/246 |
| 8,287,540 B2 | 10/2012 | LeCronier et al. |
| 8,298,133 B2 | 10/2012 | Wiley et al. |
| 8,298,240 B2 * | 10/2012 | Giger ................ A61B 17/8076 606/90 |
| 8,308,779 B2 | 11/2012 | Reiley |
| 8,313,423 B2 | 11/2012 | Forsell |
| 8,316,856 B2 | 11/2012 | Nelson et al. |
| 8,317,761 B2 | 11/2012 | Birk et al. |
| 8,317,802 B1 | 11/2012 | Manzi et al. |
| 8,323,290 B2 | 12/2012 | Metzger et al. |
| 8,326,435 B2 | 12/2012 | Stevenson |
| 8,328,807 B2 | 12/2012 | Brigido |
| 8,328,854 B2 | 12/2012 | Baynham et al. |
| 8,333,204 B2 | 12/2012 | Saadat |
| 8,333,790 B2 | 12/2012 | Timm et al. |
| 8,353,913 B2 | 1/2013 | Moskowitz et al. |
| 8,357,169 B2 | 1/2013 | Henniges et al. |
| 8,357,182 B2 | 1/2013 | Seme |
| 8,357,183 B2 | 1/2013 | Seme et al. |
| 8,360,955 B2 | 1/2013 | Sayet et al. |
| 8,366,628 B2 | 2/2013 | Denker et al. |
| 8,372,078 B2 | 2/2013 | Collazo |
| 8,382,652 B2 | 2/2013 | Sayet et al. |
| 8,386,018 B2 | 2/2013 | Stauch et al. |
| 8,388,667 B2 | 3/2013 | Reiley et al. |
| 8,394,124 B2 | 3/2013 | Biyani |
| 8,394,143 B2 | 3/2013 | Grotz et al. |
| 8,403,958 B2 | 3/2013 | Schwab |
| 8,409,203 B2 | 4/2013 | Birk et al. |
| 8,409,281 B2 | 4/2013 | Makower et al. |
| 8,414,584 B2 | 4/2013 | Brigido |
| 8,414,648 B2 | 4/2013 | Reiley |
| 8,419,755 B2 | 4/2013 | Deem et al. |
| 8,419,801 B2 | 4/2013 | DiSilvestro et al. |
| 8,425,570 B2 | 4/2013 | Reiley |
| 8,425,608 B2 | 4/2013 | Dewey et al. |
| 8,433,519 B2 | 4/2013 | Ekseth et al. |
| 8,435,268 B2 | 5/2013 | Thompson et al. |
| 8,439,915 B2 | 5/2013 | Harrison et al. |
| 8,439,926 B2 | 5/2013 | Bojarski et al. |
| 8,444,693 B2 | 5/2013 | Reiley |
| 8,449,553 B2 | 5/2013 | Kam et al. |
| 8,449,580 B2 | 5/2013 | Voellmicke et al. |
| 8,454,695 B2 | 6/2013 | Grotz et al. |
| 8,469,908 B2 | 6/2013 | Asfora |
| 8,469,978 B2 | 6/2013 | Fobi et al. |
| 8,470,003 B2 | 6/2013 | Voellmicke et al. |
| 8,470,004 B2 | 6/2013 | Reiley |
| 8,475,354 B2 | 7/2013 | Phillips et al. |
| 8,475,356 B2 | 7/2013 | Feng et al. |
| 8,475,499 B2 | 7/2013 | Cournoyer et al. |
| 8,480,554 B2 | 7/2013 | Phillips et al. |
| 8,480,668 B2 | 7/2013 | Fernandez et al. |
| 8,480,741 B2 | 7/2013 | Grotz et al. |
| 8,486,070 B2 | 7/2013 | Morgan et al. |
| 8,486,076 B2 | 7/2013 | Chavarria et al. |
| 8,486,110 B2 | 7/2013 | Fielding et al. |
| 8,486,113 B2 | 7/2013 | Malek |
| 8,486,147 B2 | 7/2013 | de Villiers et al. |
| 8,491,589 B2 | 7/2013 | Fisher et al. |
| 8,494,805 B2 | 7/2013 | Roche et al. |
| 8,496,662 B2 | 7/2013 | Novak et al. |
| 8,500,810 B2 | 8/2013 | Mastrorio et al. |
| 8,506,517 B2 | 8/2013 | Stergiopulos |
| 8,506,569 B2 | 8/2013 | Keefer et al. |
| 8,517,973 B2 | 8/2013 | Burnett |
| 8,518,062 B2 | 8/2013 | Cole et al. |
| 8,518,086 B2 | 8/2013 | Seme et al. |
| 8,522,790 B2 | 9/2013 | Nelson et al. |
| 8,523,865 B2 | 9/2013 | Reglos et al. |
| 8,523,866 B2 | 9/2013 | Sidebotham et al. |
| 8,523,883 B2 | 9/2013 | Saadat |
| 8,529,474 B2 | 9/2013 | Gupta et al. |
| 8,529,606 B2 | 9/2013 | Alamin et al. |
| 8,529,607 B2 | 9/2013 | Alamin et al. |
| 8,529,630 B2 | 9/2013 | Bojarski et al. |
| 8,545,384 B2 | 10/2013 | Forsell |
| 8,545,508 B2 | 10/2013 | Collazo |
| 8,545,814 B2 | 10/2013 | Contag et al. |
| 8,551,092 B2 | 10/2013 | Morgan et al. |
| 8,551,142 B2 | 10/2013 | Altarac et al. |
| 8,551,422 B2 | 10/2013 | Wan et al. |
| 8,556,901 B2 | 10/2013 | Anthony et al. |
| 8,556,911 B2 | 10/2013 | Mehta et al. |
| 8,556,975 B2 | 10/2013 | Ciupik et al. |
| 8,562,653 B2 | 10/2013 | Alamin et al. |
| 8,568,416 B2 | 10/2013 | Schmitz et al. |
| 8,568,457 B2 | 10/2013 | Hunziker |
| 8,574,267 B2 | 11/2013 | Linares |
| 8,579,919 B2 | 11/2013 | Bolduc et al. |
| 8,579,979 B2 | 11/2013 | Edie et al. |
| 8,585,595 B2 | 11/2013 | Heilman |
| 8,585,702 B2 | 11/2013 | Orsak et al. |
| 8,585,738 B2 | 11/2013 | Linares |
| 8,585,740 B1 | 11/2013 | Ross et al. |
| 8,591,549 B2 | 11/2013 | Lange |
| 8,597,362 B2 | 12/2013 | Shenoy et al. |
| 8,613,749 B2 | 12/2013 | Deem et al. |
| 8,613,758 B2 | 12/2013 | Linares |
| 8,617,212 B2 | 12/2013 | Linares |
| 8,617,220 B2 | 12/2013 | Skaggs |
| 8,617,243 B2 | 12/2013 | Eisermann et al. |
| 8,622,936 B2 | 1/2014 | Schenberger et al. |
| 8,623,036 B2 | 1/2014 | Harrison et al. |
| 8,623,042 B2 | 1/2014 | Roslin et al. |
| 8,623,056 B2 | 1/2014 | Linares |
| 8,632,544 B2 | 1/2014 | Haaja et al. |
| 8,632,547 B2 | 1/2014 | Maxson et al. |
| 8,632,548 B2 | 1/2014 | Soubeiran |
| 8,632,563 B2 | 1/2014 | Nagase et al. |
| 8,632,594 B2 | 1/2014 | Williams et al. |
| 8,636,770 B2 | 1/2014 | Hestad et al. |
| 8,636,771 B2 | 1/2014 | Butler et al. |
| 8,636,802 B2 | 1/2014 | Serhan et al. |
| 8,641,719 B2 | 2/2014 | Gephart et al. |
| 8,641,723 B2 | 2/2014 | Connor |
| 8,652,175 B2 | 2/2014 | Timm et al. |
| 8,657,765 B2 | 2/2014 | Asfora |
| 8,657,856 B2 | 2/2014 | Gephart et al. |
| 8,657,885 B2 | 2/2014 | Burnett et al. |
| 8,663,139 B2 | 3/2014 | Asfora |
| 8,663,140 B2 | 3/2014 | Asfora |
| 8,663,285 B2 | 3/2014 | Dall et al. |
| 8,663,287 B2 | 3/2014 | Butler et al. |
| 8,663,338 B2 | 3/2014 | Burnett et al. |
| 8,668,719 B2 | 3/2014 | Alamin et al. |
| 8,673,001 B2 | 3/2014 | Cartledge et al. |
| 8,679,161 B2 | 3/2014 | Malandain et al. |
| 8,690,858 B2 | 4/2014 | Machold et al. |
| 8,707,959 B2 | 4/2014 | Paraschac et al. |
| 8,709,090 B2 | 4/2014 | Makower et al. |
| 8,715,243 B2 | 5/2014 | Uth et al. |
| 8,715,290 B2 | 5/2014 | Fisher et al. |
| 8,721,570 B2 | 5/2014 | Gupta et al. |
| 8,721,643 B2 | 5/2014 | Morgan et al. |
| 8,728,125 B2 | 5/2014 | Bruneau et al. |
| 8,734,318 B2 | 5/2014 | Forsell |
| 8,734,516 B2 | 5/2014 | Moskowitz et al. |
| 8,734,519 B2 | 5/2014 | de Villiers et al. |
| 8,747,444 B2 | 6/2014 | Moskowitz et al. |
| 8,752,552 B2 | 6/2014 | Nelson et al. |

(56) References Cited

U.S. PATENT DOCUMENTS

| | | |
|---|---|---|
| 8,758,303 B2 | 6/2014 | Uth et al. |
| 8,758,347 B2 | 6/2014 | Weiner et al. |
| 8,758,355 B2 | 6/2014 | Fisher et al. |
| 8,758,372 B2 | 6/2014 | Cartledge et al. |
| 8,762,308 B2 | 6/2014 | Najarian et al. |
| 8,764,713 B2 | 7/2014 | Uth et al. |
| 8,771,272 B2 | 7/2014 | LeCronier et al. |
| 8,777,947 B2 | 7/2014 | Zahrly et al. |
| 8,777,995 B2 | 7/2014 | McClintock et al. |
| 8,781,744 B2 | 7/2014 | Ekseth et al. |
| 8,784,482 B2 | 7/2014 | Rahdert et al. |
| 8,790,343 B2 | 7/2014 | McClellan et al. |
| 8,790,380 B2 | 7/2014 | Buttermann |
| 8,790,409 B2 | 7/2014 | Van den Heuvel et al. |
| 8,794,243 B2 | 8/2014 | Deem et al. |
| 8,795,339 B2 | 8/2014 | Boomer et al. |
| 8,801,795 B2 | 8/2014 | Makower et al. |
| 8,808,206 B2 | 8/2014 | Asfora |
| 8,813,727 B2 | 8/2014 | McClendon |
| 8,814,869 B2 | 8/2014 | Freid et al. |
| 8,828,058 B2 | 9/2014 | Elsebaie et al. |
| 8,828,087 B2 | 9/2014 | Stone et al. |
| 8,840,623 B2 | 9/2014 | Reiley |
| 8,840,651 B2 | 9/2014 | Reiley |
| 8,845,692 B2 | 9/2014 | Wisnewski |
| 8,845,724 B2 | 9/2014 | Shenoy et al. |
| 8,864,717 B2 | 10/2014 | Conlon et al. |
| 8,864,823 B2 | 10/2014 | Cartledge et al. |
| 8,870,881 B2 | 10/2014 | Rezach et al. |
| 8,870,918 B2 | 10/2014 | Boomer et al. |
| 8,870,959 B2 | 10/2014 | Arnin |
| 8,882,699 B2 | 11/2014 | Burnett |
| 8,882,830 B2 | 11/2014 | Cartledge et al. |
| 8,888,672 B2 | 11/2014 | Phillips et al. |
| 8,888,673 B2 | 11/2014 | Phillips et al. |
| 8,894,663 B2 | 11/2014 | Giger et al. |
| 8,915,915 B2 | 12/2014 | Harrison et al. |
| 8,915,917 B2 | 12/2014 | Doherty et al. |
| 8,920,422 B2 | 12/2014 | Homeier et al. |
| 8,932,247 B2 | 1/2015 | Stergiopulos |
| 8,945,188 B2 | 2/2015 | Rezach et al. |
| 8,945,210 B2 | 2/2015 | Cartledge et al. |
| 8,956,407 B2 | 2/2015 | Macoviak et al. |
| 8,961,386 B2 | 2/2015 | Phillips et al. |
| 8,961,521 B2 | 2/2015 | Keefer et al. |
| 8,961,567 B2 | 2/2015 | Hunziker |
| 8,968,402 B2 | 3/2015 | Myers et al. |
| 8,968,406 B2 | 3/2015 | Arnin |
| 8,986,348 B2 | 3/2015 | Reiley |
| 8,992,527 B2 | 3/2015 | Guichet |
| 9,005,251 B2 | 4/2015 | Heggeness |
| 9,005,293 B2 | 4/2015 | Moskowitz et al. |
| 9,005,298 B2 | 4/2015 | Makower et al. |
| 9,011,491 B2 | 4/2015 | Carl et al. |
| 9,015,057 B2 | 4/2015 | Phillips et al. |
| 9,022,917 B2 | 5/2015 | Kasic et al. |
| 9,028,550 B2 | 5/2015 | Shulock et al. |
| 9,033,957 B2 | 5/2015 | Cadeddu et al. |
| 9,033,988 B2 | 5/2015 | Gephart et al. |
| 9,034,016 B2 | 5/2015 | Panjabi |
| 9,044,218 B2 | 6/2015 | Young |
| 9,060,810 B2 | 6/2015 | Kercher et al. |
| 9,060,844 B2 | 6/2015 | Kagan et al. |
| 9,072,530 B2 | 7/2015 | Mehta et al. |
| 9,072,606 B2 | 7/2015 | Lucas et al. |
| 9,078,703 B2 | 7/2015 | Arnin |
| 9,084,632 B2 | 7/2015 | Orsak et al. |
| 9,089,348 B2 | 7/2015 | Chavarria et al. |
| 9,095,436 B2 | 8/2015 | Boyden et al. |
| 9,095,437 B2 | 8/2015 | Boyden et al. |
| 9,101,422 B2 | 8/2015 | Freid et al. |
| 9,101,427 B2 | 8/2015 | Globerman et al. |
| 9,107,706 B2 | 8/2015 | Alamin et al. |
| 9,113,967 B2 | 8/2015 | Soubeiran |
| 9,114,016 B2 | 8/2015 | Shenoy et al. |
| 9,125,746 B2 | 9/2015 | Clifford et al. |
| 9,138,266 B2 | 9/2015 | Stauch |
| 9,144,482 B2 | 9/2015 | Sayet |
| 9,155,565 B2 | 10/2015 | Boomer et al. |
| 9,161,856 B2 | 10/2015 | Nelson et al. |
| 9,168,071 B2 | 10/2015 | Seme et al. |
| 9,168,076 B2 | 10/2015 | Patty et al. |
| 9,173,681 B2 | 11/2015 | Seme |
| 9,173,715 B2 | 11/2015 | Baumgartner |
| 9,186,158 B2 | 11/2015 | Anthony et al. |
| 9,186,185 B2 | 11/2015 | Hestad et al. |
| 9,198,771 B2 | 12/2015 | Ciupik |
| 9,204,899 B2 | 12/2015 | Buttermann |
| 9,204,908 B2 | 12/2015 | Buttermann |
| 9,220,536 B2 | 12/2015 | Skaggs |
| 9,226,783 B2 | 1/2016 | Brigido |
| 9,242,070 B2 | 1/2016 | Tieu |
| 9,259,243 B2 | 2/2016 | Giger et al. |
| 9,272,159 B2 | 3/2016 | Phillips et al. |
| 9,278,004 B2 | 3/2016 | Shenoy et al. |
| 9,278,046 B2 | 3/2016 | Asfora |
| 9,282,997 B2 | 3/2016 | Hunziker |
| 9,301,792 B2 | 4/2016 | Henniges et al. |
| 9,301,854 B2 | 4/2016 | Moskowitz et al. |
| 9,308,089 B2 | 4/2016 | Vicatos et al. |
| 9,308,387 B2 | 4/2016 | Phillips et al. |
| 9,320,618 B2 | 4/2016 | Schmitz et al. |
| 9,326,728 B2 | 5/2016 | Demir et al. |
| 9,333,009 B2 | 5/2016 | Kroll et al. |
| 9,339,197 B2 | 5/2016 | Griswold et al. |
| 9,339,300 B2 | 5/2016 | Kantelhardt |
| 9,339,307 B2 | 5/2016 | McClintock et al. |
| 9,339,312 B2 | 5/2016 | Doherty et al. |
| 9,358,044 B2 | 6/2016 | Seme et al. |
| 9,364,267 B2 | 6/2016 | Northcutt et al. |
| 9,370,388 B2 | 6/2016 | Globerman et al. |
| 9,393,123 B2 | 7/2016 | Lucas et al. |
| 9,408,644 B2 | 8/2016 | Zahrly et al. |
| 9,421,347 B2 | 8/2016 | Burnett |
| 9,427,267 B2 | 8/2016 | Homeier et al. |
| 9,439,744 B2 | 9/2016 | Forsell |
| 9,439,797 B2 | 9/2016 | Baym et al. |
| 9,445,848 B2 | 9/2016 | Anderson et al. |
| 9,451,997 B2 | 9/2016 | Carl et al. |
| 9,456,953 B2 | 10/2016 | Asfora |
| 9,474,612 B2 | 10/2016 | Haaja et al. |
| 9,492,199 B2 | 11/2016 | Orsak et al. |
| 9,492,276 B2 | 11/2016 | Lee et al. |
| 9,498,258 B2 | 11/2016 | Boomer et al. |
| 9,498,366 B2 | 11/2016 | Burnett et al. |
| 9,510,834 B2 | 12/2016 | Burnett et al. |
| 9,532,804 B2 | 1/2017 | Clifford et al. |
| 9,561,062 B2 | 2/2017 | Hayes et al. |
| 9,561,063 B2 | 2/2017 | Reiley |
| 9,572,588 B2 | 2/2017 | Fisher et al. |
| 9,572,746 B2 | 2/2017 | Asfora |
| 9,572,910 B2 | 2/2017 | Messersmith et al. |
| 9,579,110 B2 | 2/2017 | Bojarski et al. |
| 9,579,203 B2 | 2/2017 | Soubeiran |
| 9,603,605 B2 | 3/2017 | Collazo |
| 9,603,713 B2 | 3/2017 | Moskowitz et al. |
| 9,610,161 B2 | 4/2017 | Macoviak et al. |
| 9,622,875 B2 | 4/2017 | Moskowitz et al. |
| 9,642,735 B2 | 5/2017 | Burnett |
| 9,655,651 B2 | 5/2017 | Panjabi |
| 9,668,868 B2 | 6/2017 | Shenoy et al. |
| 9,687,243 B2 | 6/2017 | Burnett et al. |
| 9,687,414 B2 | 6/2017 | Asfora |
| 9,693,867 B2 | 7/2017 | Lucas et al. |
| 9,700,419 B2 | 7/2017 | Clifford et al. |
| 9,700,450 B2 | 7/2017 | Burnett |
| 9,717,537 B2 | 8/2017 | Gordon |
| 9,724,135 B2 | 8/2017 | Koch et al. |
| 9,724,265 B2 | 8/2017 | Asfora |
| 9,730,738 B2 | 8/2017 | Gephart et al. |
| 9,743,969 B2 | 8/2017 | Reiley |
| 9,782,206 B2 | 10/2017 | Mueckter et al. |
| 9,795,410 B2 | 10/2017 | Shenoy et al. |
| 9,814,600 B2 | 11/2017 | Shulock et al. |

(56) References Cited

U.S. PATENT DOCUMENTS

| | | |
|---|---|---|
| 9,820,789 B2 | 11/2017 | Reiley |
| 9,826,987 B2 | 11/2017 | Keefer et al. |
| 9,833,291 B2 | 12/2017 | Baumgartner |
| 9,848,894 B2 | 12/2017 | Burley et al. |
| 9,848,993 B2 | 12/2017 | Moskowitz et al. |
| 9,861,376 B2 | 1/2018 | Chavarria et al. |
| 9,861,390 B2 | 1/2018 | Hunziker |
| 9,861,404 B2 | 1/2018 | Reiley |
| 9,867,719 B2 | 1/2018 | Moskowitz et al. |
| 2001/0011543 A1 | 8/2001 | Forsell |
| 2002/0019580 A1 | 2/2002 | Lau et al. |
| 2002/0050112 A1 | 5/2002 | Koch et al. |
| 2002/0072758 A1 | 6/2002 | Reo et al. |
| 2002/0164905 A1 | 11/2002 | Bryant |
| 2003/0019498 A1 | 1/2003 | Forsell |
| 2003/0040671 A1 | 2/2003 | Somogyi et al. |
| 2003/0066536 A1 | 4/2003 | Forsell |
| 2003/0109881 A1* | 6/2003 | Shirado .............. A61B 17/7022 606/330 |
| 2003/0114731 A1 | 6/2003 | Cadeddu et al. |
| 2003/0187447 A1 | 10/2003 | Ferrante et al. |
| 2003/0208212 A1 | 11/2003 | Cigaina |
| 2003/0220643 A1 | 11/2003 | Ferree |
| 2003/0220644 A1 | 11/2003 | Thelen et al. |
| 2004/0006342 A1 | 1/2004 | Altarac et al. |
| 2004/0011137 A1 | 1/2004 | Hnat et al. |
| 2004/0011365 A1 | 1/2004 | Govari et al. |
| 2004/0019353 A1 | 1/2004 | Freid et al. |
| 2004/0023623 A1 | 2/2004 | Stauch et al. |
| 2004/0055610 A1 | 3/2004 | Forsell |
| 2004/0064030 A1 | 4/2004 | Forsell |
| 2004/0068205 A1 | 4/2004 | Zogbi et al. |
| 2004/0092939 A1 | 5/2004 | Freid et al. |
| 2004/0098121 A1 | 5/2004 | Opolski |
| 2004/0116773 A1 | 6/2004 | Furness et al. |
| 2004/0133219 A1 | 7/2004 | Forsell |
| 2004/0138725 A1 | 7/2004 | Forsell |
| 2004/0153106 A1 | 8/2004 | Dudai |
| 2004/0158254 A1 | 8/2004 | Eisermann |
| 2004/0172040 A1 | 9/2004 | Heggeness |
| 2004/0173222 A1 | 9/2004 | Kim |
| 2004/0193266 A1 | 9/2004 | Meyer |
| 2004/0220567 A1 | 11/2004 | Eisermann et al. |
| 2004/0220668 A1 | 11/2004 | Eisermann et al. |
| 2004/0230307 A1 | 11/2004 | Eisermann |
| 2004/0250820 A1 | 12/2004 | Forsell |
| 2004/0260287 A1 | 12/2004 | Ferree |
| 2004/0260319 A1 | 12/2004 | Egle |
| 2005/0002984 A1 | 1/2005 | Byrum et al. |
| 2005/0043802 A1 | 2/2005 | Eisermann et al. |
| 2005/0055025 A1 | 3/2005 | Zacouto et al. |
| 2005/0070937 A1 | 3/2005 | Jambor et al. |
| 2005/0080427 A1 | 4/2005 | Govari et al. |
| 2005/0080439 A1 | 4/2005 | Carson et al. |
| 2005/0090823 A1 | 4/2005 | Bartimus |
| 2005/0096750 A1 | 5/2005 | Kagan et al. |
| 2005/0131352 A1 | 6/2005 | Conlon et al. |
| 2005/0159754 A1 | 7/2005 | Odrich |
| 2005/0159755 A1 | 7/2005 | Odrich |
| 2005/0165440 A1 | 7/2005 | Cancel et al. |
| 2005/0171543 A1 | 8/2005 | Timm et al. |
| 2005/0177164 A1 | 8/2005 | Walters et al. |
| 2005/0182400 A1 | 8/2005 | White |
| 2005/0182401 A1 | 8/2005 | Timm et al. |
| 2005/0182412 A1 | 8/2005 | Johnson et al. |
| 2005/0192629 A1 | 9/2005 | Saadat et al. |
| 2005/0222489 A1 | 10/2005 | Rahdert et al. |
| 2005/0234289 A1 | 10/2005 | Anstadt et al. |
| 2005/0234448 A1 | 10/2005 | McCarthy |
| 2005/0234462 A1 | 10/2005 | Hershberger |
| 2005/0246034 A1 | 11/2005 | Soubeiran |
| 2005/0251109 A1 | 11/2005 | Soubeiran |
| 2005/0261779 A1 | 11/2005 | Meyer |
| 2005/0272976 A1 | 12/2005 | Tanaka et al. |
| 2005/0288672 A1 | 12/2005 | Ferree |
| 2006/0020278 A1 | 1/2006 | Burnett et al. |
| 2006/0036246 A1 | 2/2006 | Carl et al. |
| 2006/0036251 A1 | 2/2006 | Reiley |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1* | 3/2006 | Gordon .............. A61B 17/7016 606/86 A |
| 2006/0058790 A1 | 3/2006 | Carl et al. |
| 2006/0058792 A1 | 3/2006 | Hynes |
| 2006/0079897 A1 | 4/2006 | Harrison et al. |
| 2006/0116757 A1 | 6/2006 | Lashinski et al. |
| 2006/0124140 A1 | 6/2006 | Forsell |
| 2006/0136062 A1 | 6/2006 | DiNello et al. |
| 2006/0142634 A1 | 6/2006 | Anstadt et al. |
| 2006/0142767 A1 | 6/2006 | Green et al. |
| 2006/0155279 A1 | 7/2006 | Ogilvie |
| 2006/0155347 A1 | 7/2006 | Forsell |
| 2006/0184240 A1 | 8/2006 | Jimenez et al. |
| 2006/0184248 A1 | 8/2006 | Edidin et al. |
| 2006/0195088 A1 | 8/2006 | Sacher et al. |
| 2006/0195102 A1 | 8/2006 | Malandain |
| 2006/0204156 A1 | 9/2006 | Takehara et al. |
| 2006/0211909 A1 | 9/2006 | Anstadt et al. |
| 2006/0235299 A1 | 10/2006 | Martinelli |
| 2006/0235424 A1* | 10/2006 | Vitale ................ A61B 17/7216 606/90 |
| 2006/0241746 A1 | 10/2006 | Shaoulian et al. |
| 2006/0249914 A1 | 11/2006 | Dulin |
| 2006/0252983 A1 | 11/2006 | Lembo et al. |
| 2006/0271107 A1 | 11/2006 | Harrison et al. |
| 2006/0276812 A1 | 12/2006 | Hill et al. |
| 2006/0282073 A1 | 12/2006 | Simanovsky |
| 2006/0289014 A1 | 12/2006 | Purdy et al. |
| 2006/0293671 A1 | 12/2006 | Heggeness |
| 2006/0293683 A1 | 12/2006 | Stauch |
| 2007/0010814 A1 | 1/2007 | Stauch |
| 2007/0015955 A1 | 1/2007 | Tsonton |
| 2007/0021644 A1 | 1/2007 | Woolson et al. |
| 2007/0031131 A1 | 2/2007 | Griffitts |
| 2007/0043376 A1 | 2/2007 | Leatherbury et al. |
| 2007/0050030 A1 | 3/2007 | Kim |
| 2007/0055237 A1 | 3/2007 | Edidin et al. |
| 2007/0055368 A1 | 3/2007 | Rhee et al. |
| 2007/0118215 A1 | 5/2007 | Moaddeb |
| 2007/0135913 A1 | 6/2007 | Moaddeb et al. |
| 2007/0161993 A1* | 7/2007 | Lowery .............. A61B 17/7055 606/279 |
| 2007/0162032 A1 | 7/2007 | Johnson et al. |
| 2007/0173837 A1 | 7/2007 | Chan et al. |
| 2007/0173869 A1 | 7/2007 | Gannoe et al. |
| 2007/0179493 A1 | 8/2007 | Kim |
| 2007/0213751 A1 | 9/2007 | Scirica et al. |
| 2007/0239159 A1 | 10/2007 | Altarac et al. |
| 2007/0250084 A1 | 10/2007 | Sharkawy et al. |
| 2007/0255088 A1 | 11/2007 | Jacobson et al. |
| 2007/0256693 A1 | 11/2007 | Paraschac et al. |
| 2007/0260270 A1 | 11/2007 | Assell et al. |
| 2007/0264605 A1 | 11/2007 | Belfor et al. |
| 2007/0270631 A1 | 11/2007 | Nelson et al. |
| 2007/0276369 A1 | 11/2007 | Allard et al. |
| 2007/0276372 A1 | 11/2007 | Malandain et al. |
| 2007/0276373 A1 | 11/2007 | Malandain |
| 2007/0276493 A1 | 11/2007 | Malandain et al. |
| 2007/0288024 A1 | 12/2007 | Gollogly |
| 2007/0288183 A1 | 12/2007 | Bulkes et al. |
| 2008/0015577 A1 | 1/2008 | Loeb |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0033431 A1 | 2/2008 | Jung et al. |
| 2008/0033436 A1 | 2/2008 | Song et al. |
| 2008/0051784 A1 | 2/2008 | Gollogly |
| 2008/0051788 A1 | 2/2008 | Schwab |
| 2008/0051895 A1 | 2/2008 | Malandain et al. |
| 2008/0058936 A1 | 3/2008 | Malandain et al. |
| 2008/0058937 A1 | 3/2008 | Malandain et al. |
| 2008/0065077 A1 | 3/2008 | Ferree |
| 2008/0065215 A1 | 3/2008 | Reiley |

(56) References Cited

U.S. PATENT DOCUMENTS

| | | |
|---|---|---|
| 2008/0066764 A1 | 3/2008 | Paraschac et al. |
| 2008/0071275 A1 | 3/2008 | Ferree |
| 2008/0071276 A1 | 3/2008 | Ferree |
| 2008/0082118 A1 | 4/2008 | Edidin et al. |
| 2008/0082167 A1 | 4/2008 | Edidin et al. |
| 2008/0083413 A1 | 4/2008 | Forsell |
| 2008/0086128 A1 | 4/2008 | Lewis |
| 2008/0091059 A1 | 4/2008 | Machold et al. |
| 2008/0097487 A1 | 4/2008 | Pool et al. |
| 2008/0097523 A1 | 4/2008 | Bolduc et al. |
| 2008/0108995 A1 | 5/2008 | Conway et al. |
| 2008/0140188 A1 | 6/2008 | Rahdert et al. |
| 2008/0140200 A1* | 6/2008 | Heinz ............... A61B 17/7055 623/17.11 |
| 2008/0147139 A1 | 6/2008 | Barrett et al. |
| 2008/0147192 A1 | 6/2008 | Edidin et al. |
| 2008/0161933 A1 | 7/2008 | Grotz et al. |
| 2008/0167685 A1 | 7/2008 | Allard et al. |
| 2008/0172063 A1 | 7/2008 | Taylor |
| 2008/0177319 A1 | 7/2008 | Schwab |
| 2008/0177326 A1 | 7/2008 | Thompson |
| 2008/0195156 A1 | 8/2008 | Ainsworth et al. |
| 2008/0226563 A1 | 9/2008 | Contag et al. |
| 2008/0228186 A1 | 9/2008 | Gall et al. |
| 2008/0255615 A1 | 10/2008 | Vittur et al. |
| 2008/0272928 A1 | 11/2008 | Shuster |
| 2008/0275552 A1 | 11/2008 | Makower et al. |
| 2008/0275555 A1 | 11/2008 | Makower et al. |
| 2008/0275557 A1 | 11/2008 | Makower et al. |
| 2008/0275567 A1 | 11/2008 | Makower et al. |
| 2008/0293995 A1 | 11/2008 | Moaddeb et al. |
| 2009/0012565 A1* | 1/2009 | Sachs ............... A61B 17/7041 606/246 |
| 2009/0076597 A1 | 3/2009 | Dahlgren et al. |
| 2009/0082815 A1 | 3/2009 | Zylber et al. |
| 2009/0088766 A1 | 4/2009 | Magill et al. |
| 2009/0088803 A1 | 4/2009 | Justis et al. |
| 2009/0093820 A1 | 4/2009 | Trieu et al. |
| 2009/0093890 A1 | 4/2009 | Gelbart |
| 2009/0112207 A1 | 4/2009 | Walker et al. |
| 2009/0118699 A1 | 5/2009 | Utley et al. |
| 2009/0125062 A1 | 5/2009 | Arnin |
| 2009/0171356 A1 | 7/2009 | Klett |
| 2009/0177203 A1 | 7/2009 | Reiley |
| 2009/0182356 A1 | 7/2009 | Coe |
| 2009/0192514 A1 | 7/2009 | Feinberg et al. |
| 2009/0198144 A1 | 8/2009 | Phillips et al. |
| 2009/0204055 A1 | 8/2009 | Lennox et al. |
| 2009/0216113 A1 | 8/2009 | Meier et al. |
| 2009/0216262 A1 | 8/2009 | Burnett et al. |
| 2009/0240173 A1 | 9/2009 | Hsia et al. |
| 2009/0259236 A2 | 10/2009 | Burnett et al. |
| 2009/0270871 A1 | 10/2009 | Liu et al. |
| 2009/0275984 A1 | 11/2009 | Kim et al. |
| 2009/0306717 A1* | 12/2009 | Kercher ............ A61B 17/7011 606/258 |
| 2009/0318919 A1 | 12/2009 | Robinson |
| 2010/0004654 A1 | 1/2010 | Schmitz et al. |
| 2010/0030281 A1 | 2/2010 | Gollogly |
| 2010/0057127 A1 | 3/2010 | McGuire et al. |
| 2010/0081868 A1 | 4/2010 | Moaddeb et al. |
| 2010/0094302 A1 | 4/2010 | Pool et al. |
| 2010/0094303 A1* | 4/2010 | Chang ............... A61B 17/7004 606/90 |
| 2010/0100185 A1 | 4/2010 | Trieu et al. |
| 2010/0106192 A1 | 4/2010 | Barry |
| 2010/0106193 A1 | 4/2010 | Barry |
| 2010/0114103 A1 | 5/2010 | Harrison et al. |
| 2010/0121323 A1* | 5/2010 | Pool ................. A61B 17/7004 606/54 |
| 2010/0121457 A1 | 5/2010 | Clifford et al. |
| 2010/0130941 A1 | 5/2010 | Conlon et al. |
| 2010/0137872 A1 | 6/2010 | Kam et al. |
| 2010/0137911 A1 | 6/2010 | Dant |
| 2010/0137913 A1* | 6/2010 | Khatchadourian ............ A61B 17/7014 606/258 |
| 2010/0145449 A1 | 6/2010 | Makower et al. |
| 2010/0145462 A1 | 6/2010 | Ainsworth et al. |
| 2010/0168751 A1 | 7/2010 | Anderson et al. |
| 2010/0179601 A1 | 7/2010 | Jung et al. |
| 2010/0198261 A1 | 8/2010 | Trieu et al. |
| 2010/0228167 A1 | 9/2010 | Ilovich et al. |
| 2010/0241168 A1 | 9/2010 | Franck et al. |
| 2010/0249782 A1 | 9/2010 | Durham |
| 2010/0249839 A1 | 9/2010 | Alamin et al. |
| 2010/0249847 A1 | 9/2010 | Jung et al. |
| 2010/0256626 A1 | 10/2010 | Muller et al. |
| 2010/0256684 A1 | 10/2010 | Seme et al. |
| 2010/0262160 A1 | 10/2010 | Boyden et al. |
| 2010/0262239 A1 | 10/2010 | Boyden et al. |
| 2010/0262247 A1 | 10/2010 | Arnin |
| 2010/0274290 A1 | 10/2010 | Jung et al. |
| 2010/0280551 A1 | 11/2010 | Pool et al. |
| 2010/0286730 A1 | 11/2010 | Gordon |
| 2010/0286791 A1 | 11/2010 | Goldsmith |
| 2010/0318129 A1 | 12/2010 | Seme et al. |
| 2010/0324600 A1 | 12/2010 | Biyani |
| 2010/0324684 A1 | 12/2010 | Eisermann et al. |
| 2010/0331883 A1 | 12/2010 | Schmitz et al. |
| 2011/0004076 A1 | 1/2011 | Janna et al. |
| 2011/0054536 A1 | 3/2011 | Elsebaie et al. |
| 2011/0057756 A1 | 3/2011 | Marinescu et al. |
| 2011/0060422 A1 | 3/2011 | Makower et al. |
| 2011/0066188 A1 | 3/2011 | Seme et al. |
| 2011/0077738 A1 | 3/2011 | Cuipik et al. |
| 2011/0098748 A1 | 4/2011 | Jangra |
| 2011/0098819 A1 | 4/2011 | Eisermann et al. |
| 2011/0106165 A1 | 5/2011 | Schwab et al. |
| 2011/0118790 A1 | 5/2011 | Reilly |
| 2011/0130702 A1 | 6/2011 | Stergiopulos |
| 2011/0184505 A1 | 7/2011 | Sharkawy et al. |
| 2011/0196371 A1 | 8/2011 | Forsell |
| 2011/0196435 A1 | 8/2011 | Forsell |
| 2011/0202138 A1 | 8/2011 | Shenoy et al. |
| 2011/0238126 A1 | 9/2011 | Soubeiran |
| 2011/0257655 A1 | 10/2011 | Copf, Jr. |
| 2011/0275879 A1 | 11/2011 | Nelson et al. |
| 2011/0284014 A1 | 11/2011 | Cadeddu et al. |
| 2012/0019341 A1 | 1/2012 | Gabay et al. |
| 2012/0019342 A1 | 1/2012 | Gabay et al. |
| 2012/0053633 A1 | 3/2012 | Stauch |
| 2012/0088953 A1 | 4/2012 | King |
| 2012/0089186 A1 | 4/2012 | Carl et al. |
| 2012/0089191 A1 | 4/2012 | Altarac et al. |
| 2012/0109207 A1 | 5/2012 | Trieu |
| 2012/0116522 A1 | 5/2012 | Makower et al. |
| 2012/0116535 A1 | 5/2012 | Ratron et al. |
| 2012/0130426 A1 | 5/2012 | Thompson |
| 2012/0136390 A1 | 5/2012 | Butler et al. |
| 2012/0136449 A1 | 5/2012 | Makower et al. |
| 2012/0150231 A1* | 6/2012 | Alamin ............. A61B 17/1606 606/263 |
| 2012/0172883 A1 | 7/2012 | Sayago |
| 2012/0179273 A1 | 7/2012 | Clifford et al. |
| 2012/0185040 A1 | 7/2012 | Rahdert et al. |
| 2012/0203282 A1 | 8/2012 | Sachs et al. |
| 2012/0221101 A1 | 8/2012 | Moaddeb et al. |
| 2012/0259364 A1 | 10/2012 | Lange |
| 2012/0271353 A1 | 10/2012 | Barry |
| 2012/0277747 A1 | 11/2012 | Keller |
| 2012/0283781 A1 | 11/2012 | Arnin |
| 2012/0296234 A1 | 11/2012 | Wilhelm et al. |
| 2012/0296430 A1 | 11/2012 | Edie et al. |
| 2012/0312307 A1 | 12/2012 | Paraschac et al. |
| 2013/0013066 A1 | 1/2013 | Landry et al. |
| 2013/0018468 A1 | 1/2013 | Moskowitz et al. |
| 2013/0018469 A1 | 1/2013 | Moskowitz et al. |
| 2013/0023991 A1 | 1/2013 | Moskowitz et al. |
| 2013/0079830 A1 | 3/2013 | Garamszegi et al. |
| 2013/0138017 A1 | 5/2013 | Jundt et al. |
| 2013/0138154 A1 | 5/2013 | Reiley |
| 2013/0150889 A1 | 6/2013 | Fening et al. |

(56) References Cited

U.S. PATENT DOCUMENTS

| | | |
|---|---|---|
| 2013/0172940 A1 | 7/2013 | Skaggs |
| 2013/0178903 A1 | 7/2013 | Abdou |
| 2013/0197639 A1 | 8/2013 | Clifford et al. |
| 2013/0204266 A1 | 8/2013 | Heilman |
| 2013/0204376 A1 | 8/2013 | DiSilvestro et al. |
| 2013/0238094 A1 | 9/2013 | Voellmicke et al. |
| 2013/0245692 A1 | 9/2013 | Hayes et al. |
| 2013/0253344 A1 | 9/2013 | Griswold et al. |
| 2013/0253587 A1 | 9/2013 | Carls et al. |
| 2013/0261623 A1 | 10/2013 | Voellmicke et al. |
| 2013/0261672 A1 | 10/2013 | Horvath |
| 2013/0268005 A1 | 10/2013 | Rezach et al. |
| 2013/0268011 A1 | 10/2013 | Rezach et al. |
| 2013/0296863 A1 | 11/2013 | Globerman et al. |
| 2013/0296940 A1 | 11/2013 | Northcutt et al. |
| 2013/0325006 A1 | 12/2013 | Michelinie et al. |
| 2013/0325071 A1 | 12/2013 | Niemiec et al. |
| 2013/0331889 A1 | 12/2013 | Alamin et al. |
| 2013/0345802 A1 | 12/2013 | Cartledge et al. |
| 2014/0005788 A1 | 1/2014 | Haaja et al. |
| 2014/0018913 A1 | 1/2014 | Cartledge et al. |
| 2014/0025172 A1 | 1/2014 | Lucas et al. |
| 2014/0031826 A1 | 1/2014 | Bojarski et al. |
| 2014/0031929 A1 | 1/2014 | Cartledge et al. |
| 2014/0039558 A1 | 2/2014 | Alamin et al. |
| 2014/0051914 A1 | 2/2014 | Fobi et al. |
| 2014/0052134 A1 | 2/2014 | Orisek |
| 2014/0058392 A1 | 2/2014 | Mueckter et al. |
| 2014/0058450 A1 | 2/2014 | Arlet |
| 2014/0066987 A1 | 3/2014 | Hestad et al. |
| 2014/0067075 A1 | 3/2014 | Makower et al. |
| 2014/0080203 A1 | 3/2014 | Wan et al. |
| 2014/0088715 A1 | 3/2014 | Ciupik |
| 2014/0107704 A1 | 4/2014 | Serhan et al. |
| 2014/0114311 A1 | 4/2014 | Pool et al. |
| 2014/0128920 A1 | 5/2014 | Kantelhardt |
| 2014/0135838 A1 | 5/2014 | Alamin et al. |
| 2014/0142631 A1 | 5/2014 | Hunziker |
| 2014/0142698 A1 | 5/2014 | Landry et al. |
| 2014/0163664 A1 | 6/2014 | Goldsmith |
| 2014/0172097 A1 | 6/2014 | Clifford et al. |
| 2014/0194932 A1 | 7/2014 | Bruneau et al. |
| 2014/0222138 A1 | 8/2014 | Machold et al. |
| 2014/0236234 A1 | 8/2014 | Kroll et al. |
| 2014/0296918 A1 | 10/2014 | Fening et al. |
| 2014/0303538 A1 | 10/2014 | Baym et al. |
| 2014/0303539 A1 | 10/2014 | Baym et al. |
| 2014/0303540 A1 | 10/2014 | Baym et al. |
| 2014/0324047 A1 | 10/2014 | Zahrly et al. |
| 2014/0336756 A1 | 11/2014 | Lee et al. |
| 2014/0358150 A1 | 12/2014 | Kaufman et al. |
| 2015/0013687 A1 | 1/2015 | Paraschac et al. |
| 2015/0057490 A1 | 2/2015 | Forsell |
| 2015/0073565 A1 | 3/2015 | Nelson et al. |
| 2015/0105782 A1 | 4/2015 | D'Lima et al. |
| 2015/0105824 A1 | 4/2015 | Moskowitz et al. |
| 2015/0132174 A1 | 5/2015 | Marinescu et al. |
| 2015/0134007 A1 | 5/2015 | Alamin et al. |
| 2015/0142110 A1 | 5/2015 | Myers et al. |
| 2015/0150561 A1 | 6/2015 | Burnett et al. |
| 2015/0272600 A1 | 10/2015 | Mehta et al. |
| 2015/0313649 A1 | 11/2015 | Alamin et al. |

FOREIGN PATENT DOCUMENTS

| | | |
|---|---|---|
| DE | 1541262 | 6/1969 |
| DE | 8515687 | 12/1985 |
| DE | 68515687.6 | 12/1985 |
| DE | 19626230 | 1/1998 |
| DE | 19751733 | 12/1998 |
| DE | 19745654 | 4/1999 |
| DE | 102005045070 | 4/2007 |
| DE | 102007053362 | 5/2009 |
| EP | 0663184 | 7/1995 |
| EP | 1547549 | 6/2005 |
| EP | 1745765 | 1/2007 |
| EP | 1905388 | 4/2008 |
| FR | 2802406 | 6/2001 |
| FR | 2823663 | 10/2002 |
| FR | 2827756 | 1/2003 |
| FR | 2892617 | 5/2007 |
| FR | 2900563 | 11/2007 |
| FR | 2901991 | 12/2007 |
| FR | 2916622 | 12/2008 |
| FR | 2961386 | 12/2011 |
| GB | 1174814 | 12/1969 |
| HU | 223454 | 4/2002 |
| JP | 05-104022 | 4/1993 |
| JP | 09-056736 | 3/1997 |
| JP | 2001-507608 | 6/2001 |
| JP | 2003-172372 | 6/2003 |
| JP | 2003-530195 | 10/2003 |
| JP | 2007-050339 | 3/2007 |
| WO | WO8604498 | 8/1986 |
| WO | WO8707134 | 12/1987 |
| WO | WO8906940 | 8/1989 |
| WO | WO9601597 | 1/1996 |
| WO | WO9808454 | 3/1998 |
| WO | WO9830163 | 7/1998 |
| WO | WO/1998/044858 | 10/1998 |
| WO | WO1998044858 | 10/1998 |
| WO | WO9850309 | 11/1998 |
| WO | WO9903348 | 1/1999 |
| WO | WO9923744 | 5/1999 |
| WO | WO9951160 | 10/1999 |
| WO | WO1999051160 | 10/1999 |
| WO | WO9963907 | 12/1999 |
| WO | WO0000108 | 1/2000 |
| WO | WO0072768 | 12/2000 |
| WO | WO0105463 | 1/2001 |
| WO | WO0112108 | 2/2001 |
| WO | WO0124742 | 4/2001 |
| WO | WO2001024697 | 4/2001 |
| WO | WO0141671 | 6/2001 |
| WO | WO0145485 | 6/2001 |
| WO | WO0145487 | 6/2001 |
| WO | WO0145597 | 6/2001 |
| WO | WO0158390 | 8/2001 |
| WO | WO0167973 | 9/2001 |
| WO | WO0178614 | 10/2001 |
| WO | WO0236975 | 5/2002 |
| WO | WO03059215 | 7/2003 |
| WO | WO2004014245 | 2/2004 |
| WO | WO2004019796 | 3/2004 |
| WO | WO2004021870 | 3/2004 |
| WO | WO2004043280 | 5/2004 |
| WO | WO2005023090 | 3/2005 |
| WO | WO2005072195 | 8/2005 |
| WO | WO2005072664 | 8/2005 |
| WO | WO2005105001 | 11/2005 |
| WO | WO2006019520 | 2/2006 |
| WO | WO2006019521 | 2/2006 |
| WO | WO2006089085 | 8/2006 |
| WO | WO2006090380 | 8/2006 |
| WO | WO2006103071 | 10/2006 |
| WO | WO2006103074 | 10/2006 |
| WO | WO2006105084 | 10/2006 |
| WO | WO2007013059 | 2/2007 |
| WO | WO2007015239 | 2/2007 |
| WO | WO2007025191 | 3/2007 |
| WO | WO/2007/048012 | 4/2007 |
| WO | WO2007048012 | 4/2007 |
| WO | WO2007081304 | 7/2007 |
| WO | WO2007118179 | 10/2007 |
| WO | WO2007140180 | 12/2007 |
| WO | WO2007149555 | 12/2007 |
| WO | WO20071144489 | 12/2007 |
| WO | WO2008003952 | 1/2008 |
| WO | WO2008013623 | 1/2008 |
| WO | WO2008015679 | 2/2008 |
| WO | WO2008040880 | 4/2008 |
| WO | WO2008140756 | 11/2008 |
| WO | WO2010017649 | 2/2010 |
| WO | WO2010050891 | 5/2010 |

(56) References Cited

FOREIGN PATENT DOCUMENTS

| WO | WO2010056650 | 5/2010 |
|---|---|---|
| WO | WO2011018778 | 2/2011 |
| WO | WO2011116158 | 9/2011 |
| WO | WO/2013/066946 | 5/2013 |
| WO | WO2013119528 | 8/2013 |
| WO | WO2013181329 | 12/2013 |
| WO | WO2014040013 | 3/2014 |
| WO | WO2011041398 | 4/2015 |

OTHER PUBLICATIONS

Kasliwal, M., Smith, J., Kanter, A., Chen, C-J., Mummaneni, P., Hart, R., Shaffrey, C. "Management of High-Grade Spondylolisthesis," Neurosrugery Clinics of North America, 2013, vol. 24, pp. 275-291, W.B. Saunders, Philadelphia, United States.
Abe, Jun, Kensei Nagata, Mamoru Ariyoshi, and Akio Inoue. "Experimental external fixation combined with percutaneous discectomy in the management of scoliosis." Spine 24, No. 7 (1999): 646-653.
Amer, A. R. A. L., and Ashraf A. Khanfour. "Evaluation of treatment of late-onset tibia vara using gradual angulationtranslation high tibial osteotomy." Acta orthopaedica Belgica 76, No. 3 (2010): 360.
Angrisani, L., F. Favretti, F. Furbetta, S. Gennai, G. Segato, V. Borrelli, A. Sergio, T. Lafullarde, G. Vander Velpen, and M Lorenzo. "Lap-Band ((R)) Rapid Port (TM) System: Preliminary results in 21 patients." In Obesity Surgery, vol. 15, No. 7,pp. 936-936.
Baumgart, Rainer, Stefan Hinterwimmer, Michael Krammer, Oliver Muensterer, and Wolf Mutschler. "The bioexpandable prosthesis: a new perspective after resection of malignant bone tumors in children." Journal of pediatric hematology/oncology 27, No. 8 (2005): 452-455.
Baumgart, R., P. Thaller, S. Hinterwimmer, M. Krammer, T. Hierl, and W. Mutschler. "A fully implantable, programmable distraction nail (Fitbone)—new perspectives for corrective and reconstructive limb surgery." In Practice of Intramedullary Locked Nails, pp. 189-198. Springer Berlin Heidelberg, 2006.
Bodó, László, László Hangody, Balázs Borsitzky, György Béres, Gabriella Arató, Péter Nagy, and Gábor K. Ráthonyi. "Development of a tension-adjustable implant for anterior cruciate ligament reconstruction." Eklem Hast Cerrahisi 19, No. 1 (2008): 27-32.
Boudjemline, Younes, Emmanuelle Pineau, Caroline Bonnet, Alix Mollet, Sylvia Abadir, Damien Bonnet, Daniel Sidi, and Gabriella Agnoletti. "Off-label use of an adjustable gastric banding system for pulmonary artery banding." The Journal of thoracic and cardiovascular surgery 131, No. 5 (2006): 1130-1135.
Brochure—VEPTR II Technique Guide 4/08.
Brochure—VEPTR Patient Guide dated Feb. 2005.
Brown, S. "Single Port Surgery and the Dundee Endocone." SAGES Annual Scientific Sessions, Poster Abstracts (2007): 323-324.
Buchowski, Jacob M., Rishi Bhatnagar, David L. Skaggs, and Paul D. Sponseller. "Temporary internal distraction as an aid to correction of severe scoliosis." The Journal of Bone & Joint Surgery 88, No. 9 (2006): 2035-2041.
Burghardt, R. D., J. E. Herzenberg, S. C. Specht, and D. Paley. "Mechanical failure of the Intramedullary Skeletal Kinetic Distractor in limb lengthening." Journal of Bone & Joint Surgery, British vol. 93, No. 5 (2011): 639-643.
Burke, John Gerard. "Design of a minimally invasive non fusion device for the surgical management of scoliosis in the skeletally immature." Studies in health technology and informatics 123 (2005): 378-384.
Carter, D. R., and W. E. Caler. "A cumulative damage model for bone fracture." Journal of Orthopaedic Research 3, No. 1 (1985): 84-90.
Chapman, Andrew E., George Kiroff, Philip Game, Bruce Foster, Paul O'Brien, John Ham, and Guy J. Maddern. "Laparoscopic adjustable gastric banding in the treatment of obesity: a systematic literature review." Surgery 135, No. 3 (2004): 326-351.
Cole, J. Dean, Daniel Justin, Tagus Kasparis, Derk DeVlught, and Carl Knobloch. "The intramedullary skeletal distractor (ISKD): first clinical results of a new intramedullary nail for lengthening of the femur and tibia." Injury 32 (2001):129-139.
Cole, J., D. Paley, and M. Dahl. "Operative Technique. ISKD. Intramedullary Skeletal Kinetic Distractor. Tibial Surgical Technique." IS-0508 (A)-OPT-US © Orthofix Inc 28 (2005).
Dailey, Hannah L., Charles J. Daly, John G. Galbraith, Michael Cronin, and James A. Harty. "A novel intramedullary nail for micromotion stimulation of tibial fractures." Clinical Biomechanics 27, No. 2 (2012): 182-188.
Daniels, A. U., Patrick Gemperline, Allen R. Grahn, and Harold K. Dunn. "A new method for continuous intraoperative measurement of Harrington rod loading patterns." Annals of biomedical engineering 12, No. 3 (1984): 233-246.
De Giorgi, G., G. Stella, S. Becchetti, G. Martucci, and D. Miscioscia. "Cotrel-Dubousset instrumentation for the treatment of severe scoliosis." European Spine Journal 8, No. 1 (1999): 8-15.
Dorsey, W. O., Bruce S. Miller, Jared P. Tadje, and Cari R. Bryant. "The stability of three commercially available implants used in medial opening wedge high tibial osteotomy." The journal of knee surgery 19, No. 2 (2006): 95-98.
Edeland, H. G., G. Eriksson, and E. Dahlberg. "Instrumentation for distraction by limited surgery in scoliosis treatment." Journal of biomedical engineering 3, No. 2 (1981): 143-146.
Ember, T., and H. Noordeen. "Distraction forces required during growth rod lengthening." Journal of Bone & Joint Surgery, British vol. 88, No. SUPP II (2006): 229-229.
Fabry, Hans, Robrecht Van Hee, Leo Hendrickx, and Eric Totté. "A technique for prevention of port adjustable silicone gastric banding." Obesity surgery 12, No. 2 (2002): 285-288.
Fried, M., W. Lechner, and K. Kormanova. "In vivo measurements of different gastric band pressures towards the gastric wall at the stoma region." In Obesity Surgery, vol. 14, No. 7, pp. 914-914. 3100 Bayview Ave, Unit 4, Toronto, Ontario M2N 5L3, Canada: F D-Communications Inc, 2004.
Gao, Xiaochong, Derek Gordon, Dongping Zhang, Richard Browne, Cynthia Helms, Joseph Gillum, Samuel Weber et al. "CHD7 gene polymorphisms are associated with susceptibility to idiopathic scoliosis." The American Journal of Human Genetics 80, No. 5 (2007): 957-965.
Gebhart, M., M. Neel, A. Soubeiran, and J. Dubousset. "Early clinical experience with a custom made growing endoprosthesis in children with malignant bone tumors of the lower extremity actioned by an external permanent magnet: the Phenix M system." In International Society of Limb Salvage 14th International Symposium on Limb Salvage.2007.
Gillespie, R., and J. Obrien. "Harrington instrumentation without fusion." In Journal of Bone and Joint Surgerybritish Volume, vol. 63, No. 3, pp. 461-461. 22 Buckingham Street, London, England WC2N 6ET: British Editorial Soc Bone Joint Surgery, 1981.
Goodship, Allen E., James L. Cunningham, and John Kenwright. "Strain rate and timing of stimulation in mechanical modulation of fracture healing." Clinical orthopaedics and related research 355 (1998): S105-S115.
Grass, P. Jose, A. Valentin Soto, and H. Paula Araya. "Intermittent distracting rod for correction of high neurologic risk congenital scoliosis." Spine 22, No. 16 (1997): 1922-1927.
Gray's Anatomy, http://education.yahoo.com/reference/gray/subjects/subject/128, published Jul. 1, 2007.
Grimer, R., S. Carter, R. Tillman, A. Abudu, and L. Jeys. "Non-Invasive Extendable Endoprostheses for Children—Expensive But Worth It!." Journal of Bone & Joint Surgery, British vol. 93, No. SUPP I (2011): 5-5.
Grünert, R. D. "[The development of a totally implantable electronic sphincter]." Langenbecks Archiv fur Chirurgie 325 (1968): 1170-1174.
Guichet, Jean-Marc, Barbara Deromedis, Leo T. Donnan, Giovanni Peretti, Pierre Lascombes, and Flavio Bado. "Gradual femoral lengthening with the Albizzia intramedullary nail." The Journal of Bone & Joint Surgery 85, No. 5 (2003): 838-848.
Gupta, A., J. Meswania, R. Pollock, S. R. Cannon, T. W. R. Briggs, S. Taylor, and G. Blunn. "Non-invasive distal femoral expandable

(56) References Cited

OTHER PUBLICATIONS endoprosthesis for limb-salvage surgery in paediatric tumours." Journal of Bone & Joint Surgery, British vol. 88, No. 5 (2006): 649-654.
Hankemeier S, Gösling T, Pape HC, et al. Limb lengthening with the Intramedullary Skeletal Kinetic Distractor (ISKD) Oper Orthop Traumatol. 2005;17:79-101.
Harrington PR (1962) Treatment of scoliosis. Correction and internal fixation by spine instrumentation. J Bone Joint Surg Am 44-A:591-610.
Hazem Elsebaie, M. D. "Single Growing Rods." Changing the Foundations: Does it affect the Results., J Child Orthop. (2007) 1:258.
Hennig, Alex C.; Incavo, Stephen J.; Beynnon, Bruce D.; Abate, Joseph A.; Urse, John S.; Kelly, Stephen / The safety and efficacy of a new adjustable plate used for proximal tibial opening wedge osteotomy in the treatment of unicompartmental knee osteoarthrosis. In: The journal of knee surgery, vol. 20, No. 1, Jan. 1, 2007, p. 6-14.
Hofmeister, M., C. Hierholzer, and V. Bühren. "Callus Distraction with the Albizzia Nail." In Practice of Intramedullary Locked Nails, pp. 211-215. Springer Berlin Heidelberg, 2006.
Horbach, T., D. Herzog, and I. Knerr. "First experiences with the routine use of the Rapid Port (TM) system with the Lap-Band (R)." In Obesity Surgery, vol. 16, No. 4, pp. 418-418. 3100 Bayview Ave, Unit 4, Toronto, Ontario M2N 5L3, Canada: F D-Communications Inc, 2006.
Hyodo, Akira, Helmuth Kotschi, Helen Kambic, and George Muschler. "Bone transport using intramedullary fixation and a single flexible traction cable." Clinical orthopaedics and related research 325 (1996): 256-268.
Ahlbom, A., U. Bergqvist, J. H. Bernhardt, J. P. Cesarini, M. Grandolfo, M. Hietanen, A. F. Mckinlay et al. "Guidelines for limiting exposure to time-varying electric, magnetic, and electromagnetic fields (up to 300 GHz). International Commission on Non-Ionizing Radiation Protection." Health Phys 74, No. 4 (1998): 494-522.
International Commission on Non-Ionizing Radiation Protection. "Guidelines on limits of exposure to static magnetic fields." Health Physics 96, No. 4 (2009): 504-514.
INVIS®/Lamello Catalog, 2006, Article No. 68906A001 GB.
Kasliwal, Manish K., Justin S. Smith, Adam Kanter, Ching-Jen Chen, Praveen V. Mummaneni, Robert A. Hart, and Christopher I. Shaffrey. "Management of high-grade spondylolisthesis." Neurosurgery Clinics of North America 24, No. 2 (2013): 275-291.
Kenawey, Mohamed, Christian Krettek, Emmanouil Liodakis, Ulrich Wiebking, and Stefan Hankemeier. "Leg lengthening using intramedullay skeletal kinetic distractor: results of 57 consecutive applications." Injury 42, No. 2 (2011): 150-155.
Kent, Matthew E., Arvind Arora, P. Julian Owen, and Vikas Khanduja. "Assessment and correction of femoral malrotation following intramedullary nailing of the femur." Acta Orthop Belg 76, No. 5 (2010): 580-4.
Klemme, William R., Francis Denis, Robert B. Winter, John W. Lonstein, and Steven E. Koop. "Spinal instrumentation without fusion for progressive scoliosis in young children." Journal of Pediatric Orthopaedics 17, No. 6 (1997): 734-742.
Korenkov, M., S. Sauerland, N. Yücel, L. Köhler, P. Goh, J. Schierholz, and H. Troidl. "Port function after laparoscopic adjustable gastric banding for morbid obesity." Surgical Endoscopy and Other Interventional Techniques 17, No. 7 (2003): 1068-1071.
Krieg, Andreas H., Bernhard M. Speth, and Bruce K. Foster. "Leg lengthening with a motorized nail in adolescents." Clinical orthopaedics and related research 466, No. 1 (2008): 189-197.
Kucukkaya, Metin, Raffi Armagan, and Unal Kuzgun. "The new intramedullary cable bone transport technique." Journal of orthopaedic trauma 23, No. 7 (2009): 531-536.
Lechner, W. L., W. Kirchmayr, and G. Schwab. "In vivo band manometry: a new method in band adjustment." In Obesity Surgery, vol. 15, No. 7, pp. 935-935. 3100 Bayview Ave, Unit 4, Toronto, Ontario M2N 5L3, Canada: F Dcommunicationsinc, 2005.

Lechner, W., M. Gadenstatter, R. Ciovica, W. Kirchmayer, and G. Schwab. "Intra-band manometry for band adjustments: The basics." In Obesity Surgery, vol. 16, No. 4, pp. 417-418. 3100 Bayview Ave, Unit 4, Toronto, Ontario M2N 5L3, Canada: F D-Communications Inc, 2006.
Li, G., S. Berven, N. A. Athanasou, and A. H. R. W. Simpson. "Bone transport over an intramedullary nail: A case report with histologic examination of the regenerated segment." Injury 30, No. 8 (1999): 525-534.
Lonner, Baron S. "Emerging minimally invasive technologies for the management of scoliosis." Orthopedic Clinics of North America 38, No. 3 (2007): 431-440.
Teli, Marco MD. "Measurement of Forces Generated During Distraction of Growing Rods, J." Marco Teli. Journal of Child Orthop 1 (2007): 257-258.
Matthews, Michael Wayne, Harry Conrad Eggleston, Steven D. Pekarek, and Greg Eugene Hilmas. "Magnetically adjustable intraocular lens." Journal of Cataract & Refractive Surgery 29, No. 11 (2003): 2211-2216.
Micromotion "Micro Drive Engineering•General catalogue" pp. 14•24; Jun. 2009.
Mineiro, Jorge, and Stuart L. Weinstein. "Subcutaneous rodding for progressive spinal curvatures: early results." Journal of Pediatric Orthopaedics 22, No. 3 (2002): 290-295.
Moe, John H., Khalil Kharrat, Robert B. Winter, and John L. Cummine. "Harrington instrumentation without fusion plus external orthotic support for the treatment of difficult curvature problems in young children." Clinical orthopaedics and related research 185 (1984): 35-45.
Montague, R. G., C. M. Bingham, and K. Atallah. "Magnetic gear dynamics for servo control." In MELECON 2010-2010 15th IEEE Mediterranean Electrotechnical Conference, pp. 1192-1197. IEEE, 2010.
Montague, Ryan, Chris Bingham, and Kais Atallah. "Servo control of magnetic gears." Mechatronics, IEEE/ASME Transactions on 17, No. 2 (2012): 269-278.
Nachemson, Alf, and Gösta Elfström. "Intravital wireless telemetry of axial forces in Harrington distraction rods in patients with idiopathic scoliosis." The Journal of Bone & Joint Surgery 53, No. 3 (1971): 445-465.
Nachlas, I. William, and Jesse N. Borden. "The cure of experimental scoliosis by directed growth control." The Journal of Bone & Joint Surgery 33, No. 1 (1951): 24-34.
Newton, P. "Fusionless Scoliosis Correction by Anterolateral Tethering . . . Can it Work?." In 39th Annual Scoliosis Research Society Meeting. 2004.
Observations by a third party under Article 115 EPC issued by the European Patent Office dated Feb. 15, 2010 in European Patent Application No. 08805612.2, Applicant: Soubeiran, Arnaud (7 pages).
Oh, Chang-Wug, Hae-Ryong Song, Jae-Young Roh, Jong-Keon Oh, Woo-Kie Min, Hee-Soo Kyung, Joon-Woo Kim, Poong-Taek Kim, and Joo-Chul Ihn. "Bone transport over an intramedullary nail for reconstruction of long bone defects in tibia." Archives of orthopaedic and trauma surgery 128, No. 8 (2008): 801-808.
Ozcivici, Engin, Yen Kim Luu, Ben Adler, Yi-Xian Qin, Janet Rubin, Stefan Judex, and Clinton T. Rubin. "Mechanical signals as anabolic agents in bone." Nature Reviews Rheumatology 6, No. 1 (2010): 50-59.
Patient Guide, VEPTR Vertical Expandable Prosthetic Titanium Rib, Synthes Spine (2005) (23pages).
Piorkowski, James R., Scott J. Ellner, Arun A. Mavanur, and Carlos A. Barba. "Preventing port site inversion in laparoscopic adjustable gastric banding." Surgery for Obesity and Related Diseases 3, No. 2 (2007): 159-161.
Prontes, Isabel, http://wwwehow.com/about_4795793_longest-bone-body.html, published Jun. 12, 2012.
Rathjen, Karl, Megan Wood, Anna McClung, and Zachary Vest. "Clinical and radiographic results after implant removal in idiopathic scoliosis." Spine 32, No. 20 (2007): 2184-2188.
Ren, Christine J., and George A. Fielding. "Laparoscopic adjustable gastric banding: surgical technique." Journal of Laparoendoscopic & Advanced Surgical Techniques 13, No. 4 (2003): 257-263.

(56) References Cited

OTHER PUBLICATIONS

Reyes-Sánchez, Alejandro, Luis Miguel Rosales, and Víctor Miramontes. "External fixation for dynamic correction of severe scoliosis." The Spine Journal 5, No. 4 (2005): 418-426.

Rinsky, Lawrence A., James G. Gamble, and Eugene E. Bleck. "Segmental Instrumentation Without Fusion in Children With Progressive Scoliosis." Journal of Pediatric Orthopedics 5, No. 6 (1985): 687-690.

Rode, V., F. Gay, A. J. Baraza, and J. Dargent. "A simple way to adjust bands under radiologic control." In Obesity Surgery, vol. 16, No. 4, pp. 418-418. 3100 Bayview Ave, Unit 4, Toronto, Ontario M2N 5L3, Canada: F DCommunications Inc, 2006.

Schmerling, M. A., M. A. Wilkov, A. E. Sanders, and J. E. Woosley. "Using the shape recovery of nitinol in the Harrington rod treatment of scoliosis." Journal of biomedical materials research 10, No. 6 (1976): 879-892.

Scott, D. J., S. J. Tang, R. Fernandez, R. Bergs, and J. A. Cadeddu. "Transgastric, transcolonic, and transvaginal cholecystectomy using magnetically anchored instruments." In SAGES Meeting, p. P511. 2007.

Sharke, Paul. "The machinery of life." Mechanical Engineering 126, No. 2 (2004): 30.

Shiha, Anis, Mohamed Alam El-Deen, Abdel Rahman Khalifa, and Mohamed Kenawey. "Ilizarov gradual correction of genu varum deformity in adults." Acta Orthop Belg 75 (2009): 784-91.

Simpson, A. H. W. R., H. Shalaby, and G. Keenan. "Femoral lengthening with the intramedullary skeletal kinetic distractor." Journal of Bone & Joint Surgery, British vol. 91, No. 7 (2009): 955-961.

Smith, John T. "The use of growth-sparing instrumentation in pediatric spinal deformity." Orthopedic Clinics of North America 38, No. 4 (2007): 547-552.

Soubeiran, A., M. Gebhart, L. Miladi, J. Griffet, M. Neel, and J. Dubousset. "The Phenix M System. A Mechanical Fully Implanted Lengthening Device Externally Controllable Through the Skin with a Palm Size Permanent Magnet; Applications to Pediatric Orthopaedics." In 6th European Research Conference in Pediatric Orthopaedics. 2006.

Stokes, Oliver M., Elizabeth J. O'Donovan, Dino Samartzis, Cora H. Bow, Keith DK Luk, and Kenneth MC Cheung. Reducing radiation exposure in early-onset scoliosis surgery patients: novel use of ultrasonography to measure lengthening in magnet.

Sun, Zongyang, Katherine L. Rafferty, Mark A. Egbert, and Susan W. Herring. "Masticatory mechanics of a mandibular distraction osteogenesis site: interfragmentary micromovement." Bone 41, No. 2 (2007): 188-196.

Takaso, Masashi, Hideshige Moriya, Hiroshi Kitahara, Shohei Minami, Kazuhisa Takahashi, Keijiro Isobe, Masatsune Yamagata, Yoshinori Otsuka, Yoshinori Nakata, and Masatoshi Inoue. "New remote-controlled growing-rod spinal instrumentation possibly applicable for scoliosis in young children." Journal of orthopaedic science 3, No. 6 (1998): 336-340.

Tello, Carlos A. "Harrington instrumentation without arthrodesis and consecutive distraction program for young children with severe spinal deformities. Experience and technical details." The Orthopedic clinics of North America 25, No. 2 (1994): 333-351.

Thaller, Peter Helmut, Julian Fürmetz, Florian Wolf, Thorsten Eilers, and Wolf Mutschler. "Limb lengthening with fully implantable magnetically actuated mechanical nails (PHENIX®)—Preliminary results." Injury 45 (2014): S60-S65.

Thompson, George H., Lawrence G. Lenke, Behrooz A. Akbarnia, Richard E. McCarthy, and Robert M. Campbell. "Early onset scoliosis: future directions." The Journal of Bone & Joint Surgery 89, No. suppl 1 (2007): 163-166.

Thonse, Raghuram, John E. Herzenberg, Shawn C. Standard, and Dror Paley. "Limb lengthening with a fully implantable, telescopic, intramedullary nail." Operative Techniques in Orthopedics 15, No. 4 (2005): 355-362.

Trias, A., P. Bourassa, and M. Massoud. "Dynamic loads experienced in correction of idiopathic scoliosis using two types of Harrington rods." Spine 4, No. 3 (1978): 228-235.

VEPTR II. Vertical Expandable Prosthetic Titanium Rib II, Technique Guide, Systhes Spine (2008) (40 pages).

Verkerke, G. J., Koops H. Schraffordt, R. P. Veth, H. J. Grootenboer, L. J. De Boer, J. Oldhoff, and A. Postma. "Development and test of an extendable endoprosthesis for bone reconstruction in the leg." The International journal of artificial organs 17, No. 3 (1994): 155-162.

Verkerke, G. J., H. Schraffordt Koops, R. P. H. Veth, J. Oldhoff, H. K. L. Nielsen, H. H. Van den Kroonenberg, H. J. Grootenboer, and F. M. Van Krieken. "Design of a lengthening element for a modular femur endoprosthetic system." Proceedings of the Institution of Mechanical Engineers, Part H: Journal of Engineering in Medicine 203, No. 2 (1989): 97-102.

Verkerke, G. J., H. Schraffordt Koops, R. P. H. Veth, H. H. van den Kroonenberg, H. J. Grootenboer, H. K. L. Nielsen, J. Oldhoff, and A. Postma. "An extendable modular endoprosthetic system for bone tumour management in the leg." Journal of biomedical engineering 12, No. 2 (1990): 91-96.

Weiner, Rudolph A., Michael Korenkov, Esther Matzig, Sylvia Weiner, and Woiteck K. Karcz. "Initial clinical experience with telemetrically adjustable gastric banding." Surgical technology international 15 (2005): 63-69.

Wenger, H. L. "Spine Jack Operation in the Correction of Scoliotic Deformity: A Direct Intrathoracic Attack to Straighten the Laterally Bent Spine: Preliminary Report." Archives of Surgery 83, No. 6 (1961): 901-910.

White III, Augustus A., and Manohar M. Panjabi. "The clinical biomechanics of scoliosis." Clinical orthopaedics and related research 118 (1976): 100-112.

Yonnet, Jean-Paul. "Passive magnetic bearings with permanent magnets." Magnetics, IEEE Transactions on 14, No. 5 (1978): 803-805.

Yonnet, Jean-Paul. "A new type of permanent magnet coupling." Magnetics, IEEE Transactions on 17, No. 6 (1981): 2991-2993.

Zheng, Pan, Yousef Haik, Mohammad Kilani, and Ching-Jen Chen. "Force and torque characteristics for magnetically driven blood pump." Journal of Magnetism and Magnetic Materials 241, No. 2 (2002): 292-302.

\* cited by examiner

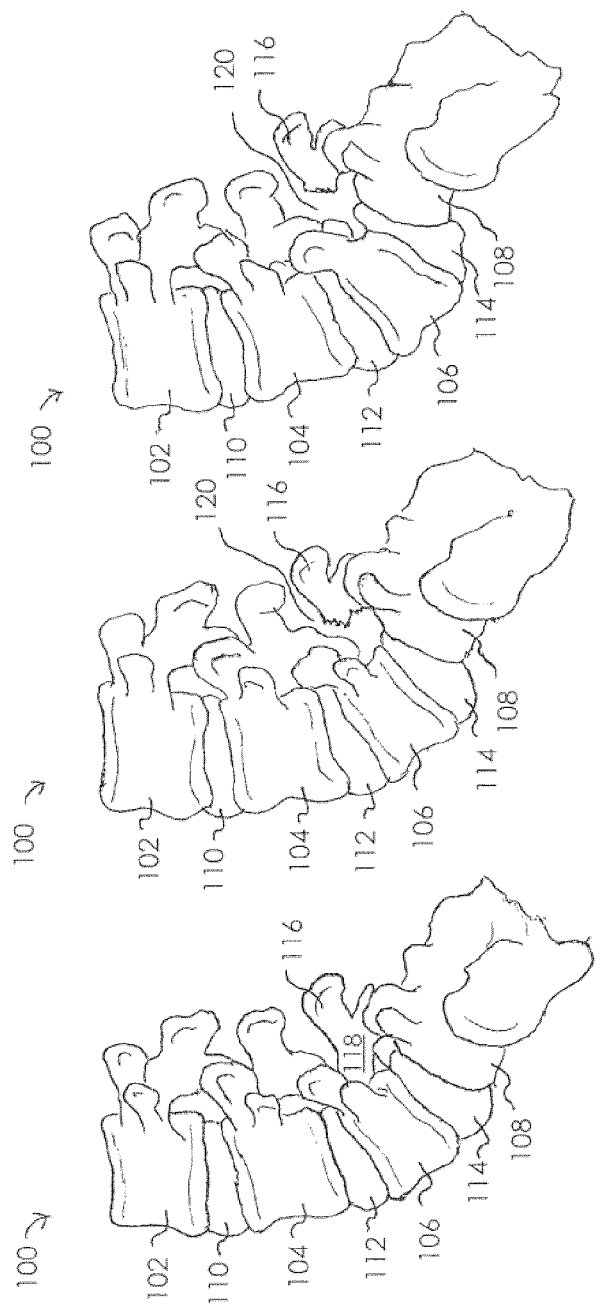

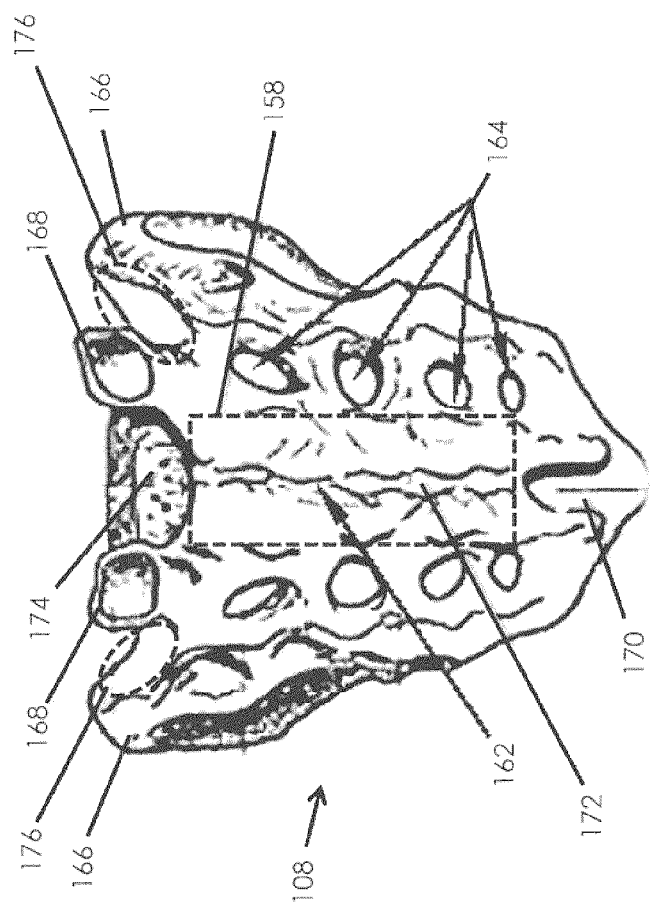

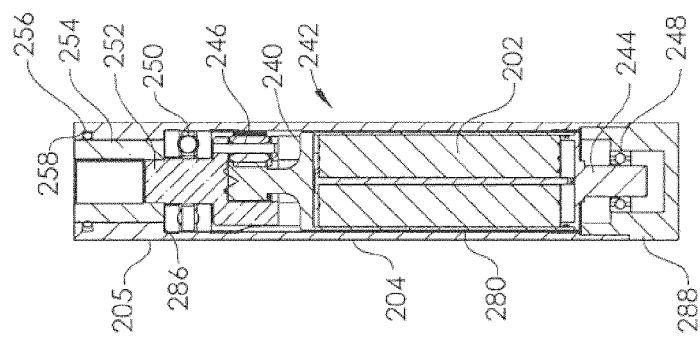
FIG. 11
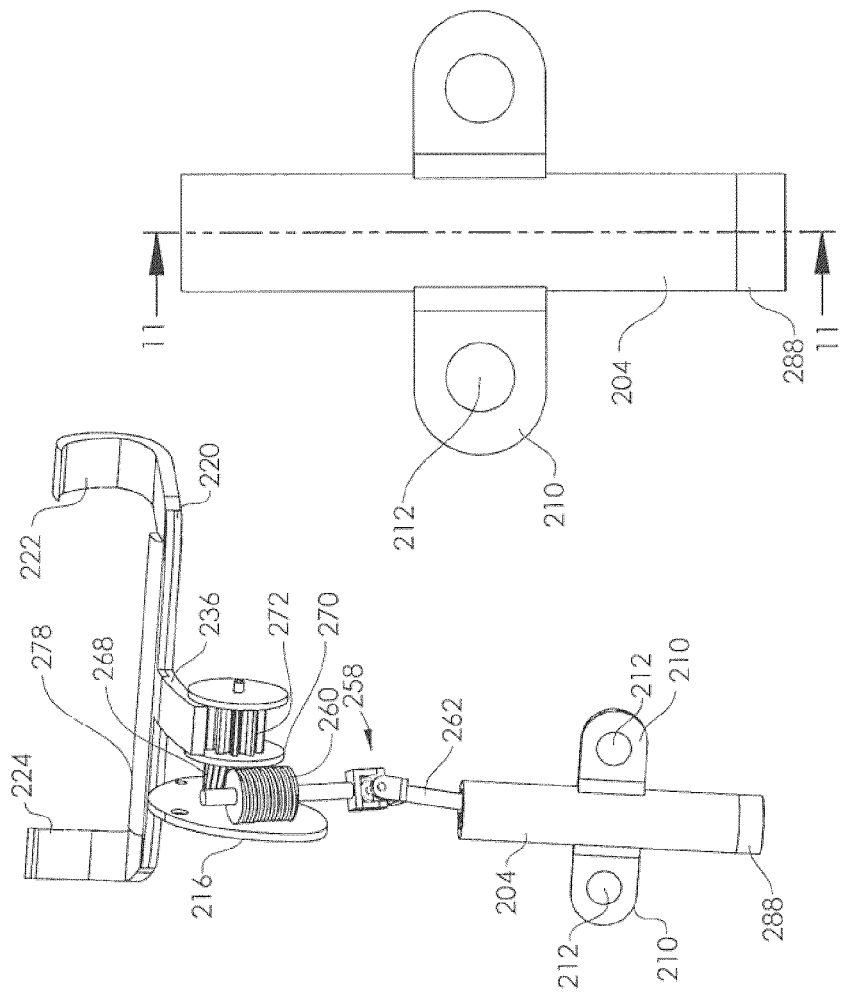
FIG. 10
FIG. 9

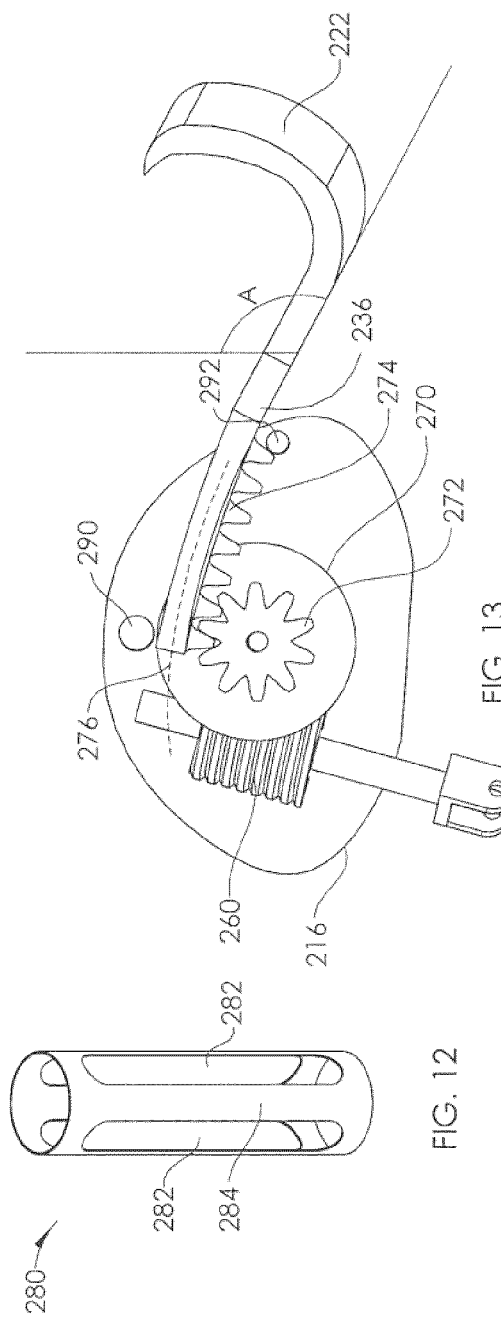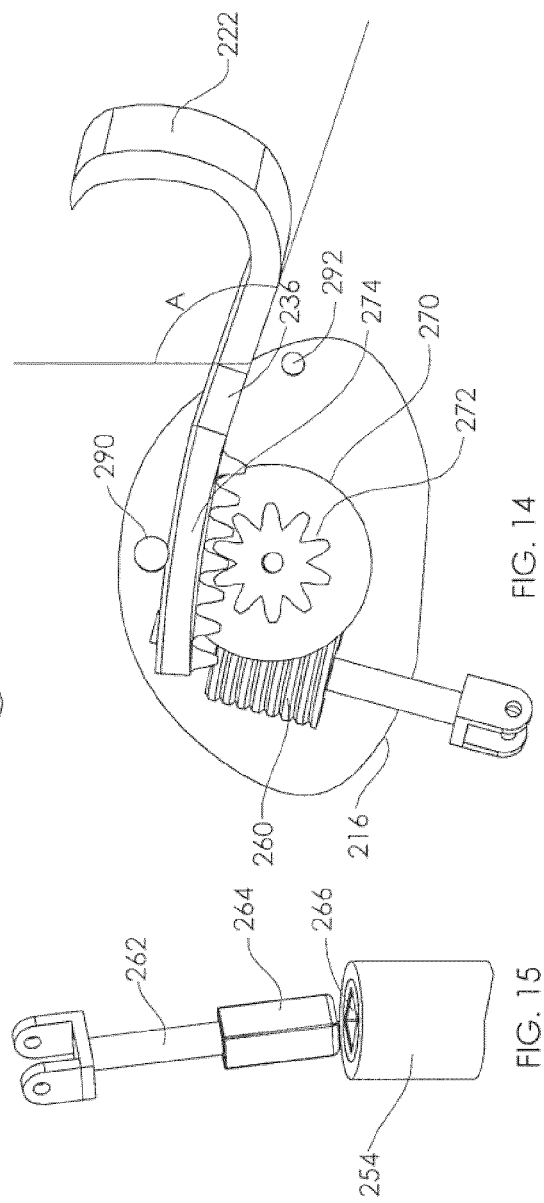

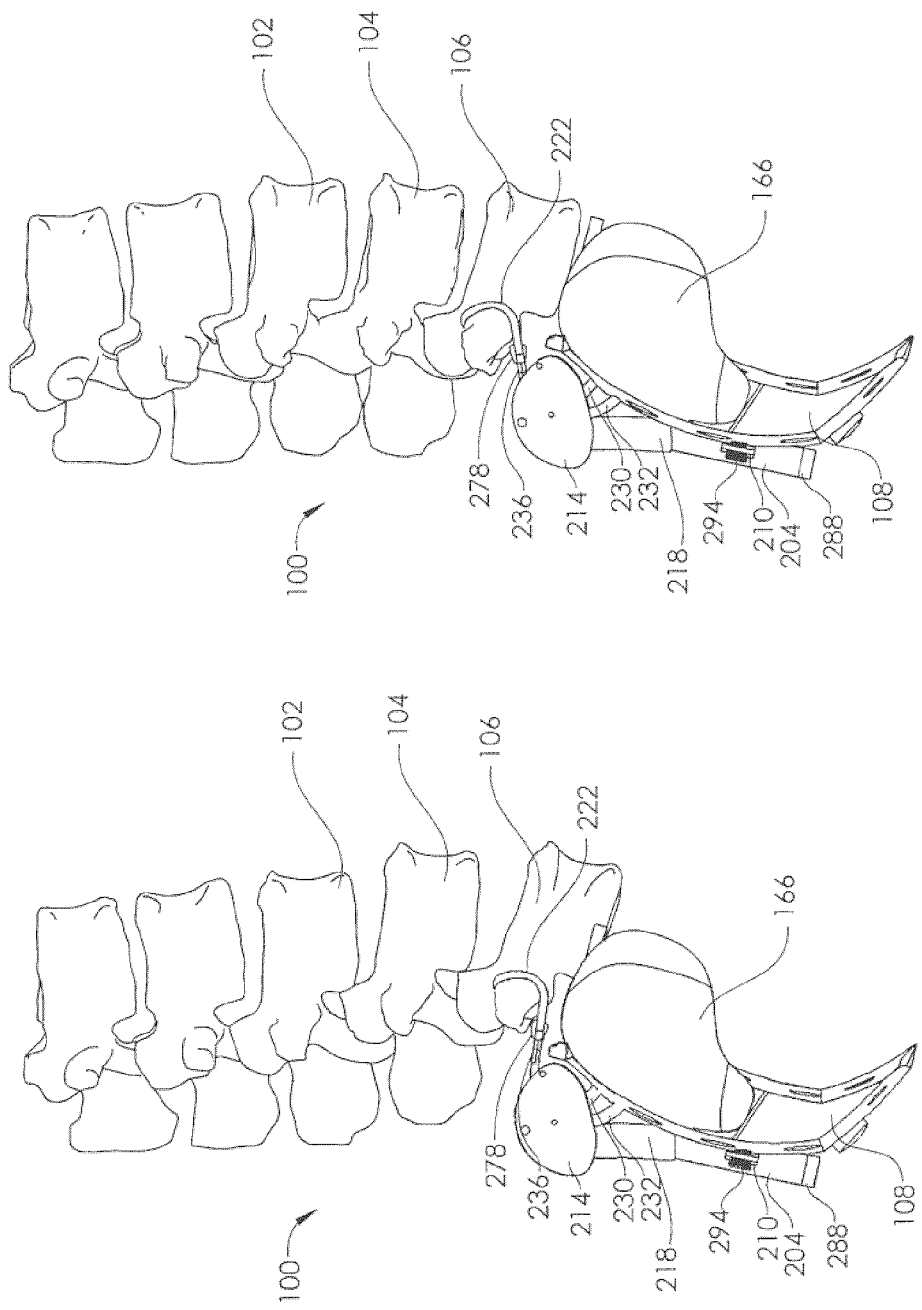

ADJUSTABLE SPINAL IMPLANT

INCORPORATION BY REFERENCE TO ANY PRIORITY APPLICATIONS

Any and all applications for which a foreign or domestic priority claims is identified in the Application Data Sheet as filed with the present application are hereby incorporated by reference under 37 CFR 1.57.

BACKGROUND

Field of the Invention

The field of the invention generally relates to medical devices for treating deformities of the spine, including spondylolisthesis.

Description of the Related Art

Spondylolisthesis is a condition of the spine in which one vertebra is displaced in relation to another vertebra.

SUMMARY

In one embodiment, a non-invasively adjustable spinal system for treatment of a subject having spondylolisthesis is provided. The system includes a first implantable actuator having at least one anchoring structure, the anchoring structure configured to facilitate securement of the first implantable actuator to a portion of the sacrum of the subject. The non-invasively adjustable spinal system further includes an adjustment element, configured to be coupled to the first implantable actuator, the adjustment element having an engagement structure configured to engage at least one transverse process of a lumbar vertebra of the subject. The non-invasively adjustable spinal system further includes a driving element, wherein remote activation of the driving element causes movement of the adjustment element in relation to the first implantable actuator.

In another embodiment, a method for treating spondylolisthesis in a subject having a spine containing a sacrum and at least a portion of an L5 vertebra is provided. The method includes providing a non-invasively adjustable spinal implant having a first implantable actuator having at least one anchoring structure, the anchoring structure configured to facilitate securement of the first implantable actuator to a portion of the sacrum of the subject, an adjustment element, configured to be coupled to the first implantable actuator, the adjustment element comprising an engagement structure configured to engage at least one transverse process of a lumbar vertebra of the subject, and a driving element, wherein remote activation of the driving element causes movement of the adjustment element in relation to the first implantable actuator. The method for treating spondylolisthesis further includes making a first incision in the skin of the subject, placing the non-invasively adjustable spinal implant through the first incision, securing at least a portion of the non-invasively adjustable implant to a portion of the sacrum of the subject, coupling the engagement structure to at least one transverse process of the L5 vertebra, and causing or allowing the first incision to close.

BRIEF DESCRIPTION OF THE DRAWINGS

FIG. 1A illustrates three lower lumbar vertebra and sacrum of a spine.

FIG. 1B illustrates a lower spine exhibiting the condition of spondylolysis in the L5 vertebra.

FIG. 1C illustrates a lower spine exhibiting the condition of spondylolisthesis between the L5 vertebra and sacrum.

FIG. 6 illustrates a dorsal portion of a sacrum of a subject.

FIG. 9 illustrates the adjustable spinal implant of FIG. 7 with certain external components removed.

FIG. 10 illustrates a magnetic actuator.

FIG. 11 is a cross-sectional view of the magnetic actuator of FIG. 10 taken along the line 11-11.

FIG. 12 illustrates a maintenance tube of the magnetic actuator of FIG. 10.

FIG. 13 illustrates certain components of an adjustable spinal implant in a first adjustment condition.

FIG. 14 illustrates certain components of an adjustable spinal implant in a second adjustment condition.

FIG. 15 illustrates a connectable interface between a magnetic actuator and a gear housing.

FIG. 17 illustrates a side view of an adjustable implant implanted on a spine of a subject having spondylolisthesis.

FIG. 18 illustrates a spine of a subject having spondylolisthesis after reduction treatment by an adjustable spinal implant.

DETAILED DESCRIPTION

Figure 2A:
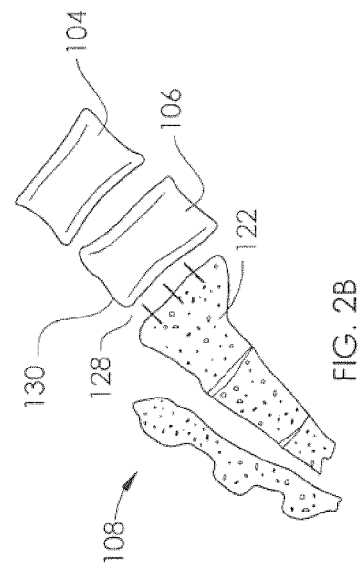
FIG. 2A is a partial sectional view of a normal portion of a lower spine.
Figure 2B:
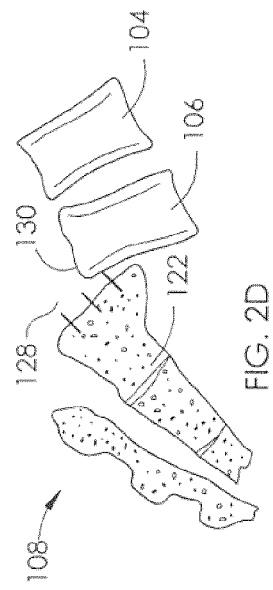
FIG. 2B is a partial sectional view of a lower spine exhibiting Grade I spondylolisthesis.

In FIG. 1 the lower spine 100 includes vertebrae L3 102, L4 104, L5 106, and the sacrum 108. Intervertebral discs 110, 112, 114 are also shown. In certain subjects, chronic or acute upward stresses on the sacrum 108 can create upward forces on the contacting spinous process 116 (in this case the spinous process 116 of L5 106) and downward forces on the L5 106 vertebral body itself. This may culminate in a defect 120, for example, a stress fracture, of the pars interarticularis 118. The defect 120, as seen in FIG. 1B, is known as spondylolysis, and may occur in as much as 6% of the population. Some risk factors which may lead to spondylolysis, often occurring in combination, include hereditary anatomic factors (thin spinal bone) and strenuous sports and activities, such as tennis, volleyball, soccer, and gymnastics. The hyperextension and heavy landings common to many strenuous sports have each been hypothesized as causes for spondylolysis. The L5 106 vertebra is the location of the defect 120 in the majority of spondylolysis cases, but it may also occur in other lumbar vertebrae, and even in non-lumbar vertebrae. Spondylolysis may on its own cause back pain, neck pain, or radiating limb pain, but it is often followed by related disc slippage known as spondylolisthesis, which is illustrated in FIG. 1C. The spondylolisthesis in FIG. 1C is shown between the L5 106 vertebra and the sacrum 108. This is thought to be the most common location for spondylolisthesis to occur, but again, it may occur between other vertebrae.

Figure 2C:
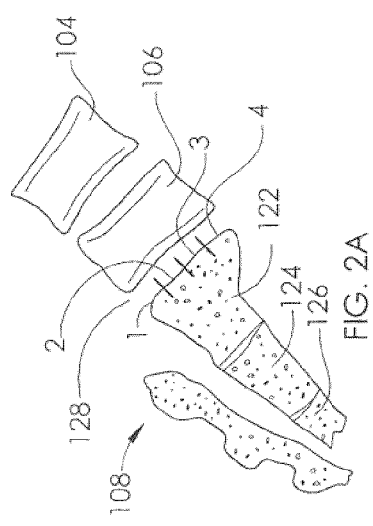
FIG. 2C is a partial sectional view of a lower spine exhibiting Grade II spondylolisthesis.
Figure 2D:
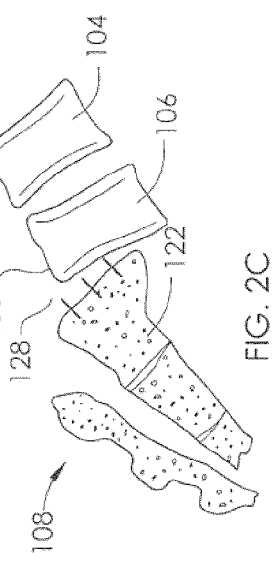
FIG. 2D is a partial sectional view of a lower spine exhibiting Grade III spondylolisthesis.
Figure 2E:
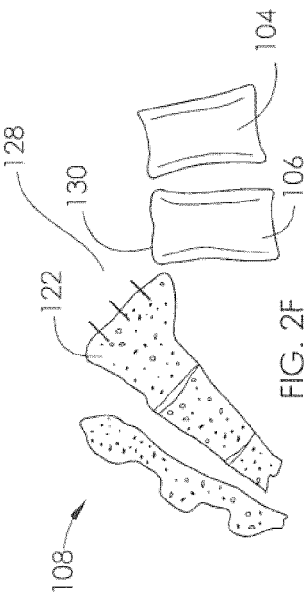
FIG. 2E is a partial sectional view of a lower spine exhibiting Grade IV spondylolisthesis.
Figure 2F:
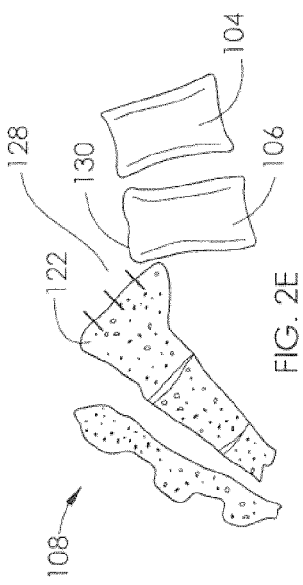
FIG. 2F is a partial sectional view of a lower spine exhibiting Grade V spondylolisthesis.

In many people, the defect 120 is created during adolescence, but it often goes unnoticed at that time. Typical disc degeneration occurring during adulthood may then produce the spondylolisthesis, which can be accompanied by other symptoms. Sometimes, adult degenerative disc disease may even lead to spondylolisthesis without the defect 120 (spondylolysis) occurring. FIG. 2A illustrates the L4 104 and L5 106 of the lumbar vertebrae and S1 122, S2 124, and S3 126 vertebrae of the sacrum 108 of a subject having L5-S1 segment 128 which is normal. FIGS. 2B through 2F show L5-S1 segments 128 having increasing grades of spondylolisthesis. These figures are intended to show the orientation of the L5 106 to the S1 122, and not their overall orientation in relation to anything else, for example, the ground while the subject is standing. A commonly used method of grading spondylolisthesis divides the sacrum 108 into four equal sectors (i.e., 1, 2, 3, and 4), as seen in FIG. 2A. A subject has a grade 1 spondylolisthesis (FIG. 2B) when the edge 130 of the slipped vertebra (in this case L5 106) is within sector 1. In FIG. 2C the spondylolisthesis is grade 2 because the edge 130 of the slipped L5 106 is within sector 2. In FIG. 2D the spondylolisthesis is grade 3 because the edge 130 of the slipped L5 106 is within sector 3. In FIG. 2E the spondylolisthesis is grade 4 because the edge 130 of the slipped L5 106 is within sector 4. In FIG. 2F the edge 130 of the slipped L5 106 has slipped past the four sectors and is therefore considered a grade 5; the condition of grade 5 spondylolisthesis is also known as spondyloptosis. In the higher grades of spondylolisthesis, subjects may either remain asymptomatic, or may present with back pain and/or leg pain. Subjects having higher grade spondylolisthesis may also experience secondary changes to the natural sagittal curve of their spine (sagittal deformity). It may be desirable to treat an adult who has experienced chronic pain symptoms that may be medically attributed to a spondylolisthesis grade of about 4 or higher by implantation of an embodiment of devices as described and illustrated herein. Such treatment may be used to either minimize the risk of progression to a higher spondylolisthesis grade, to lower the spondylolisthesis grade, or both minimize the risk of progression and lower the grade of spondylolisthesis.

Adolescents with higher grade spondylolisthesis may be at a heightened risk for progression in the severity of their condition than adults, and for this reason, surgery is often recommended. While adults with spondylolisthesis may have less risk of progression, they often have back pain or leg pain symptoms that warrant surgery. In order to reduce the risk of progression to a higher grade spondylolisthesis it may be desirable to treat an adolescent having grade 1 spondylolisthesis that is at risk of progressing/worsening by implantation of an embodiment of devices as described and illustrated herein.

Figure 3B:
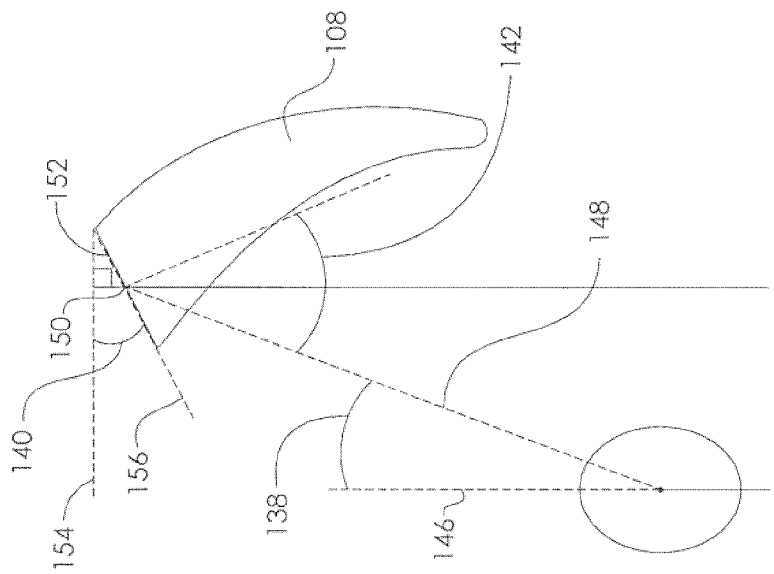
FIG. 3B illustrates an orientation of a sacrum of the spine of a subject.
Figure 3A:
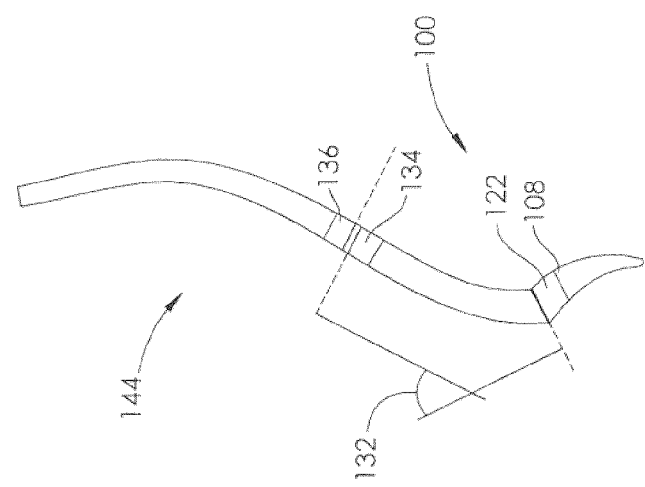
FIG. 3A illustrates a spinal column of a subject.

FIGS. 3A and 3B illustrate several sagittal pelvic parameters which may be calculated from x-rays (taken while the subject is standing) in subjects having L5-S1 spondylolisthesis, or at risk of progression of L5-S1 spondylolisthesis. The purpose of these parameters is to describe the location and orientation of the sacrum 108 in relation to the ground and to the entire spinal column 144 and pelvis. Lumbar lordosis (LL) 132 is defined as the angle measured between the superior (upper) endplate of the L1 vertebra 134 and the superior endplate of the S1 vertebra 122. Thoracic vertebra T12 136 is also shown in FIG. 3A, for reference. Pelvic tilt (PT) 138 is defined as the angle between vertical 146 (a line perpendicular to the ground on which the subject stands) and the line 148 which leads to the middle 150 of the sacral plate 152 at the superior end of the sacrum 108 (chosen midline between the two hip/femur joints). Sacral slope (SS) 140 is defined as the angle between the horizontal 154 and a line 156 drawn along the sacral plate 152 at the superior end of the sacrum 108. Pelvic Incidence (PI) 142 is equal to the sum of the pelvic tilt (PT) 138 and the sacral slope (SS) 140. Some studies have concluded that an increased pelvic incidence (PI) 142 may be a risk factor for the development and progression of spondylolisthesis.

Surgery typically includes of partial or complete reduction (restoration to correct alignment) followed by fusion, or, in many cases, fusion alone without reduction. Fusion without reduction (in situ fusions) can be successful in subjects in whom symptoms have occurred mainly because of motion of the segment. However, in a large number of subjects, some amount of reduction prior to fusion can advantageously decompress the nerve root. Reduction of higher grade spondylolisthesis may be difficult due to both increased rigidity of the deformity and stiffness across the junction between the L5 106 and S1 122. This is especially true in adults who have secondary degenerative changes as the entire deformity is frequently less mobile. In some studies, a significant percentage of subjects experienced further slip progression, even after fusion surgery, a phenomenon that some attribute to incomplete correction of the angular deformity (e.g., bringing the lumbar lordosis (LL) 132 back towards its normal desired value). Fusion without reduction may also be associated with higher rates of non-union than reduction followed by fusion, which many have attributed to the higher stresses on the junction between the L5 106 and S1 122, and also to the decreased surface area for fusion because of the incomplete alignment of the L5 106 and S1 122.

Figure 5:
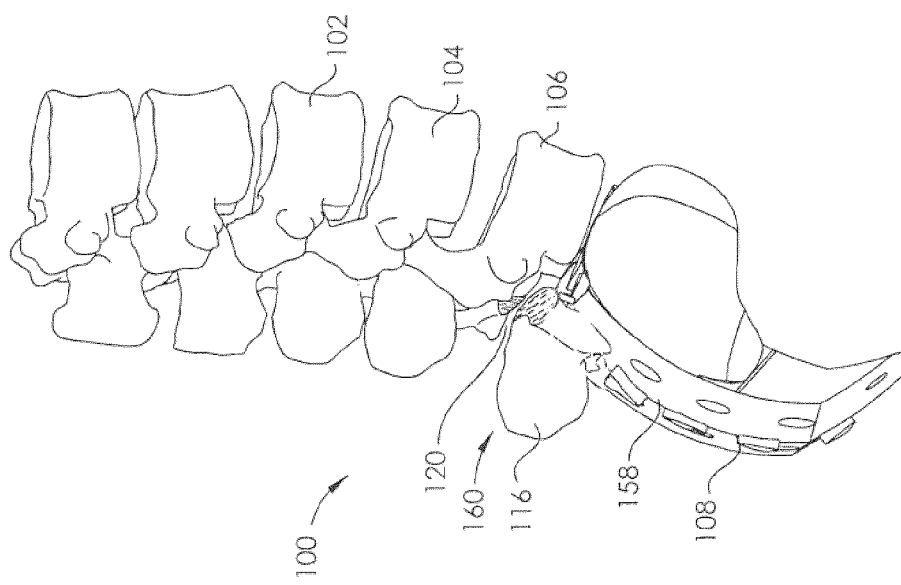
FIG. 5 is a perspective view of a lower spine of a subject having spondylolisthesis.
Figure 4:
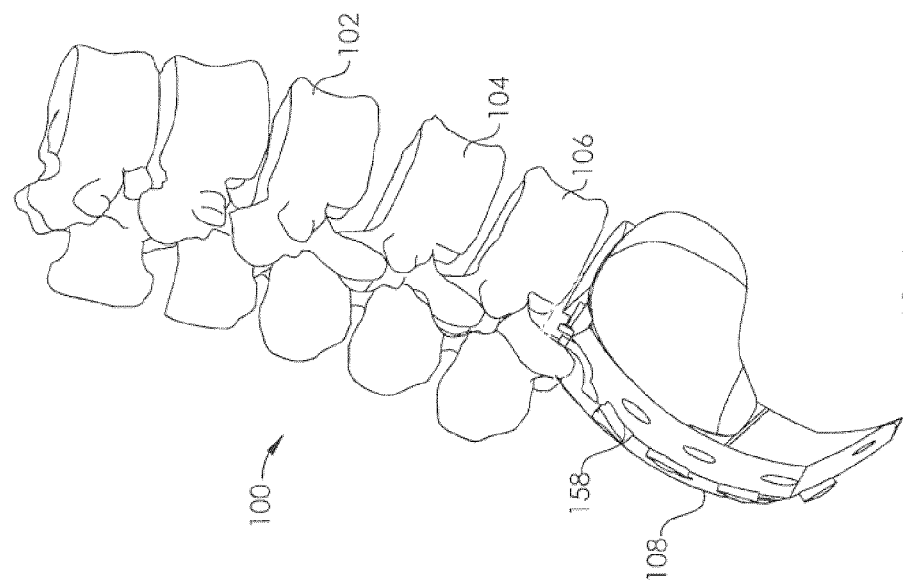
FIG. 4 is a perspective view of a lower spine of a normal subject.

FIGS. 4 and 5 depict the lower spine 100 of a normal subject (FIG. 4) and a subject with spondylolisthesis (FIG. 5). In FIGS. 4 and 5, the lower spine 100 is shown without the surrounding soft tissue in order to better illustrate a treatment plan using an embodiment of devices as described and illustrated herein. An adjustable spinal implant 200 (FIG. 7) according to an embodiment of devices as described and illustrated herein will be coupled at least partially to a medial-dorsal portion 158 of the sacrum 108 following removal of a dorsal portion 160 of the L5 106, for example, a dorsal portion 160 that previously had been severed from the L5 106 during the creation of the defect 120 in spondylolysis. FIG. 6 illustrates the anatomy of a dorsal portion of the sacrum 108, indicating the medial-dorsal portion 158 within a dashed box. Within this medial-dorsal portion 158 is the sacral crest 162 which covers the sacral canal 174 and extends towards the sacral hiatus 170. The sacral crest 162 comprises a plurality of tubercles 172. Several dorsal sacral foramina 164 (also called posterior sacral foramina) are arrayed along the sacrum 108 and provide openings in the sacrum 108 for the transmission of the posterior divisions of the sacral nerves (not shown). Two alas 166 extend laterally and two sacral horns 168 (also called superior auricular processes) reside at the superior portion of the sacrum 108. A medial surface 176 (within the dashed oval marking) at the edge of each ala 166 extends substantially towards each sacral horn 168. The adjustable spinal implant 200 of FIG. 7 may also be configured to at least partially contact a portion of the medial surface 176.

The reason that reduction is sometimes avoided prior to fusion is traditionally because it is often associated with a high rate of neurological deficit. However, neurological deficit can also occur, though at a lower rate, in fusions done without reduction. Because of complications inherent to either excess reduction or insufficient reduction, a partial reduction prior to fusion may elicit the best result. However, it is frequently difficult to predict what will be the most appropriate amount of reduction prior to fusion. Additionally, a gradual reduction, such as several small steps spaced out by days, weeks or even months, may allow for a complete reduction prior to fusion: in some cases, it may even obviate fusion.

Figure 8:
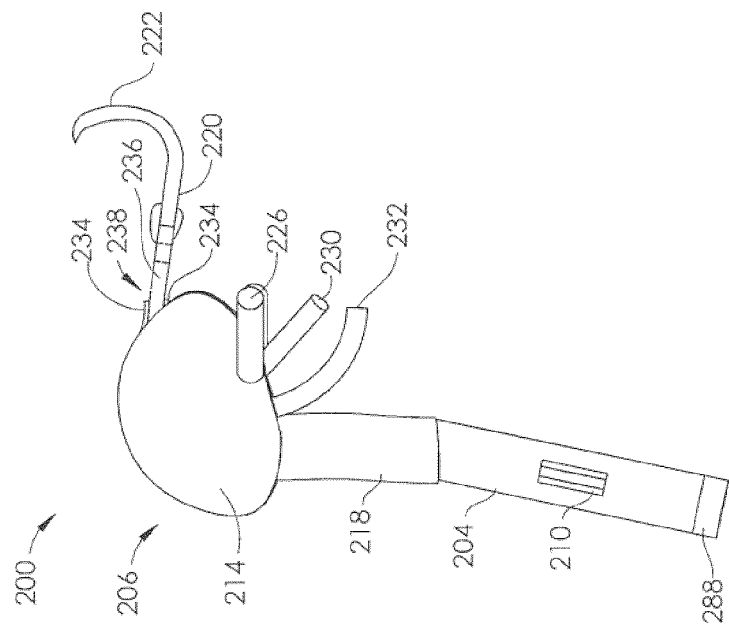
FIG. 8 illustrates a side view of the adjustable spinal implant of FIG. 7.
Figure 7:
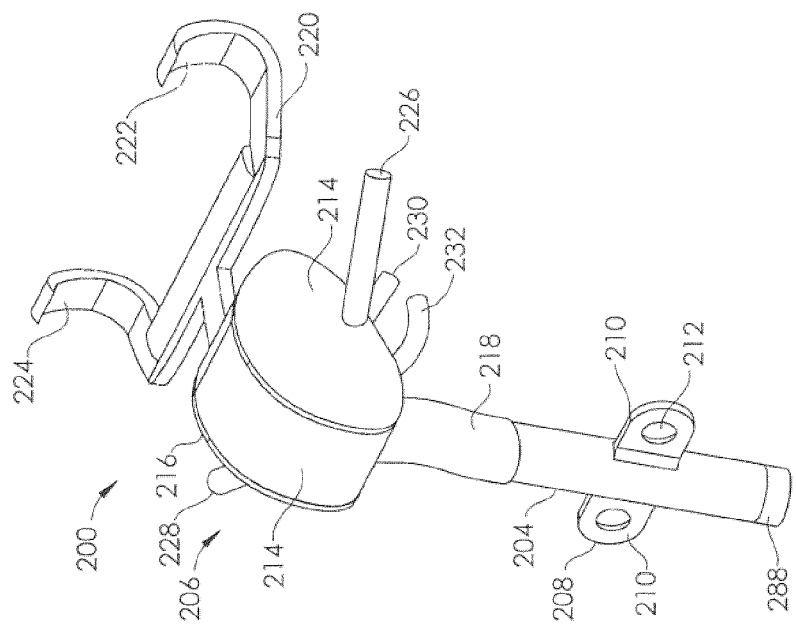
FIG. 7 illustrates an adjustable spinal implant according to an embodiment of the present invention.

FIGS. 7 and 8 illustrate an adjustable spinal implant 200 for implantation and subsequent non-invasive adjustment within a subject having spondylolisthesis. The adjustable spinal implant 200 comprises an implantable actuator 204 which is coupled to an adjustment element 206. Between the implantable actuator 204 and the adjustment element 206 is a flexible tubular member 218, which serves to protect the connecting elements and create a seal or barrier to prohibit body fluids from entering either the implantable actuator 204 or the adjustable element 206. The implantable actuator 204 includes an anchoring structure 208, for example, anchoring tabs 210 having holes 212 for passing bone screws to secure the implantable actuator to the sacrum 108 of a subject. The adjustment element 206 comprises a gear housing 214 which is fully enclosed by a gear housing cover 216. The adjustment element 206 also includes an engagement structure 220 having a right transverse process hook 222 and a left transverse process hook 224. The engagement structure 220 may be monolithic or may be an assembly of more than one part. The engagement structure 220 is adjustable with respect to the gear housing 214. A moveable arm 236 of the engagement structure 220 extends into the gear housing 214. A dynamic seal 234 is provided in an opening 238 of the gear housing 214, which seals around the moveable arm 236. The adjustment element 206 includes several feet 226, 228, 230, 232 which aid in stabilizing the adjustment element 206 with respect to the sacrum 108 by, for example, providing opposing forces to traction created when the engagement structure 220 is adjusted.

FIGS. 9 through 15 show additional internal and external detail of the adjustable spinal implant 200. FIG. 9 shows the adjustable spinal implant 200 with the flexible tubular member 218 and the gear housing 214 removed. A driving element or rotatable magnetic assembly 242 is rotationally mounted within a housing 205 of the implantable actuator 204 and comprises a radially-poled permanent magnet 202 which is held within a magnetic housing 240, for example, with adhesive or epoxy, or by a mechanical fit. The magnetic housing 240 sealably encloses the radially-poled permanent magnet 202 by attachment of a magnetic housing cap 244. The radially-poled permanent magnet may be a cylindrical or partially cylindrical rare earth magnet, for example, Neodymium-Iron-Boron, and may have two poles, four poles, or more. The rotatable magnetic assembly 242 is coupled to a planetary gear set 246, and both the rotatable magnetic assembly 242 and the planetary gear set 246 are held between a radial bearing 248 and a thrust bearing 250. The output shaft 252 of the planetary gear set 246 is joined to a rotational coupler 254, for example, by welding or adhesive bonding. If, for example, the planetary gear set 246 is provided with a 4:1 gear ratio, then four rotations of the rotatable magnetic assembly 242 cause one rotation of the rotational coupler 254. Additionally, given a 4:1 gear ratio, torque generated by the rotational coupler 254 can be up to four times greater than the torque applied to the radially-poled permanent magnet 202 (for example, by the application of a rotating magnetic field). An o-ring 256 is held within a circumferential groove 258 in the housing 205, and seals around the diameter of the rotational coupler 254.

A universal joint 258 (FIG. 9) provides a flexible connection between the rotational coupler 254 and a worm 260. FIG. 15 illustrates the releasable connection between the implantable actuator 204 and the adjustable element 206. A first member 262 of the universal joint 258 having a square end 264 can be snapped into and snapped out of a square cavity 266. The universal joint 258 and the surrounding flexible tubular member 218 allow for the securement of both the implantable actuator 204 and the adjustable element 206 in a number of different orientations, to match varying anatomy of the subject, while still allowing operation. The worm 260 engages a worm gear portion 268 of a gear 270 so that rotation of the worm 260 causes rotation of the gear 270. As visible also in FIGS. 13 and 14, the gear may also include a pinion 272 configured to engage with an arcuate rack 274 that extends from the movable arm 236 of the engagement structure 220. As the gear 270 is caused to turn in a first rotational direction by the worm 260 the arcuate rack 274 moves in an arcuate path 276. By providing an engagement structure 220 capable of holding the L5 vertebra 106 without any rotational slippage, the L5 vertebra 106 may not only be translated (reduced) in relation to the sacrum 108, but also, the L5 vertebra 106 may be rotated (or derotated) in relation to the sacrum 108. An example is shown by the decrease of angle A from FIG. 13 to FIG. 14, which happens in conjunction with the displacement of right transverse process hook 222. Such angle change can lower the pelvic incidence (PI) 142 in a subject, and thus potentially lower their risk of progressive spondylolisthesis. Angle change can also directly improve lumbar lordosis (LL) 132. One way of achieving this change in angle of the L5 vertebra 106 is shown in FIG. 9. A cross bar 278 extends between the right transverse process hook 222 the left transverse process hook 224, and is configured to provide a pushing force in the proximity of a dorsal portion of the L5 vertebra 106 while the right transverse process hook 222 the left transverse process hook 224 are providing traction. Because these opposing forces are applied at different heights on the L5 vertebra 106 (one inferior to the other), a rotational moment is applied to the L5 vertebra 106. The gear 270 and the worm 260 are held within both the gear housing 214 and the gear housing cover 216 by standard stops, pins, bosses and the like. Additionally first bar 290 and second bar 292 extend within the gear housing 214 and/or the gear housing cover 216 in order to act as guides for the arcuate rack 274 as it is moved. At least the second bar 292 can act as a stop to prevent overextension of the arcuate rack 274.

The housing 205 of the implantable actuator 204 may also contain a maintenance tube 280 (illustrated in FIG. 12). The maintenance tube 280 is constructed from a structurally rigid material that is also relatively magnetic, for example, 400 series stainless steel. Open elongated holes 282 in the wall of the maintenance tube 280 cause circumferential magnetic discontinuities. The north and south poles of the radially-poled permanent magnet 202 will be attracted to the extending wall ribs 284, but not to the open elongated holes 282. While implanted within a subject, the adjustable spinal implant 200 maintains its configuration (dimension, etc.) due to this attraction. Adjusting the adjustable spinal implant 200 with the use of a sufficient strong externally applied moving magnetic field can overcome this attraction and allow the radially-poled permanent magnet 202 to be turned. The maintenance tube 280 is secured within the housing 205 of the implantable actuator and can provide one end of an axial stop for the thrust bearing 250. Another axial stop for the thrust bearing 250 can be provided by a ledge 286 within the housing 205. In some embodiments, the thrust bearing 250 is not held completely tight, and may have a finite amount of axial play. In other embodiments, the thrust bearing 250 is held with substantially no axial play. An actuator housing cap 288 may be permanently or removably attached to the housing 205 of the implantable actuator 204 to enclose and protect the contents of the housing 205 from body fluids.

Figure 16:
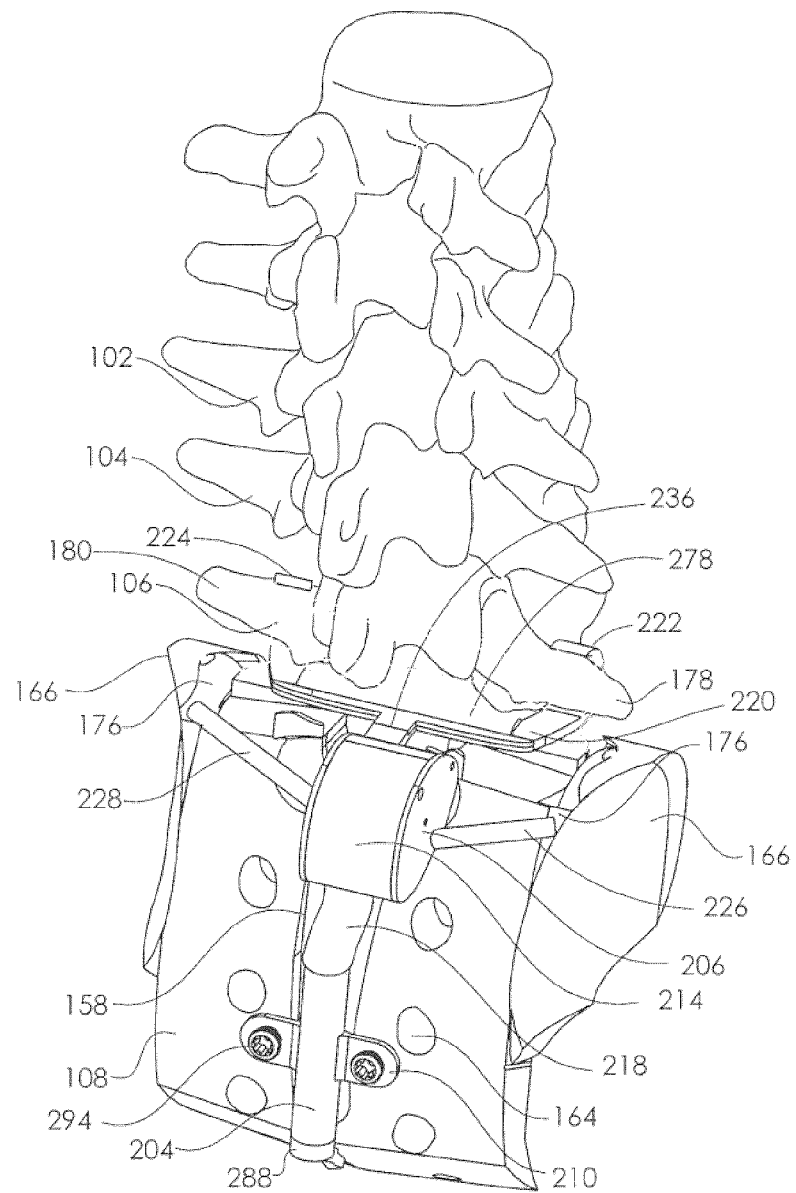
FIG. 16 illustrates the adjustable spinal implant of FIG. 7 implanted on a spine of a subject having spondylolisthesis.

In use, the adjustable spinal implant 200 can be coupled to the L5 vertebra 106 and the sacrum 108 by a surgeon during a surgical implantation procedure. The adjustable spinal implant 200 is shown in FIG. 16, as implanted, on the L5 vertebra 106 and sacrum 108. The right transverse process hook 222 of the engagement structure 220 has been hooked around a right transverse process 178 of the L5 vertebra 106. The left transverse process hook 224 of the engagement structure 220 has been hooked around a left transverse process 180 of the L5 vertebra 106. A foot 226 has been trimmed and/or bent (or otherwise shaped) so that it rests against medial surface 176 of the right ala 166 and a foot 228 has been trimmed and/or bent (or otherwise shaped) so that it rests against medial surface 176 of the left ala 166. The implantable actuator 204 has been secured to the sacrum 108 by placing bone anchors 294 through the holes 212 in the anchoring tabs 210 (shown in FIG. 7). The bone anchors 294 may comprise a screw having a threaded shank and a tapered threaded head. The holes 212 may have matching tapered internal threads to interface with the tapered head of the bone anchors 294. The adjustable element 206 has been coupled to the implantable actuator 204 via the square end 264 and square cavity 266, and the flexible tubular member 218 has been slid into place over the end of the housing 205 of the implantable actuator 204 and over a cylindrical extension (not shown) of the gear housing 214. It can be appreciated from FIG. 17 that legs 230, 232 may also be trimmed and/or bent (or otherwise shaped) to contact medial-dorsal portion 158 of the sacrum 108. Prior to the implantation of the adjustable spinal implant 200, portions of the sacral crest 162 and other bone material within the medial-distal portion 158 may be cut or ground away, or even partially hollowed out. As can be seen in FIGS. 16 and 17, the implantable actuator 204 may reside partially within this hollowed out area.

In FIGS. 16 and 17, the L5 vertebra 106 is in a slipped position approximating grade 3 spondylolisthesis in relation to the sacrum 108. FIG. 17 shows the lower spine 100 after a dorsal portion 160 of the L5 vertebra 106 has been removed through an incision in the skin. Subsequently, the adjustable spinal implant 200 is implanted as described above and the incision is allowed or caused to close, for example, by suturing or using an adhesive sealant, and the overall healing is allowed to progress. In one or more subsequent procedures, a medical care professional or a member of the family of the subject applies a remote moving magnetic field, thereby causing the moveable arm 236 to be retracted into the gear housing 214 via the rack 274 and pinion 272. FIG. 18 shows the lower spine 100 after one or more adjustment procedures. The L5 vertebra 106 has been reduced to a position approximating grade 1 spondylolisthesis. In addition, the angular orientation between the L5 vertebra 106 and the sacrum 108 has been changed. Specifically, the kyphotic condition has been improved, returning more of the natural lordosis. Because the lumbar vertebrae are connected to each other, the reduction of the L5 vertebra 106 may cause the lower spine 100, particularly the adjacent L4 vertebra 104 and L3 vertebra 102, to reform to its preferred conformation. It should be noted that in FIGS. 17 and 18, the foot 226 has purposely not been depicted to better show the positioning of feet 230 and 232.

It may be useful to perform the adjustment of spondylolisthesis using the adjustable spinal implant 200 on a conscious subject who is able to provide at least substantially real-time feedback related to pain and/or balance. Conscious subjects may be able to advantageously move into several different, positions, including those positions that are most likely to cause pain. This is to be contrasted with "wake up tests," sometimes performed during surgery, in which subjects are neither in natural positions, nor do they have their standard senses and reflexes (due to the effects of drugs and anesthesia). Additionally, the amount of linear reduction to treat a patient is generally expected to be in the range of about 5-60 mm, about 7-50, and more specifically about 10-40 mm. Derotation of the L5 vertebra 106 in relation to the sacrum 108 versus the total amount of linear reduction can be controlled by producing a rack having varied radii. For example, a straight (linear) rack may be used if no derotation is desired. It is generally expected that derotation in the range of about 0-75 degrees is appropriate, and in many cases a derotation in the range of about 5-50 degrees. The amount of adjustment may be at least partially determined using feedback received from a conscious subject.

Figure 20:
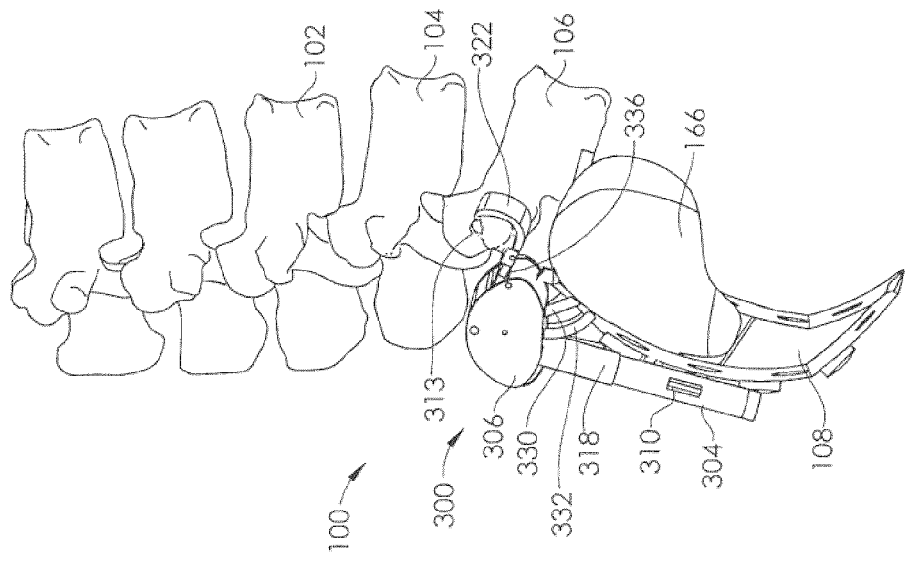
FIG. 20 illustrates a spine of a subject having spondylolisthesis after reduction treatment by adjustable spinal implants.
Figure 19:
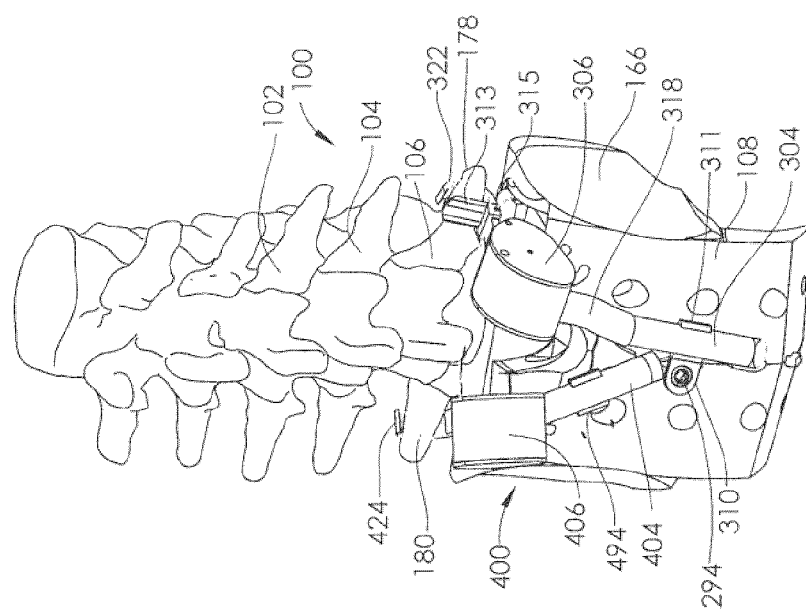
FIG. 19 illustrates a side view of adjustable spinal implants according another embodiment of the present invention implanted on a spine of a subject having spondylolisthesis.

FIGS. 19 and 20 depict a pair of adjustable spinal implants 300, 400 according to another embodiment of the of devices as described and illustrated herein. A first adjustable spinal implant 300 comprises a first implantable actuator 304 coupled to a first adjustable element 306, with a flexible tubular member 318 extending between them. The first implantable actuator 304 may be secured to the sacrum by a bone anchor 294 which passes through an anchoring tab 310. In some embodiments, only one anchoring tab 310 is used, with the other removed, leaving a remnant 311. In other embodiments, two anchoring tabs 310 are used. A right transverse process hook 322 is hooked around the right transverse process 178. A stability element 313 is secured to the right transverse process hook 322 with a set screw 315, in order to clamp onto the right transverse process 178 and substantially eliminate rotational slippage between the right transverse process hook 322 and the right transverse process 178. The surface of the right transverse process 178 may be slightly ground flat in order to better accept the stability element 313 to further inhibit rotation between the two. The right transverse process hook 322 may be directly connected to a movable arm 336 which extends into a rack and pinion mechanism similar to that described in the embodiment depicted in FIGS. 7-18. Feet 330, 332 for contacting and bracing against the sacrum 108, are illustrated in FIG. 20. A second adjustable spinal implant 400 comprises a second implantable actuator 404 coupled to a second adjustable element 406. A clamping bone anchor 494 holds outer diameter of the second implantable actuator 404. A left transverse process hook 424 is hooked around the left transverse process 180. In some embodiments, a stability element 313 may also be used with the left transverse process hook 424 (in the same manner as described with respect to the right transverse process hook 322), though it is not shown in FIG. 19. The first adjustable spinal implant 300 and second adjustable spinal implant 400 have separate internal adjustment mechanisms, including radially-poled permanent magnets. Therefore, the two adjustable spinal implants 300 and 400 may be independently adjustable in relation to one another. This may aid in situations where the L5 vertebra 106 is rotated undesirably along the axis of the subject's torso. For example, the first adjustable spinal implant 300 may be adjusted differentially relative to the second adjustable spinal implant 400 in order to derotate a chosen amount. During implantation, the first adjustable spinal implant 300 and the second adjustable implant 400 may be implanted through the same incision or they may be implanted through different incisions.

Figure 21:
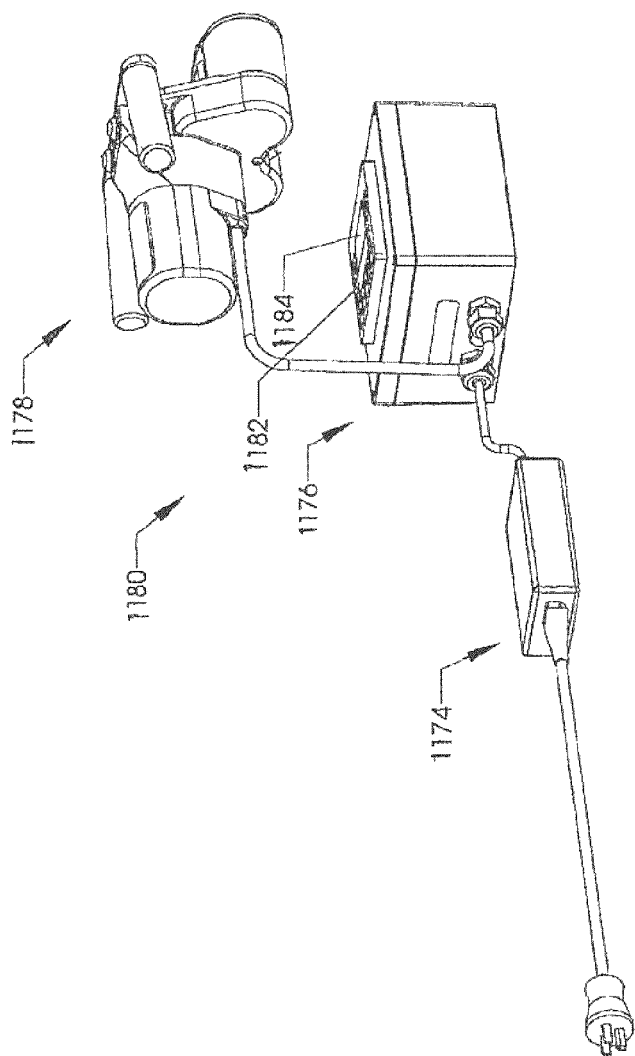
FIG. 21 illustrates a perspective view of an external adjustment device.

FIG. 21 illustrates an external adjustment device 1180 which may be used to non-invasively adjust devices and systems described herein. The external adjustment device 1180 comprises a magnetic handpiece 1178, a control box 1176 and a power supply 1174. The control box 1176 includes a control panel 1182 having one or more controls (buttons, switches or tactile, motion, audio or light sensors) and a display 1184. The display 1184 may be visual, auditory, tactile, the like or some combination of the aforementioned features. The external adjustment device 1180 may contain software which allows programming by a physician, including the ability to lock a patient out from using the external adjustment device 1180, limit the amount of possible adjustment per day, per hour, etc.

Figure 22:
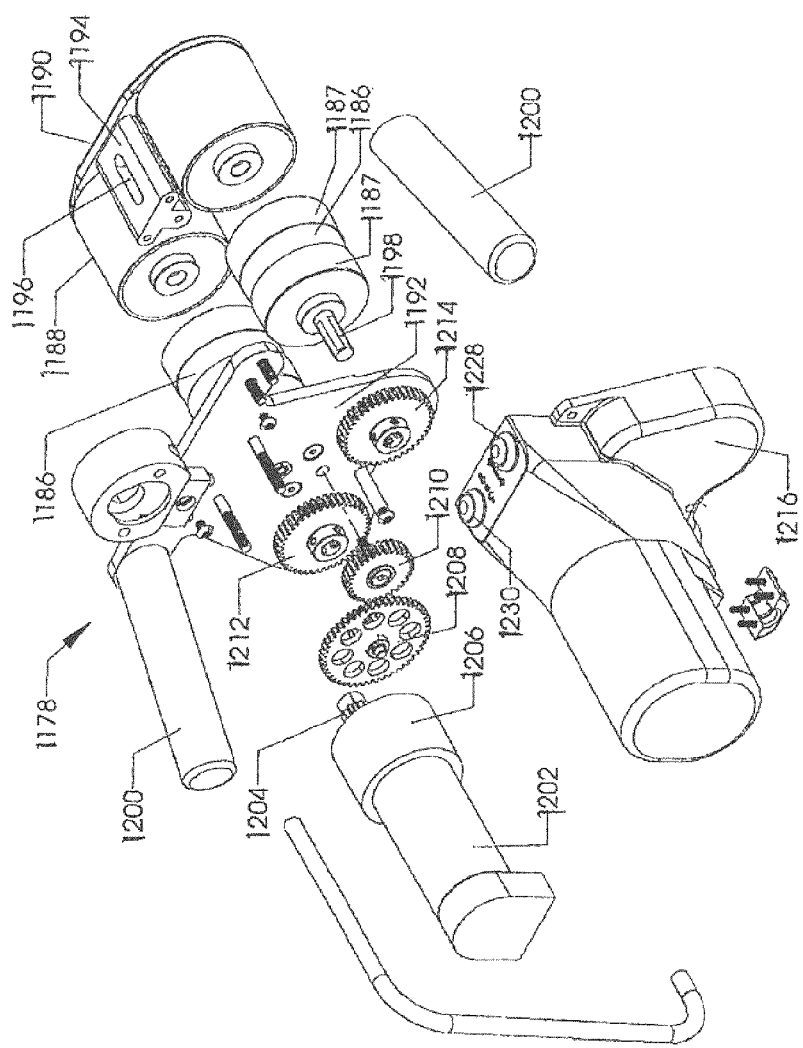
FIG. 22 illustrates an exploded view of a magnetic handpiece of the external adjustment device of FIG. 21.

FIG. 22 shows an exploded view of the magnetic handpiece 1178 of the external adjustment device 1180. There are two magnets 1186 that can have a cylindrical shape. The magnets 1186 may be made from rare earth magnets. The magnets 1186 may be bonded or otherwise secured within magnetic cups 1187. The magnetic cups 1187 can include shafts 1198 attached to a first magnet gear 1212 and second magnet gear 1214. The orientation of the poles of each the two magnets 1186 are substantially fixed with respect to each other through a gearing system including, for example, center gear 1210, which meshes with both first magnet gear 1212 and second magnet gear 1214).

The components of the magnetic handpiece 1178 may be held together between a magnet plate 1190 and a front plate 1192. Most of the components are protected by cover 1216. The magnets 1186 rotate within a static magnet cover 1188, so that the magnetic handpiece 1178 may be rested directly on the patient while not causing motion to the external surfaces of the patient. Prior to distraction of the adjustable spinal implant 200 using the external adjustment device 1180, the operator places the magnetic handpiece 1178 over the patient near the location of the radially-poled permanent magnet 202, for example, on the skin covering the dorsal portion of the sacrum 108. A magnet standoff 1194 interposed between the two magnets 1186 can contain a viewing window 1196, that may aid in placement. For instance, a mark made on the patient's skin at the appropriate location with an indelible marker may be viewed through the viewing window 1196. To use the external adjustment device 1180 to perform a distraction, an operator generally holds the magnetic handpiece 1178 by its handles 1200 and causes motor 1202 to drive in a first direction. The motor 1202 may have a gear box 1206 which can cause the rotational speed of an output gear 1204 to be different from the rotational speed of the motor 1202 (for example, a slower speed). The output gear 1204 can then turn a reduction gear 1208 meshing with center gear 1210, which can cause center gear 1210 to turn at a different rotational speed than the reduction gear 1208. The center gear 1210 can mesh with both the first magnet gear 1212 and the second magnet gear 1214 thereby turning them at the same rate. Depending on the portion of the body where the magnets 1186 of the external adjustment device 1180 are located, it may be desired that the rate of rotation of the magnets be controlled to minimize the resulting induced current density imparted by magnet 1186 and cylindrical magnet 1134 though the tissues and fluids of the body. In some embodiments, a magnet rotational speed of about 60 RPM or less is contemplated. In other embodiments, a magnet rotational speed of about 35 RPM or less may be used. At any time, the distraction may be lessened by causing the magnets to rotate in the opposite direction (e.g., by depressing retract switch 1230). If the patient feels significant pain, or numbness in the area holding the device, the magnitude of distraction may be decreased. The magnets 1186 of the magnetic handpiece can comprise one or more permanent magnets or one or more electromagnets. For example, one or more electromagnets can be configured to provide a rotating magnetic field capable of causing rotation of the radially-poled permanent magnet 202.

Figure 23A:
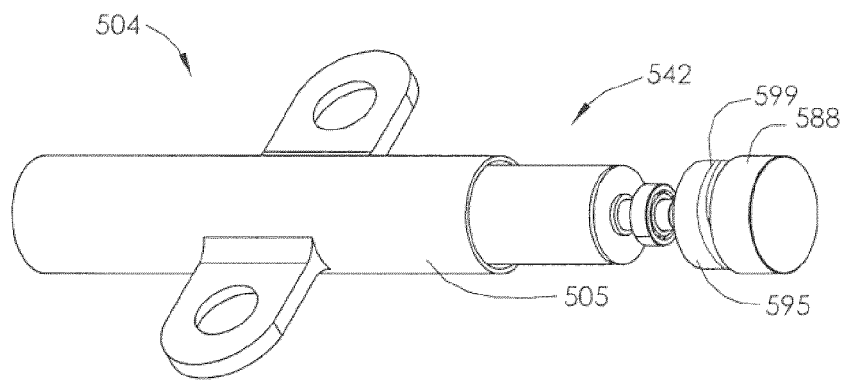
FIG. 23A illustrates a magnetic actuator of an adjustable spinal implant according to an embodiment of the present invention during removal of a magnetic assembly.
Figure 23B:
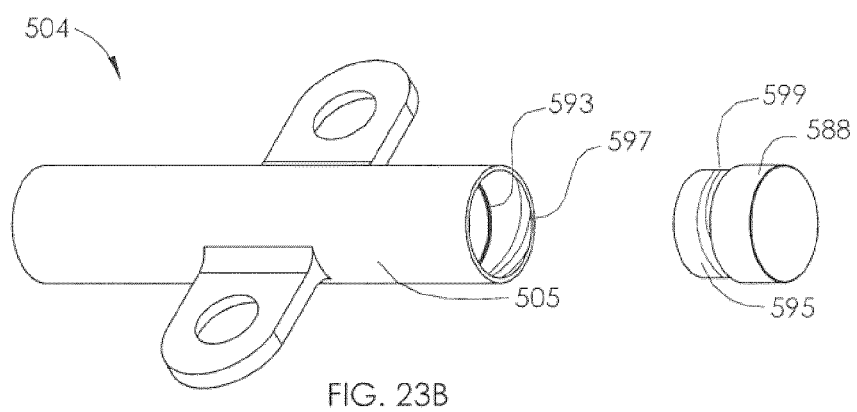
FIG. 23B illustrates a magnetic actuator of an adjustable spinal implant after removal of a magnetic assembly.
Figure 23C:
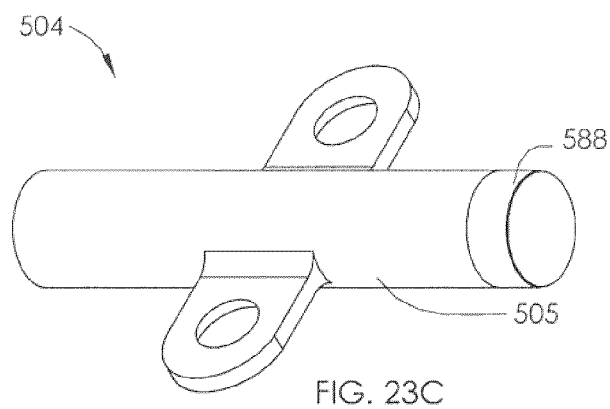
FIG. 23C illustrates a magnetic actuator of an adjustable spinal implant after replacement of an actuator housing cap.

FIGS. 23A through 23C illustrate a magnetic actuator 504 which may be used with any of the embodiments of the of devices as described and illustrated herein, and which allows for temporary or permanent removal of a rotatable magnetic assembly 542. Patients undergoing magnetic resonance imaging (MRI) may benefit from the removal of radially-poled permanent magnet 502 prior to MM in order to avoid a large imaging artifact caused by the radially-poled permanent magnet 502. Additionally, there is a risk that in implanted radially-poled permanent magnet 502 may be demagnetized upon entering an MM scanner. An actuator housing cap 588 has a male thread 599 which engages with a female thread 597 of the housing 505 of the magnetic actuator 504. Alternatively, a snap/unsnap interface may be used. A smooth diameter portion 595 of the actuator housing cap 588 is sealed with an o-ring 593, which is held within a circumferential groove on the inner surface of the housing 505. If, at a time subsequent to the implantation of the magnetic actuator 504, it is desirable to remove the rotatable magnetic assembly 542 while leaving the rest of the implant intact, a small incision may be made in the skin of a subject in proximity to the actuator housing cap 588, and the actuator housing cap 588 may be unscrewed. The rotatable magnetic assembly 542 may then be removed through the incision, as shown in FIG. 23A. FIGS. 23B and 23C show the subsequent steps of replacing the actuator housing cap 588 onto the housing 505 again sealing it against the o-ring 593. The incision may then be closed, and the subject may undergo typical MRI scanning. If desired, the rotatable magnetic assembly 542 may be replaced by following a reverse method.

Figure 24A:
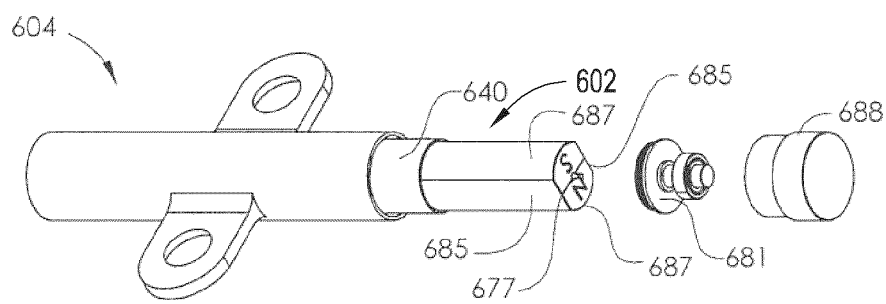
FIG. 24A illustrates a magnetic actuator of an adjustable spinal implant according to an embodiment of the present invention prior to removal of a radially-poled permanent magnet.
Figure 24B:
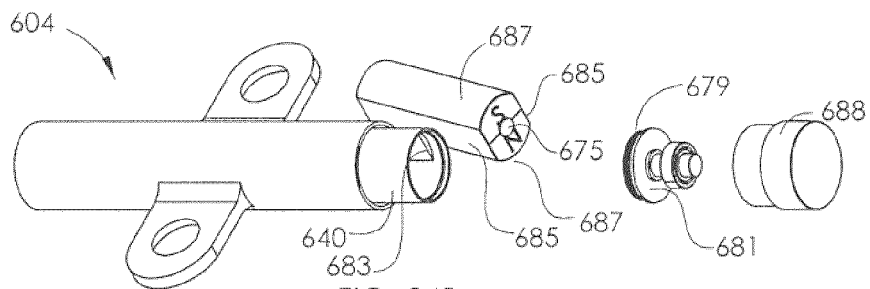
FIG. 24B illustrates a magnetic actuator of an adjustable spinal implant during removal of a radially-poled permanent magnet.
Figure 24C:
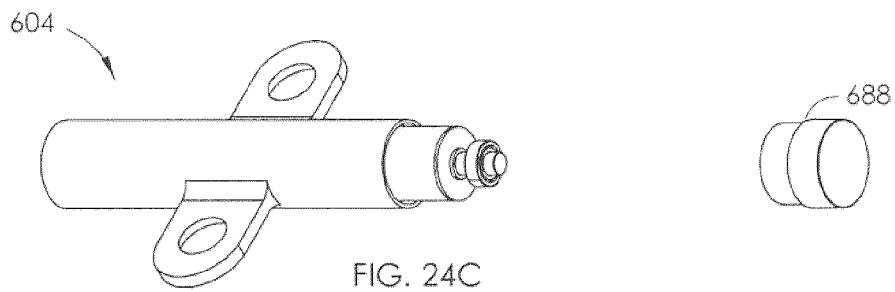
FIG. 24C illustrates a magnetic actuator of an adjustable spinal implant after removal of a radially-poled permanent magnet and replacement of a magnetic housing cap.
Figure 24D:
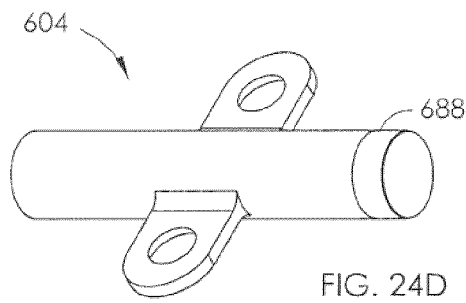
FIG. 24D illustrates a magnetic actuator of the adjustable spinal implant after replacement of an actuator housing cap.

FIGS. 24A through 24D illustrate a magnetic actuator 604 which may be used with any of the embodiments of the of devices as described and illustrated herein, and which allows for temporary or permanent removal of a radially-poled permanent magnet 602. An actuator housing cap 688 attaches to and detaches from the magnetic actuator 604 in the same manner as in the magnetic actuator 504 of FIGS. 23A through 23C. The radially-poled permanent magnet 602 has two radial portions 687 and two flat portions 685. The two flat portions 685 fit within flat walls 683 of a magnetic housing 640, which allows rotation of the radially-poled permanent magnet 602 to directly impart rotation on the magnetic housing 640 without the need for any adhesive or epoxy. A magnetic housing cap 681 having an o-ring 679 is attachable to and removable from the magnetic housing 640. If an MM of the subject is desired and it has been determined that the radially-poled permanent magnet 602 should be removed, a small incision may be made in the skin of the subject in close proximity to the actuator housing cap 688 through which the actuator housing cap 688 may be removed. The incision may be substantially at or near the location of an incision made during the implantation surgery, for example, adjacent or over the location of an incision made during the initial implantation surgery. Alternatively, the incision instead may be made in a separate location, as skin may be moved to access the magnetic actuator 604. Then magnetic housing cap 681 may then be removed from the magnetic housing 640. A pull rod 677 extends through a longitudinal hole (not shown) in the radially-poled permanent magnet 602, extending at one end such that it may be gripped, for example, by forceps or hemostats. The pull rod 677 has a flat base 675 at its opposite end so that, when pulled, it drags the radially-poled permanent magnet 602 with it. The radially-poled permanent magnet 602 may be removed, as shown in FIG. 24B (either permanently or temporarily) and the magnetic housing cap replaced (FIG. 24C). The actuator housing cap 688 may then be replaced (FIG. 24D). The incision may then be closed or allowed to close, and the subject may undergo typical MRI scanning. If desired, the radially-poled permanent magnet 602 may be replaced by following a reverse method. Alternatively, the magnetic housing cap 681 or the actuator housing cap 688 may be replaced by an alternatively shaped cap which will guide into a keyed structure within the magnet actuator 604 (not shown), thus keeping the internal mechanisms from turning, and keeping the subject's particular amount of adjustment from changing as the subject walks, runs and/or stretches.

When a desired magnitude of reduction has been reached—for example, lowering or maintaining the spondylolisthesis grade over a particular amount of time—any of the embodiments of the adjustable spinal implant disclosed herein may be removed from a patient. Alternatively, they may be left in place within a patient.

Figure 25:
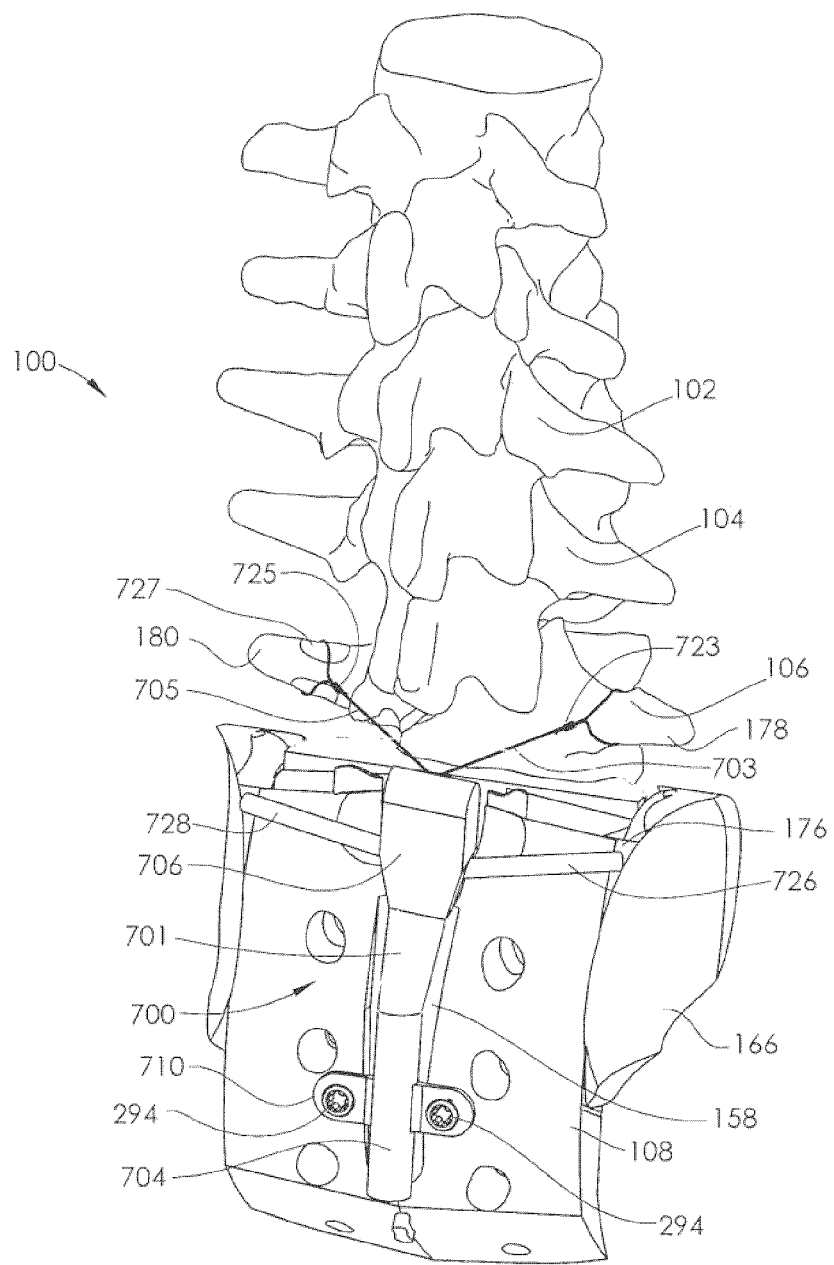
FIG. 25 illustrates an adjustable spinal implant according another embodiment of the present invention implanted on the spine of a subject with spondylolisthesis.
Figure 26:
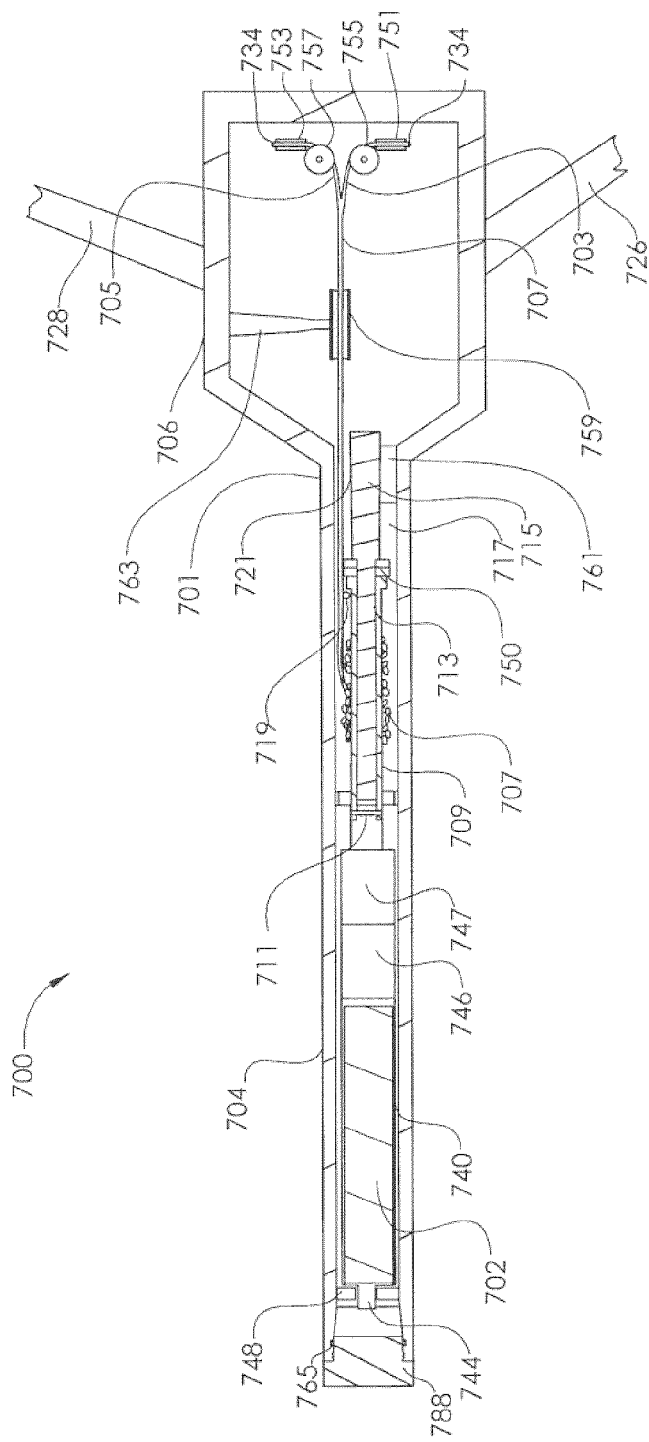
FIG. 26 illustrates a sectional view of the adjustable spinal implant of FIG. 25.

FIGS. 25 and 26 illustrate an adjustable spinal implant 700 according to another embodiment of the of devices as described and illustrated herein. The adjustable spinal implant 700 comprises an implantable actuator 704 having a transition section 701 which transitions to an adjustable element 706. Two feet 726 and 728 extending from the adjustable element 706 are configured to contact the medial surfaces 176 of the alas 166 of the sacrum 108. The implantable actuator 704 may have anchoring tabs 710 through which bone anchors 294 can be placed to secure the implantable actuator 704 to the sacrum 108. The adjustable element 706 features a tethering system for creating traction on the T5 vertebra 106. A right tether line 703 may be coupled to the right transverse process 178 of the L5 vertebra 106, and a left tether line 705 may be coupled to the left transverse process 180 of the L5 vertebra 106. The right tether line 703 and left tether line 705 are wrapped around each respective transverse process 178, 180 and secured to themselves via a crimp or clamp 723 and 725. This crimp or clamp 723 and 725 may be created using an appropriate tool during implantation, or may be pre-formed. In some embodiments, a durable surface 727 is wrapped around the transverse processes 178 and 180 first, in order to distribute contact stresses on the transverse processes 178 and 180.

The right tether line 703 and left tether line 705 enter the adjustable element 706 through a seal 734 (for example, an o-ring) which protects the inner contents of the adjustable element 706 from body fluids. The right and left tether lines 703 and 705 can wind first around first pulleys 751 and 753 and then around second pulleys 755 and 757 (which may be in an orthogonal plane to the first pulleys 751 and 753). The pulleys 751, 753, 755, and 757 may serve to guide the right and left tether lines 703, 705 towards the center of a cavity 717 in the adjustable spinal implant 700. In some embodiments, the right and left tether lines 703 and 705 bifurcate from single tether line 707 which extends over a main pulley 759 and is wound around a spool 709. In other embodiments, the right and left tether lines 703 and 705 themselves extend over a main pulley 759 and are then wound around a spool 709. The main pulley 759 can be held by post 763. The spool 709 can be rotationally held by a stepped post 721 having a large diameter portion 715 and a smaller diameter portion 713. The stepped post 721 is secured inside the adjustable spinal implant within the transition section 701 at a connection point 761. A radially-poled permanent magnet 702 is held within a magnetic housing 740 having a magnetic housing cap 744. The magnetic housing 744 cap and magnetic housing 740 are rotatable within a radial bearing 748. This portion of the assembly is enclosed by an actuator housing cap 788 and o-ring 765. The radially-poled permanent magnet 702 and thus magnetic housing 740 are coupled to a first planetary gear stage 746, which is in turn coupled to a second planetary gear stage 747. The second planetary gear stage 747 may be coupled to the spool 709 by pin 711. A thrust bearing 750 axially engages the spool 709 at the opposite end of the rotatable components from the radial bearing 748. A guide loop 719 assures that the single tether line 707 is smoothly wound around the spool 709. When a moving magnetic field is applied to the radially-poled permanent magnet 702 (for example, by use of the external adjustment device 1180), the radially-poled permanent magnet 702 and magnetic housing 740 can be caused to rotate, making the first and second planetary gear stages 746 and 747 rotate (at different rotational speeds as determined by the respective gear ratios) and thereby rotating the spool and taking up some of the single tether line 707. As the right and left tether lines 703 and 705 are pulled, traction (by the changing of tension and/or length of one or more of the tether lines 707, 703, 705) may be applied to the right and left transverse processes 178, 180, reducing the L5 vertebra 106 with respect to the sacrum 108. Alternatively, each of the tether lines 703, 705 may be wound on its own spool/magnet assembly and thus be independently adjustable. For example, the right tether line 703 may extend from a first actuator and the left tether line 705 may extend form a second actuator, with the first actuator independently adjustable from the second actuator.

Figure 27:
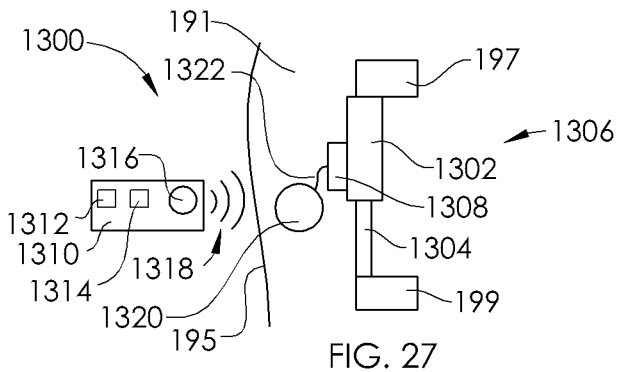
FIGS. 27-30 schematically illustrate various embodiments of alternate sources of a driving element of a non-invasively adjustable spinal implant.

FIGS. 27-30 illustrate embodiments of a driving element alternative that may be used instead of a rotatable magnetic assembly as the driving element 242 of a non-invasively adjustable spinal implant. FIG. 27 illustrates a non-invasively adjustable spinal system 1300 comprising an implant 1306 having a first implant portion 1302 and a second implant portion 1304, the second implant portion 1304 non-invasively displaceable with relation to the first implant portion 1302. The first implant portion 1302 is secured to a first bone portion 197 and the second implant portion 1304 is secured to a second bone portion 199 within a patient 191. A motor 1308 is operable to cause the first implant portion 1302 and the second implant portion 1304 to displace relative to one another. An external adjustment device 1310 has a control panel 1312 for input by an operator, a display 1314 and a transmitter 1316. The transmitter 1316 sends a control signal 1318 through the skin 195 of the patient 191 to an implanted receiver 1320. Implanted receiver 1320 communicates with the motor 1308 via a conductor 1322. The motor 1308 may be powered by an implantable battery, or may be powered or charged by inductive coupling.

Figure 28:
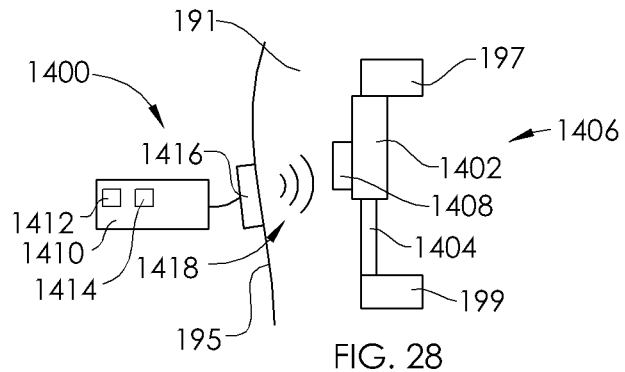

FIG. 28 illustrates a non-invasively adjustable spinal system 1400 comprising an implant 1406 having a first implant portion 1402 and a second implant portion 1404, the second implant portion 1404 non-invasively displaceable with relation to the first implant portion 1402. The first implant portion 1402 is secured to a first bone portion 197 and the second implant portion 1404 is secured to a second bone portion 199 within a patient 191. An ultrasonic motor 1408 is operable to cause the first implant portion 1402 and the second implant portion 1404 to displace relative to one another. An external adjustment device 1410 has a control panel 1412 for input by an operator, a display 1414 and an ultrasonic transducer 1416, which is coupled to the skin 195 of the patient 191. The ultrasonic transducer 1416 produces ultrasonic waves 1418 which pass through the skin 195 of the patient 191 and operate the ultrasonic motor 1408.

Figure 29:
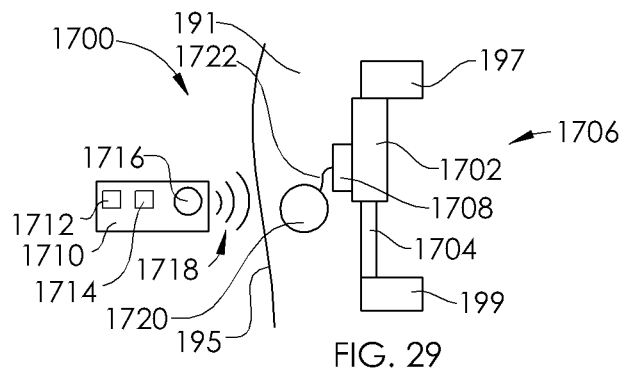

FIG. 29 illustrates a non-invasively adjustable spinal system 1700 comprising an implant 1706 having a first implant portion 1702 and a second implant portion 1704, the second implant portion 1704 non-invasively displaceable with relation to the first implant portion 1702. The first implant portion 1702 is secured to a first bone portion 197 and the second implant portion 1704 is secured to a second bone portion 199 within a patient 191. A shape memory actuator 1708 is operable to cause the first implant portion 1702 and the second implant portion 1704 to displace relative to one another. An external adjustment device 1710 has a control panel 1712 for input by an operator, a display 1714 and a transmitter 1716. The transmitter 1716 sends a control signal 1718 through the skin 195 of the patient 191 to an implanted receiver 1720. Implanted receiver 1720 communicates with the shape memory actuator 1708 via a conductor 1722. The shape memory actuator 1708 may be powered by an implantable battery, or may be powered or charged by inductive coupling.

Figure 30:
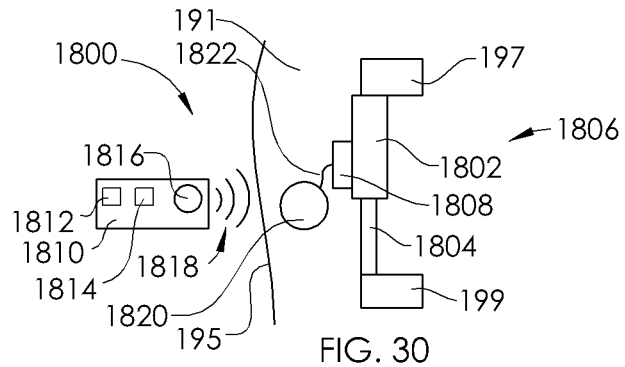

FIG. 30 illustrates a non-invasively adjustable spinal system 1800 comprising an implant 1806 having a first implant portion 1802 and a second implant portion 1804, the second implant portion 1804 non-invasively displaceable with relation to the first implant portion 1802. The first implant portion 1802 is secured to a first bone portion 197 and the second implant portion 1804 is secured to a second bone portion 199 within a patient 191. A hydraulic pump 1808 is operable to cause the first implant portion 1802 and the second implant portion 1804 to displace relative to one another. An external adjustment device 1810 has a control panel 1812 for input by an operator, a display 1814 and a transmitter 1816. The transmitter 1816 sends a control signal 1818 through the skin 195 of the patient 191 to an implanted receiver 1820. Implanted receiver 1820 communicates with the hydraulic pump 1808 via a conductor 1822. The hydraulic pump 1808 may be powered by an implantable battery, or may be powered or charged by inductive coupling. The hydraulic pump 1808 may alternatively be replaced by a pneumatic pump.

While embodiments of the present invention have been shown and described, various modifications may be made without departing from the scope of the present invention. Supplementation (graft) may be applied during the initial implantation of an embodiment of the adjustable spinal implant, and the adjustments may be made during the time period that the fusion is occurring, for example, less than six months, or more specifically, less than three months. This may, for example, include fusion being attempted between L5 106 and S1 122. The treatment of the patient may be to reduce the grade of spondylolisthesis, as described, but in certain cases, the goal may be simply to maintain the grade of spondylolisthesis in an otherwise progressing patient; for example, to keep spondyloptosis from occurring. In subjects who have undersized transverse processes, some augmentation of the transverse processes may be done prior to securing one of the embodiments of the present invention. In some cases, pedicle screws may be used instead of or to augment the connection to the transverse processes. An additional fulcrum may be placed between the vertebrae being treated (e.g., a wedge implant) in order to aid the derotation. The embodiments of the present invention may also be used in conditions other than spondylolisthesis, for example, ankylosing spondylitis. The invention, therefore, should not be limited, except to the following claims, and their equivalents.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "securing at least a portion of the non-invasively adjustable implant to a portion of the sacrum of the subject" include "instructing the securing at least a portion of the non-invasively adjustable implant to a portion of the sacrum of the subject." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers, and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A non-invasively adjustable spinal system, comprising:
   an actuator configured for remote activation, the actuator having an output shaft and at least one anchoring structure configured to facilitate securement of the actuator to a portion of a sacrum;
   an adjustment element comprising:
      a gear housing;
      at least one gear disposed in the gear housing, the at least one gear operably coupled to the output shaft of the actuator by a universal joint disposed within a flexible tubular member, with the at least one gear further comprising a pinion;
      an engagement structure having at least one transverse process hook configured to engage at least one transverse process of a lumbar vertebra, and a moveable arm at least partially disposed within the gear housing, wherein the moveable arm forms an arcuate rack that extends from the engagement structure and is configured to communicate with the pinion and wherein the pinion is configured to move the engagement structure along an arcuate path upon remote activation of the actuator; and
   a plurality of feet disposed on the adjustment element, each of the plurality of feet configured to extend between the adjustment element and the sacrum, and configured to stabilize the adjustment element with respect to the sacrum.

2. The non-invasively adjustable spinal system of claim 1, wherein the engagement structure is configured to engage at least one transverse process of an L5 lumbar vertebra.

3. The non-invasively adjustable spinal system of claim 1, wherein the engagement structure is configured to engage both transverse processes of a lumbar vertebra.

4. The non-invasively adjustable spinal system of claim 3, wherein the engagement structure comprises a cross bar having a left transverse process hook and a right transverse process hook.

5. The non-invasively adjustable spinal system of claim 1, wherein the actuator further comprises a driving element selected from the group consisting of: a permanent magnet, an inductively coupled motor, an ultrasonically actuated motor, a subcutaneous hydraulic pump, a subcutaneous pneumatic pump, and a shape-memory driven actuator.

6. The non-invasively adjustable spinal system of claim 5, wherein the driving element comprises a radially-poled permanent magnet configured for rotation within the actuator.

7. The non-invasively adjustable spinal system of claim 6, wherein the radially-poled permanent magnet is configured to be rotated by application of a rotating magnetic field.

8. The non-invasively adjustable spinal system of claim 6, wherein the radially-poled permanent magnet is removable from the implantable actuator.

9. The non-invasively adjustable spinal system of claim 6, further comprising: an external adjustment device configured to produce a rotating magnetic field capable of rotating the radially-poled permanent magnet.

10. The non-invasively adjustable spinal system of claim 9, further comprising at least one electromagnet.

11. The non-invasively adjustable spinal system of claim 1, wherein the engagement structure comprises at least one transverse process hook.

12. The non-invasively adjustable spinal system of claim 1, further comprising:
   a second actuator;
   a first transverse process hook, coupled to the implantable actuator; and
   a second transverse process hook, coupled to the second implantable actuator.

13. The non-invasively adjustable spinal system of claim 12, wherein the implantable actuator is independently adjustable from the second implantable actuator.

14. The non-invasively adjustable spinal system of claim 1, wherein the adjustment element comprises a traction element.

* * * * *